United States Patent
Monje-Deisseroth et al.

(10) Patent No.: US 10,550,388 B2
(45) Date of Patent: Feb. 4, 2020

(54) TARGETING PLEIOTROPHIN SIGNALING TO LIMIT HIGH-GRADE GLIOMA INVASION

(71) Applicant: The Board of Trustees of the Leland Stanford Junior University, Stanford, CA (US)

(72) Inventors: Michelle Monje-Deisseroth, Stanford, CA (US); Elizabeth Qin, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/998,437

(22) Filed: Aug. 15, 2018

(65) Prior Publication Data
US 2019/0055556 A1 Feb. 21, 2019

Related U.S. Application Data

(60) Provisional application No. 62/545,622, filed on Aug. 15, 2017.

(51) Int. Cl.
| | |
|---|---|
| C12N 15/113 | (2010.01) |
| A61K 31/4439 | (2006.01) |
| A61K 31/5377 | (2006.01) |
| A61K 31/7105 | (2006.01) |
| A61K 31/713 | (2006.01) |
| A61K 9/08 | (2006.01) |
| A61P 35/00 | (2006.01) |
| A61K 45/06 | (2006.01) |
| A61K 9/00 | (2006.01) |

(52) U.S. Cl.
CPC .......... *C12N 15/113* (2013.01); *A61K 9/0019* (2013.01); *A61K 9/0085* (2013.01); *A61K 31/4439* (2013.01); *A61K 31/5377* (2013.01); *A61K 31/713* (2013.01); *A61K 31/7105* (2013.01); *A61K 45/06* (2013.01); *A61P 35/00* (2018.01); *C12N 2310/11* (2013.01); *C12N 2310/122* (2013.01); *C12N 2310/14* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 8,541,568 B2 | 9/2013 | Yan et al. | |
| 8,772,471 B2 | 7/2014 | Shankar et al. | |
| 2012/0183538 A1 | 7/2012 | Trieu | |
| 2013/0004429 A1* | 1/2013 | Eyer | A61K 38/16 424/9.6 |
| 2013/0224208 A1* | 8/2013 | Kondo | A61K 31/542 424/138.1 |
| 2016/0361300 A1* | 12/2016 | Schwartz | A61K 9/0053 |

FOREIGN PATENT DOCUMENTS

| | | |
|---|---|---|
| CN | 106591306 A | 4/2017 |
| WO | 2017132291 A1 | 1/2017 |

OTHER PUBLICATIONS

Lu et al. (2005) Differential Induction of Glioblastoma Migration and Growth by Two Forms of Pleiotrophin. J. Biol. Chem. 280, 26953-26964.
Ulbricht et al. (2003) Expression and function of the receptor protein tyrosine phosphatase zeta and its ligand pleiotrophin in human astrocytomas. J. Neuropathol. Exp. Neurol. 62, 1265-1275.
Li et al. (1990) Cloning and expression of a developmentally regulated protein that induces mitogenic and neurite outgrowth activity. Science 250, 1690-1694.
Rauvala and Pihlaskari (1987) Isolation and some characteristics of an adhesive factor of brain that enhances neurite outgrowth in central neurons. J. Biol. Chem. 262, 16625-16635.
Maeda and Noda (1998) Involvement of receptor-like protein tyrosine phosphatase zeta/RPTPbeta and its ligand pleiotrophin/heparin-binding growth-associated molecule (HB-GAM) in neuronal migration. J. Cell Biol. 142(1), 203-216.
Muller et al. (2003) A role for receptor tyrosine phosphatase zeta in glioma cell migration. Oncogene 22, 6661-6668.
Grasso et al. (2015) Functionally defined therapeutic targets in diffuse intrinsic pontine glioma. Nat. Med. 21, 555-559.
Nagaraja et al. (2017) Transcriptional Dependencies in Diffuse Intrinsic Pontine Glioma. Cancer Cell 31, 635-652. e6.
Egorin et al. (2001) Plasma pharmacokinetics and tissue distribution of 17-(allylamino)-17-demethoxygeldanamycin (NSC 330507) in CD2F1 mice1. Pharmacol. 47, 291-302.
Fujikawa et al. (2011) J. Biol. Chem. 286, 37137-37146.
Kuboyama et al. (2012) PLoS One 7, e48797.
Niisato et al. (2005) Age-dependent enhancement of hippocampal long-term potentiation and impairment of spatial learning through the Rho-associated kinase pathway in protein tyrosine phosphatase receptor type Z-deficient mice. J. Neurosci. 25, 1081-1088.
Tamura et al. (2006) Protein tyrosine phosphatase receptor type Z is involved in hippocampus-dependent memory formation through dephosphorylation at Y1105 on p190 RhoGAP. Neurosci. Lett. 399, 33-38.
Parri and Chiarugi (2010) Rac and Rho GTPases in cancer cell motility control. Cell Commun Signal 8, 23.
Aboody et al. (2000) Neural stem cells display extensive tropism for pathology in adult brain: evidence from Intracranial gliomas. Proc. Natl. Acad. Sci. U.S.A. 97, 12846-12851.
Li et al. (2007) Genetically engineered neural stem cells migrate and suppress glioma cell growth at distant intracranial sites. Cancer Lett. 251, 220-227.

(Continued)

*Primary Examiner* — Tracy Vivlemore
(74) *Attorney, Agent, or Firm* — Jenny L. Buchbinder; Bozicevic, Field & Francis LLP

(57) ABSTRACT

Compositions and methods for treatment of glioma are disclosed. In particular, the invention relates to methods of treating glioma by inhibiting pleiotrophin signaling to limit high-grade glioma invasion.

26 Claims, 79 Drawing Sheets

Specification includes a Sequence Listing.

(56) References Cited

OTHER PUBLICATIONS

Reitz et al. (2012) Intranasal delivery of neural stem/progenitor cells: a noninvasive passage to target intracerebral glioma. Stem Cells Transl. Med. 1, 866-873.
Ehtesham et al. (2004) Glioma tropic neural stem cells consist of astrocytic precursors and their migratory capacity is mediated by CXCR4. Neoplasia 6(3), 287-293.
Imitola et al. (2004) Directed migration of neural stem cells to sites of CNS injury by the stromal cell-derived factor 1alpha/CXC chemokine receptor 4 pathway. Proc. Natl. Acad. Sci. U.S.A. 101, 18117-18122.
Magge et al. (2009) Role of monocyte chemoattractant protein-1 (MCP-1/CCL2) in migration of neural progenitor cells toward glial tumors. J. Neurosci. Res. 87, 1547-1555.
An et al. (2009) Identification of gliotropic factors that induce human stem cell migration to malignant tumor. J. Proteome Res. 8, 2873-2881.
Chaichana et al. (2008) Relationship of glioblastoma multiforme to the lateral ventricles predicts survival following tumor resection. J. Neurooncol. 89, 219-224.
Jafri et al. (2013) Relationship of glioblastoma multiforme to the subventricular zone is associated with survival. Neuro. Oncol. 15, 500 91-96.
Mistry et al. (2017) Influence of glioblastoma contact with the lateral ventricle on survival: a meta-analysis. J. Neurooncol. 131, 125-133.
Mistry et al. (2017) Decreased survival in glioblastomas is specific to contact with the ventricular-subventricular zone, not subgranular zone or corpus callosum. J. Neurooncol. 132(2):341-349.
Adeberg et al. (2014) Glioblastoma recurrence patterns after radiation therapy with regard to the subventricular zone.Int. J. Radiat. Oncol. Biol. Phys. 90, 886-893.
Chen et al. (2015) Glioblastoma recurrence patterns near neural stem cell regions. Radiother. Oncol. 116, 294-300.
Caretti et al. (2014) Subventricular spread of diffuse intrinsic pontine glioma. Acta Neuropathol. 128, 605-607.
Gonzalez-Castillo et al. (2015) Pleiotrophin as a central nervous system neuromodulator, evidences from the hippocampus. Front. Cell. Neurosci. 8, 443.
Kinnunen et al. (1999) Heparan sulphate and HB-GAM (heparin-binding growth-associated molecule) in the development of the thalamocortical pathway of rat brain. Eur. J. Neurosci. 11, 491-502.
Staflin et al. (2009) Identification of proteins involved in neural progenitor cell targeting of gliomas. BMC Cancer 9, 206.
Tsirmoula et al. (2012) Implications of pleiotrophin in human PC3 prostate cancer cell growth in vivo. Cancer Sci. 103, 1826-1832.
Wellstein et al. (1992) A heparin-binding growth factor secreted from breast cancer cells homologous to a developmentally regulated cytokine. J. Biol. Chem. 267, 2582-2587.
Czubayko et al. (1996) Melanoma angiogenesis and metastasis modulated by ribozyme targeting of the secreted growth factor pleiotrophin. Proc. Natl. Acad. Sci. U.S.A. 93, 14753-14758.
Wu et al. (2005) Pleiotrophin expression correlates with melanocytic tumor progression and metastatic potential. J. Cutan. Pathol. 32, 125-130.
Zhang et al. (2015) Pleiotrophin promotes vascular abnormalization in gliomas and correlates with poor survival in patients with astrocytomas. Sci. Signal. 8, ra125.
Zhou et al. (2012) Effects of SEMA3G on migration and invasion of glioma cells. Oncol. Rep. 28, 269-275.
Lin et al. (2009) Danthron inhibits the migration and invasion of human brain glioblastoma multiforme cells through the inhibition of mRNA expression of focal adhesion kinase, Rho kinases-1 and metalloproteinase-9. Oncol. Rep. 22, 1033-1037.
Oellers et al. (2009) ROCKs are expressed in brain tumors and are required for glioma-cell migration on myelinated axons. Glia 57, 499-509.
Salhia et al. (2005) Inhibition of Rho-kinase affects astrocytoma morphology, motility, and invasion through activation of Rac1. Cancer Res. 65, 8792-8800.
Nakada et al. (2010) The phosphorylation of ephrin-B2 ligand promotes glioma cell migration and invasion. Int. J. Cancer 126, 1155-1165.
Sikkema et al. (2012) EphB2 activity plays a pivotal role in pediatric medulloblastoma cell adhesion and invasion. Neuro. Oncol. 14, 1125-1135.
Shimizu et al. (2013) Netrin-1 promotes glioblastoma cell invasiveness and angiogenesis by multiple pathways including activation of RhoA, cathepsin B, and cAMP-response element-binding protein. J. Biol. Chem. 288, 2210-2222.
Brose et al. (1999) Slit Proteins Bind Robo Receptors and Have an Evolutionarily Conserved Role in Repulsive Axon Guidance. Cell 96, 795-806.
Mertsch et al. (2008) Slit2 involvement in glioma cell migration is mediated by Robo1 receptor. J. Neurooncol. 87, 1-7.
Kidd et al. (1999) Slit is the Midline Repellent for the Robo Receptor in *Drosophila*. Cell 96, 785-794.
Li and Lee (2010) Semaphorin 5A and plexin-B3 inhibit human glioma cell motility through RhoGDlalpha-mediated inactivation of Rac1 GTPase. J. Biol. Chem. 285, 32436-32445.

\* cited by examiner

| List of candidate proteins |
|---|
| BCAN |
| GRP78 |
| HSP90B |
| IGFBP2 |
| IGFBP4 |
| PTN |
| SPARC |
| SPARCL1 |

FIG. 3F

TARGETING PLEIOTROPHIN SIGNALING TO LIMIT HIGH-GRADE GLIOMA INVASION

CROSS-REFERENCE TO RELATED APPLICATION

This application claims benefit under 35 U.S.C. § 119(e) of provisional application 62/545,622, filed Aug. 15, 2017, which application is hereby incorporated by reference in its entirety.

STATEMENT REGARDING FEDERALLY SPONSORED RESEARCH OR DEVELOPMENT

This invention was made with government support under contracts NS092597 awarded by the National Institutes of Health and NF140075 awarded by the Department of Defense. The government has certain rights in the invention.

TECHNICAL FIELD

The present invention pertains generally to treatment of glioma. In particular, the invention relates to methods of treating glioma by inhibiting pleiotrophin signaling to limit high-grade glioma invasion.

BACKGROUND

High-grade gliomas (HGGs) are a diffusely infiltrating group of cancers with dire prognoses. The lateral ventricle subventricular zone (SVZ) stem cell niche is thought to be a tumor reservoir for a range of HGGs including adult glioblastoma (GBM). Glioma contact of neural stem cell niches, particularly the subventricular zone, has been closely associated with decreased survival (Chaichana et al. (2008) J. Neurooncol. 89, 219-224; Jafri et al. (2013) Neuro. Oncol. 15, 500 91-96; Mistry et al. (2017) J. Neurooncol. 131, 125-133; Mistry et al. (2017) J. Neurooncol. 132(2):341-349) and increased tumor recurrence (Adeberg et al. (2014) Int. J. Radiat. Oncol. Biol. Phys. 90, 886-893; Chen et al. (2015) Radiother. Oncol. 116, 294-300). Diffuse intrinsic pontine glioma (DIPG; recently re-classified as diffuse midline glioma, H3K27M mutant (Louis et al. (2016) Acta Neuropathol. 131, 803-820) is the most common HGG of childhood and the leading cause of pediatric brain tumor-related death, with a median survival of only 9 months and a 5-year survival of less than 1% (Donaldson et al. (2006) J. Clin. Oncol. 24(8), 1266-1272). DIPG tends to not only infiltrate the brainstem, where it originates, but also the forebrain, with a particular propensity for spread to the SVZ, which occurs in ~65% of cases (Caretti et al. (2014) Acta Neuropathol. 128, 605-607). A point of debate regarding SVZ involvement in adult GBM has been whether gliomas spread to the SVZ or whether the cancer originates there. In DIPG, the tumor clearly begins in the pons and from some anatomical distance spreads to the lateral ventricle SVZ, clarifying the propensity of HGGs to travel to the SVZ niche. DIPG is thus an illustrative tumor type in which to discern the mechanisms of SVZ invasion that may be broadly relevant to HGGs.

There remains a need for better methods of treating glioma, particularly to limit SVZ invasion.

SUMMARY

The invention relates to methods of treating glioma by inhibiting pleiotrophin signaling to limit high-grade glioma invasion. In particular, the methods inhibit glioma tropism towards the brain SVZ by blocking assembly of a chemoattractant complex comprising pleiotrophin (PTN), heat shock protein 90B (HSP90B), secreted protein acidic and rich in cysteine (SPARC), and SPARC-like protein 1 (SPARCL1), which is responsible for homing of glioma cells to the SVZ. In addition, inhibition of pleiotrophin signaling through the protein tyrosine phosphatase receptor type ζ PTPRZ also reduces glioma invasion of the SVZ.

In one aspect, the invention includes a method of treating glioma comprising administering to a subject in need thereof a therapeutically effective amount of an inhibitor of pleiotrophin signaling.

In certain embodiments, the method of treating glioma comprises administering to the subject a therapeutically effective amount of at least one inhibitory nucleic acid that inhibits expression of one or more genes selected from the group consisting of PTN, HSP90B, SPARC, SPARCL1, and PTPRZ.

In certain embodiments, at least one inhibitory nucleic is selected from the group consisting of a short hairpin RNA (shRNA), a small interfering RNA (siRNA), a microRNA (miRNA), and an anti sense oligonucleotide.

In certain embodiments, the inhibitory nucleic is an shRNA comprising a nucleotide sequence selected from the group consisting of SEQ ID NOS:7-13, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the shRNA is capable of inhibiting expression of one or more genes selected from the group consisting of PTN, HSP90B, SPARC, SPARCL1, and PTPRZ.

In certain embodiments, the glioma is a high-grade glioma, such as, but not limited to, diffuse intrinsic pontine glioma (DIPG), adult glioblastoma, adult anaplastic oligodendroglioma, and pediatric spinal cord high-grade glioma. In another embodiment, the glioma is a DIPG subtype, selected from the group consisting of an H3.3K27M mutant DIPG subtype and an H3.1 K27M mutant DIPG subtype.

In another embodiment, the inhibitory nucleic is administered stereotactically into the brain of the subject.

In another embodiment, treatment reduces glioma invasion toward a brain subventricular zone.

In another embodiment, knockdown of at least one gene selected from the group consisting of PTN, HSP90B, SPARC, and SPARCL1 inhibits assembly of a chemoattractant complex in the brain subventricular zone.

In another embodiment, knockdown of PTN or PTPRZ inhibits pleiotrophin signaling through protein tyrosine phosphatase receptor type ζ.

In another embodiment, knockdown of PTN or PTPRZ reduces activation of RhoA and Rho kinase (ROCK).

In another embodiment, multiple cycles of treatment are administered to the subject for a time period sufficient to effect at least a partial tumor response, or more preferably, a complete tumor response.

In another embodiment, the method further comprises administering a Rho kinase (ROCK) inhibitor to the subject, for example, a GSK 429286 or GSK 269962A ROCK inhibitor.

In another embodiment, the method further comprising performing surgery, radiation therapy, chemotherapy, or anti-angiogenic therapy.

In another aspect, the invention includes a method of inhibiting glioma tropism towards a brain subventricular zone in response to a chemoattractant complex, the method comprising administering to a subject in need thereof at least one inhibitory nucleic acid that inhibits expression of one or more genes selected from the group consisting of PTN, HSP90B, SPARC, and SPARCL1, wherein said at least one inhibitory nucleic acid is administered in an amount sufficient to interfere with assembly of the chemoattractant complex in the brain subventricular zone.

These and other embodiments of the subject invention will readily occur to those of skill in the art in view of the disclosure herein.

BRIEF DESCRIPTION OF THE FIGURES

FIG. 1A shows MRI (coronal, T1 post-gadolinium) and H&E micrograph (inset) of tumor in the SVZ of a 6-year-old female with DIPG (subject SU-DIPG-XIII). Scale bar, 50 μm. FIGS. 1B and 1C show an H&E micrograph of a tumor in the lateral wall of the lateral ventricle SVZ in a 12-year old female with DIPG (subject SU-DIPG-V). Scale bars, 1 mm (FIG. 1B), 50 μm (FIG. 1C). FIGS. 1D and 1E show DIPG cells isolated from tumor in the SVZ (SU-DIPG-XIII FL cells) recapitulate invasion of the forebrain when orthotopically xenografted in NSG mice as shown in bioluminescent IVIS imaging (FIG. 1D), as well as invasion of the SVZ as shown by histological analysis (FIG. 1E). Lateral ventricle outlined in dashed white lines. Scale bar, 40 μm (FIG. 1F) SU-DIPG-XIII FL cells (GFP$^+$ HNA$^+$) and neural precursor cells (Sox2$^+$ GFAP$^+$) in the SVZ stem cell niche in an NSG mouse orthotopically xenografted with DIPG cells. Scale bar, 20 μm. FIG. 1G shows that SU-DIPG-XIII FL cells invade widely throughout the brain over time, with 100% of mice exhibiting tumor in the SVZ by 16 weeks post-xenograft.

FIGS. 2A and 2B show that schematic and Matrigel invasion assay results of DIPG cells invading toward mNPC CM (FIG. 2A) or when co-incubated with mNPC CM (FIG. 2B). DIPG cells invade preferentially toward SVZ mNPC CM compared to other mNPC CM or unconditioned mNPC media. Direct exposure to 4VZ mNPC CM modestly increases general DIPG invasion. n=3 replicates/wells in SU-DIPG-XIII FL cells and analyzed by one-way ANOVA with Tukey post hoc adjustment for multiple comparisons. FIG. 2C shows that 18 out of a panel of 24 patient-derived glioma cultures (see Table 1) invade preferentially toward SVZ hNPC CM compared to unconditioned hNPC media. n=3 replicates/wells and analyzed by unpaired, two-tailed Student's t-tests for comparison between unconditioned and conditioned hNPC media. Data shown as mean±SEM. *$p<0.05$, $p<0.01$, *$p<0.001$.

FIGS. 3A-3F show that NPC-secreted factors promoting invasion are proteins. FIGS. 3A and 3C show that boiling, but not RNase and/or DNase treatment, abrogates the invasion-promoting effects of SVZ hNPC CM (FIG. 3A) and 4VZ mNPC CM (FIG. 3C). FIGS. 3B and 3D show that size fractionation of SVZ hNPC CM (FIG. 3B) and 4VZ mNPC CM (FIG. 3D) reveals that the invasion-promoting factor(s) are greater than 30 kDa in size. All experiments performed with n=3 replicates/wells in SU-DIPG-XIII FL cells and analyzed by unpaired, two-tailed Student's t-test for comparison between unconditioned and conditioned media (FIGS. 3A, 3C) or by one-way ANOVA with Tukey post hoc adjustment for multiple comparisons (FIGS. 3B, 3D). Data shown as mean±SEM. $p<0.01$, *$p<0.001$. FIG. 3E shows a two-dimensional gel electrophoresis separating proteins in SVZ mNPC CM and 4VZ mNPC CM by size (vertical axis) and charge (horizontal axis). FIG. 3F shows a list of candidate proteins of interest identified from proteomic analysis that were differentially expressed in SVZ mNPC CM compared to 4VZ mNPC CM by a factor of 1.5.

FIG. 4A shows that no single candidate recombinant protein significantly increased DIPG invasion compared to unconditioned hNPC media. FIG. 4B shows that the combination of four factors: PTN, SPARC, SPARCL1, and HSP90B, was sufficient for the full invasion-promoting effect toward SVZ hNPC CM. No combination of two or three factors was sufficient. All experiments performed with n=3 replicates/wells in SU-DIPG-XIII FL cells and analyzed by one-way ANOVA with. Tukey post hoc adjustment for multiple comparisons (FIG. 4A) or Dunnett post hoc adjustment for multiple comparisons to either SVZ hNPC CM or the combination of all 4 factors (FIG. 4B). FIG. 4C shows that all four proteins coeluted at approximately the 212 kDa size expected for a complex of all four proteins by size exclusion chromatography. FIG. 4D shows that all four proteins copurified together in immunoprecipitation reactions for any one of the four proteins, more so than with a control IgG. Three control proteins also present in SVZ hNPC CM: GRP78, IGFBP2, and BCAN, did not copurify with any of the four proteins. FIG. 4E shows that 9 out of a panel of 9 patient-derived glioma cultures (see Table 1) invade preferentially toward the combination of four proteins similarly to toward human SVZ NPC CM, compared to unconditioned hNPC media. All experiments performed with n=3 replicates/wells and analyzed by unpaired, two-tailed Student's t-tests for comparison between unconditioned and conditioned hNPC media. Data shown as mean±SEM. *$p<0.05$, $p<0.01$, *$p<0.001$.

FIG. 5A shows that the PTN protein is highly localized to the SVZ and pia mater (white arrowhead) in the adult murine brain (left). PTN is expressed at lower levels in the 3VZ (left middle) and 4VZ (right), and is undetectable in the hippocampus (right middle). Scale bar, 1 mm. LV=lateral ventricle. 3V=third ventricle. 4V=fourth ventricle. FIG. 5B shows that the PTN protein expression near the lateral ventricles and in the pia (white arrowheads) in the postnatal murine brain at P0, 5, and 10. Scale bar, 1 mm. FIG. 5C shows that the PTN protein is highly expressed in the human SVZ of an 8-year-old female (left) and a 68-year-old male (right). PTN protein co-localizes with Nestin$^+$ NPCs in the SVZ and is also present extracellularly. Scale bar, 1 mm. FIG. 5D shows high magnification images of PTN expression co-localizing with Nestin$^+$ NPCs in the SVZ of a 68-year-old male. Scale bar, 25 μm. FIGS. 5E and 5G show that the Ptn gene (FIG. 5E) and PTN protein expression (FIG. 5G) are higher in SVZ mNPCs isolated from P14 WT mice, compared to 3VZ, 4VZ, or DG mNPCs isolated at the same age. Gene expression values shown are normalized to ACTB expression. qPCR experiments performed with n=3 wells of cells and analyzed by one-way ANOVA with Tukey post hoc adjustment for multiple comparisons. (F and H) Ptn gene (FIG. 5F) and PTN protein expression (FIG. 5H) is higher in the SVZ compared to cortex of P42 mice. Gene expression values shown are normalized to ACTB expression. qPCR experiments performed with n=3 mice and analyzed by unpaired, two-tailed Student's t-test. Data shown as mean±SEM. *$p<0.05$, **$p<0.01$.

FIG. 6A shows that DIPG cells invade less toward SVZ hNPC CM after immunodepletion of any or a combination of the four proteins. Depletion of target proteins was confirmed by Western blot. FIG. 6B shows that DIPG cells invade less toward CM from SVZ hNPCs that had any or all of the four proteins knocked down by shRNA-expressing lentivirus, compared to CM from SVZ hNPCs expressing a scrambled shRNA control. Knockdown efficacy was confirmed by Western blot. In vitro experiments performed with n=3 replicates/wells in SU-DIPG-XIII FL cells and analyzed by one-way ANOVA with Tukey post hoc adjustment for multiple comparisons. FIGS. 6C and 6E show that fewer orthotopically xenografted GFP$^+$ HNA$^+$ SU-DIPG-XIII FL cells invaded the SVZ, defined as a 200 μm-wide region adjacent to the lateral ventricles (outlined in dashed white lines), when lentivirus expressing sh-Ptn (right) was injected into the SVZ, compared to lentivirus expressing a scrambled shRNA control (left). Scale bar, 200 μm. FIGS. 6D and 6F show that the density of Sox2$^+$ neural stem/precursor cells in the SVZ was equivalent in mice injected with lentivirus expressing sh-Ptn (right) or scrambled shRNA control (left). Scale bar, 50 μm. In vivo experiments performed with n=5 mice per group. Stereological cell counts at 16 weeks following xenograft analyzed by unpaired, two-tailed Student's t-test. Each data point=one mouse (FIGS. 6E-6F). Data shown as mean±SEM. *$p<0.05$, $p<0.01$, *$p<0.001$.

FIGS. 7A and 7B show exposure of DIPG cells to SVZ hNPC CM activated RhoA after 1-5 minutes (FIG. 7A) and ROCK after 60-120 minutes (FIG. 7B), compared to unconditioned hNPC media. FIGS. 7C and 7D show exposure to PTN and the three binding partners in unconditioned hNPC media activated RhoA (FIG. 7C) and ROCK (FIG. 7D) similarly to SVZ hNPC CM. FIGS. 7E and 7F show that treatment with ROCK inhibitors GSK 429286 or GSK 269962A decreased DIPG invasion toward SVZ hNPC CM in a dose-dependent manner. All experiments performed with n=3 replicates/wells in SU-DIPG-XIII FL cells and analyzed by unpaired two-tailed Student's t-tests for comparison between unconditioned and conditioned hNPC media (FIGS. 7A and 7B) or by one-way ANOVA with Tukey post hoc adjustment for multiple comparisons (FIGS. 7C and 7F). Data shown as mean±SEM. *$p<0.05$, $p<0.01$, *$p<0.001$. FIG. 7G shows a schematic illustrating the model of glioma cells originating in the pons invading generally in the ventral pons, and being drawn at short to medium range into the SVZ upon exposure to PTN and the three binding partners secreted by SVZ NPCs. FIG. 7H shows a schematic illustrating the model of glioma chemoattraction toward NPC-secreted PTN and the three binding partners, subsequent activation of the Rho/ROCK pathway in glioma cells, and promotion of glioma cell migration and invasion.

FIGS. 8A and 8B show copy number plots of whole exome sequencing of DIPG cells isolated from the pons (FIG. 8A) and from an SVZ site of spread (FIG. 8B) from the same individual (SU-DIPG-XIII). FIG. 8C shows a volcano plot of RNA sequencing comparing DIPG cells isolated from the pons and from an SVZ site of spread from SU-DIPG-XIII. X-axis represents log 2(fold change) of frontal lobe over pons; y-axis shows −log 10 (Benjamini-Hochberg adjusted p-value) from differential testing. Points in red represent those with adjusted p-values less than 0.1. FIG. 8D show GO biological processes significantly overexpressed in the frontal lobe compared to the pontine culture of SU-DIPG-XIII. P-values shown are Bonferroni adjusted. FIGS. 8E-8H show H&E of tumor in the lateral wall of the lateral ventricle SVZ in SU-DIPG-XVII (FIG. 8E), SU-DIPG-III (FIG. 8F), and SU-DIPG-VI (FIGS. 8G and 8H). Low magnification images are shown in the left panels: scale bar, 1 mm. High magnification images are shown in the right panels: scale bar, 50 μm. FIG. 8I shows pontine DIPG cells, which are found primarily in the hindbrain in orthotopic xenografts by bioluminescent IVIS imaging, compared to SVZ DIPG cells, which are found in the forebrain and hindbrain.

FIG. 9A shows cell proliferation of DIPG cells (fraction of Ki67$^+$ cells) when exposed to unconditioned or conditioned mNPC media. FIG. 9B shows that cell viability of DIPG cells by the CellTiter-Glo assay when exposed to unconditioned or conditioned mNPC media. FIG. 9C shows that DIPG cells invade less toward murine neuron conditioned media compared to SVZ mNPC CM. All experiments performed with n=3 replicates/wells (FIGS. 9A, 9C) or n=4 replicates/wells (FIG. 9B) in SU-DIPG-XIII FL cells and analyzed by one-way ANOVA with Tukey post hoc adjustment for multiple comparisons. Data shown as mean±SEM. ***$p<0.001$.

FIG. 10A shows that DIPG cells invade differentially toward various combinations of the eight candidate recombinant proteins. The combination of PTN, SPARC, SPARCL1, and HSP90B most closely replicates the invasion-promoting effect toward SVZ hNPC CM. FIG. 10B shows an estimation of the concentration of PTN, SPARC, SPARCL1, and HSP90B in SVZ hNPC CM by Western blot and ImageJ. FIG. 10C shows that the combination of PTN, SPARC, SPARCL1, and HSP90B is sufficient for DIPG invasion at 100 nM as well as with each factor at its estimated concentration in the conditioned media. FIG. 10D shows that CHL-1 melanoma cells invade similarly toward unconditioned hNPC media, SVZ hNPC CM, and the combination of PTN, SPARC, SPARCL1, and HSP90B. Experiments performed with n=3 replicates/wells in SU-DIPG-XIII FL cells (FIGS. 10A, 10C) or in CHL-1 melanoma cells (FIG. 10D) and analyzed by one-way ANOVA with Tukey post hoc adjustment for multiple comparisons. Data shown as mean±SEM. *$p<0.05$, **$p<0.01$.

FIG. 12A shows that DIPG cells invade less toward SVZ hNPC CM after immunodepletion of any one of the four proteins, with or without add back of the other three proteins. n=3 replicates/wells in SU-DIPG-XIII FL cells and analyzed by one-way ANOVA with Tukey post hoc adjustment for multiple comparisons. FIG. 12B shows that tumor engraftment was equivalent in mice that received injections of shRNA lentivirus targeting Pin into the SVZ, compared to a scrambled shRNA control. In vivo experiments were performed with n=5 mice per group. Bioluminescent flux measurements were analyzed by unpaired, two-tailed Mann-Whitney test. Each data point=one mouse. FIG. 12C shows that gene expression of the PTN receptor PTPRZ1 in DIPG primary tissue and cultures from published RNA-seq datasets and the present RNA-seq data from SU-DIPG-XIII (Grasso et al., 2015; Nagaraja et al., 2017). RNA-seq of the primary tissue was performed with one replicate. RNA-seq of the cell cultures were performed with two replicates. FIG. 12D shows that exposure of DIPG cells to shRNA lentivirus targeting PTPRZ1 achieved effective knock down of PTPRZ1 gene expression as measured by qPCR, and of PTPRZ protein levels as measured by Western blot, compared to a scrambled shRNA control or no shRNA exposure. qPCR experiments performed with n=3 wells of cells and analyzed by one-way ANOVA with Tukey post hoc adjustment for multiple comparisons. FIG. 12E shows that knockdown of the PTN receptor PTPRZ1 in SU-DIPG-XIII FL cells resulted in a decrease in baseline DIPG invasion toward unconditioned hNPC media. n=3 replicates/wells in SU-DIPG-XIII FL cells expressing PTPRZ1 or scrambled shRNA and analyzed by unpaired, two-tailed Student's t-test. FIG. 12F shows that DIPG cells with knockdown of PTPRZ1 had a mild decrease in cell viability by the Cell-Titer-Glo assay compared to a scrambled control or no shRNA exposure. Cell viability was measured in base media without growth factors. n=4 replicates/wells in SU-DIPG-XIII FL cells expressing PTPRZ1, scrambled, or no shRNA and analyzed by one-way ANOVA with Tukey post hoc adjustment for multiple comparisons. FIG. 12G shows that knockdown of PTPRZ1 partially abrogates DIPG invasion toward SVZ hNPC CM or the PTN complex, compared to a scrambled control. n=3 replicates/wells in SU-DIPG-XIII FL cells expressing PTPRZ1 or scrambled shRNA and analyzed by unpaired, two-tailed Student's t-tests for comparison between PTPRZ1 knockdown cells or scrambled shRNA control cells. FIGS. 12H and 12I show that DIPG cells with knockdown of PTPRZ1 exhibited 10-fold decreased total tumor size indicating decreased engraftment (FIG. 12H), but similar tumor growth over time compared to scrambled shRNA control cells when orthotopically xenografted into mice (FIG. 12I). FIG. 12J shows that fewer DIPG cells with knockdown of PTPRZ1 invaded the SVZ when orthotopically xenografted into mice, compared to scrambled shRNA control cells. In vivo experiments were performed with n=8 mice per group. Bioluminescent flux measurements were analyzed by unpaired, two-tailed Mann-Whitney test for engraftment (FIG. 12H) or unpaired, two-tailed Student's t-test for growth (FIG. 12I). Stereological cell counts at 8 weeks following xenograft were analyzed by unpaired, two-tailed Mann-Whitney test (FIG. 12J). Each data point=one mouse. Data shown as mean±SEM. *p<0.05, p<0.01, *p<0.001.

FIG. 13A shows that treatment of DIPG cells with an HSP90 inhibitor, 17-AAG, resulted in decreased invasion toward SVZ hNPC CM at high doses. FIG. 13B shows cell viability of DIPG cells treated with increasing doses of 17-AAG, by the CellTiter-Glo assay. In vitro experiments performed with n=3 replicates/wells (FIG. 13A) or n=4 replicates/wells (FIG. 13B) in SU-DIPG-XIII FL cells and analyzed by one-way ANOVA with Tukey post hoc adjustment for multiple comparisons. FIG. 13C shows that orthotopically xenografted mice that were treated with 17-AAG had no difference in the number of DIPG cells invading the SVZ compared to a vehicle treatment control. In vivo experiments were performed with n=8 mice per group. Stereological cell counts at 8 weeks following xenograft were analyzed by unpaired, two-tailed Student's t-test. Each data point=one mouse. FIG. 13D shows that tumor engraftment was equivalent in mice that received injections of shRNA lentivirus targeting HSP90B1 into the SVZ, compared to a scrambled shRNA control. FIGS. 13E and 13F show that fewer orthotopically xenografted GFP+ HNA+ SU-DIPG-XIII FL cells invaded the SVZ, defined as a 200 µm-wide region adjacent to the lateral ventricles (outlined in dashed white lines), when sh-HSP90B1 lentivirus (right), compared to a scrambled shRNA control (left), was injected into the SVZ. White filled arrowheads denote areas of strong HSP90B expression in the SVZ (left); open arrowheads denote similar regions with low HSP90B expression after knockdown (right). Scale bar, 200 µm. Control data are from the same mice as in FIGS. 6C and 6E; these knockdown experiments were run in parallel with a common control. In vivo experiments (FIGS. 13D-13F) were performed with n=5 mice per group. Bioluminescent flux measurements were analyzed by unpaired, two-tailed Mann-Whitney test (FIG. 13D). Stereological cell counts at 16 weeks following xenograft were analyzed by unpaired, two-tailed Student's t-test (FIG. 13F). Each data point=one mouse. Data shown as mean±SEM. p<0.01, *p<0.001.

FIG. 14A show that shRNA-mediated knock down of PTPRZ1 in DIPG cells resulted in decreased activation of RhoA and ROCK upon exposure of DIPG cells to SVZ hNPC CM or to the PTN complex, compared to a scrambled shRNA control. n=3 replicates/wells in SU-DIPG-XIII FL cells expressing PTPRZ1 or scrambled shRNA and analyzed by unpaired, two-tailed Student's t-tests for comparison between PTPRZ1 knockdown cells or scrambled shRNA control cells. FIGS. 14B and 14C show that treatment of DIPG cells with two ROCK inhibitors: GSK 429286 (FIG. 14B) or GSK 269962A (FIG. 14C) do not affect cell viability at sub-µM concentrations. All experiments performed with n=4 replicates/wells in SU-DIPG-XIII FL cells and analyzed by one-way ANOVA with Tukey post hoc adjustment for multiple comparisons. Data shown as mean±SEM. *p<0.05, p<0.01, *p<0.001.

DETAILED DESCRIPTION

Figure 1A:
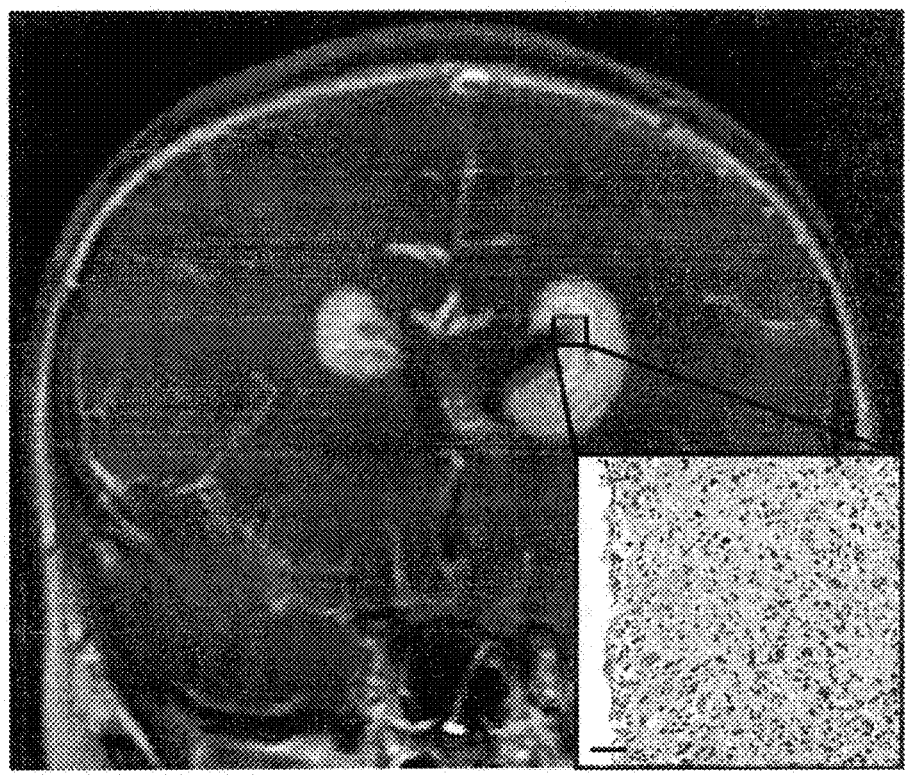
FIGS. 1A-1G show that DIPG cells, isolated from an SVZ site of spread, invade to the cerebrum and SVZ.
Figure 1B:
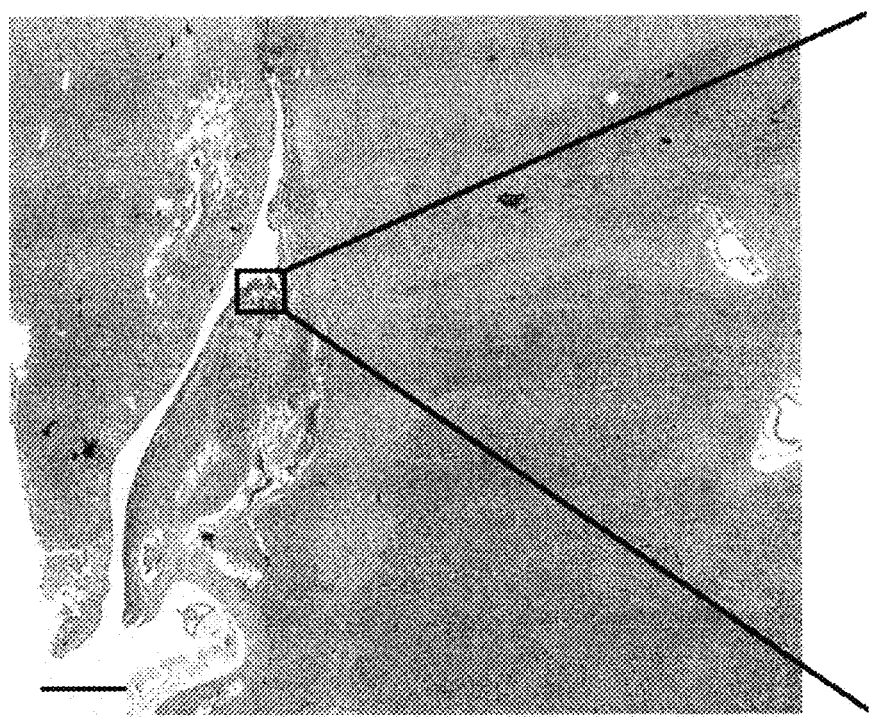
Figure 1C:
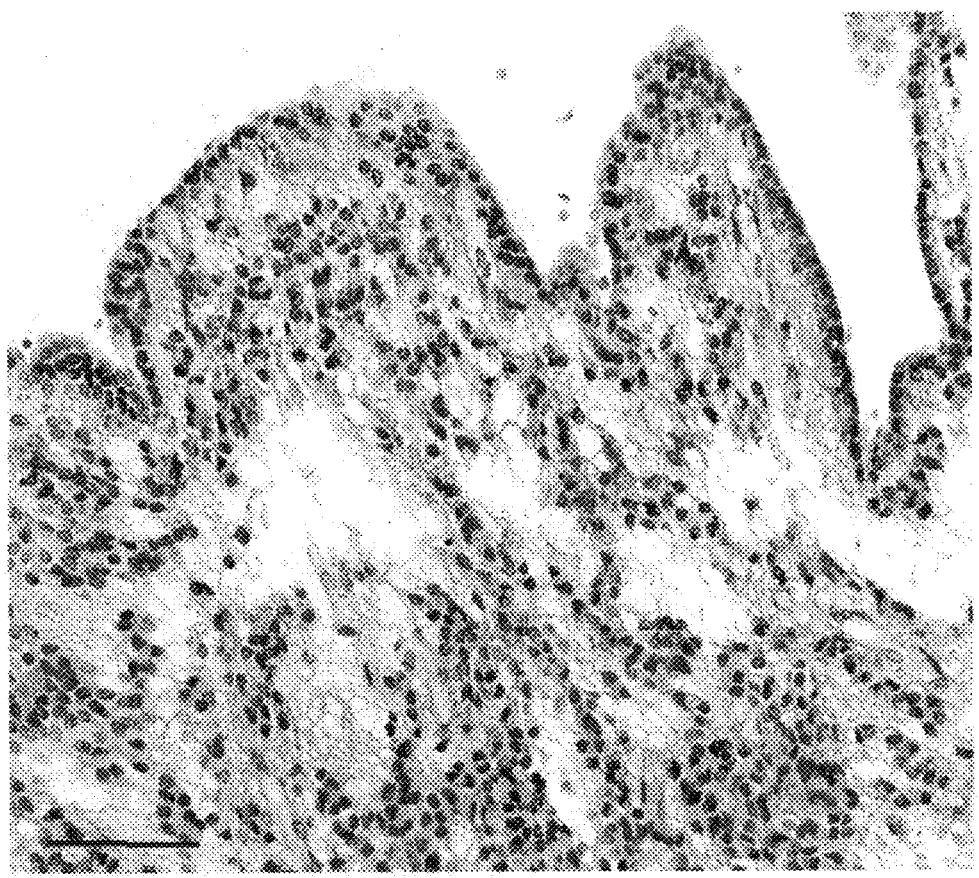

The practice of the present invention will employ, unless otherwise indicated, conventional methods of medicine, pharmacology, chemistry, biochemistry, molecular biology and recombinant DNA techniques, and immunology, within the skill of the art. Such techniques are explained fully in the literature. See, e.g., *Gliomas*, Volume 134 (Handbook of Clinical Neurology, M. S. Berger and M. Weller eds., Elsevier, 2016); *Tumors of the Central Nervous System*, Volume 14: *Glioma, Meningioma, Neuroblastoma, and Spinal Tumors* (M. A. Hayat ed., Springer, 2015); *Glioma Cell Biology* (A. Sedo and R. Mentlein eds., Springer, 2014); R. A. Weinberg *The Biology of Cancer* (Garland Science, 2$^{nd}$ edition, 2013); *siRNA and miRNA Gene Silencing: From Bench to Bedside* (Methods in Molecular Biology, M. Sioud ed., Humana Press, 2009); *RNA Interference* (Current Topics in Microbiology and Immunology, P. J. Paddison and P. K. Vogt eds., Springer, 1$^{st}$ edition, 2008); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Labora-* tory Manual (3rd Edition, 2001); Methods In Enzymology (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes a mixture of two or more cells, and the like.

The term "about," particularly in reference to a given quantity, is meant to encompass deviations of plus or minus five percent.

The term "inhibitory nucleic acid" includes nucleic acids, polynucleotides, and oligonucleotides that inhibit expression of one or more genes selected from the group consisting of PTN, HSP90B, SPARC, SPARCL1, and PTPRZ. Examples of inhibitory nucleic acids include short hairpin RNAs (shRNAs), small interfering RNAs (siRNAs), microRNAs (miRNAs), and anti-sense nucleic acids.

As used herein, the terms "microRNA," "miRNA," "mature microRNA," and "mature miRNA" refer to a non-coding single-stranded RNA molecule that is about 19 to about 25 nucleotides in length (including about 19, about 20, about 21, about 22, about 23, about 24, and about 25 nucleotides) that effectively reduces the expression level of target polynucleotides and polypeptides through the RNA interference pathway (i.e., through association with the RNA-induced silencing complex (RISC) and subsequent degradation of target mRNA or translational inhibition). The term "microRNA" refers to both endogenous miRNAs and artificial miRNAs that include single-stranded RNA molecules with sequences of about 19-25 nucleotides in length other than those found in endogenous miRNAs that effectively reduce the expression of target polynucleotides through RNA interference.

As used herein, the term "small interfering RNA" or "siRNA" refer to double-stranded RNA molecules, comprising a sense strand and an antisense strand, having sufficient complementarity to one another to form a duplex. Such sense and antisense strands each have a region of complementarity ranging, for example, from about 10 to about 30 contiguous nucleotides that base pair sufficiently to form a duplex or double-stranded siRNA. Such siRNAs are able to specifically interfere with the expression of a gene by triggering the RNAi machinery (e.g., RISC) of a cell to remove RNA transcripts having identical or homologous sequences to the siRNA sequence. As described herein, the sense and antisense strands of an siRNA may each consist of only complementary regions, or one or both strands may comprise additional sequences, including non-complementary sequences, such as 5' or 3' overhangs. An overhang may be of any length of nonhomologous residues, for example, 2, 3, 4, 5, 6, 7, 8, 9, 10, 11, 12, 13, 14, 15, 16 or more nucleotides. In addition, siRNAs may have other modifications, such as, for example, substituted or modified nucleotides or other sequences, which contribute to either the stability of the siRNA, its delivery to a cell or tissue, or its potency in triggering RNAi. It is to be understood that the terms "strand" and "oligonucleotide" may be used interchangeably in reference to the sense and antisense strands of siRNA compositions.

As used herein, the term "small hairpin RNA" or "shRNA" refers to an RNA sequence comprising a double-stranded stem region and a loop region at one end forming a hairpin loop. The double-stranded region is typically about 19 nucleotides to about 30 nucleotides in length on each side of the stem, and the loop region is typically about three to about twelve nucleotides in length. The shRNA may include 3'- or 5'-terminal single-stranded overhangs. An overhang may be of any length of nonhomologous residues, for example, 2, 3, 4, 5, 6, 7, 8, 9, 10, 11, 12, 13, 14, 15, 16 or more nucleotides. In addition, such shRNAs may have other modifications, such as, for example, substituted or modified nucleotides or other sequences, which contribute to either the stability of the shRNA, its delivery to a cell or tissue, or its potency in triggering RNAi. In some cases, the shRNA may be derived from an siRNA, the shRNA comprising the sense strand and antisense strand of the siRNA connected by a loop (see, e.g., Example 1 describing exemplary shRNAs).

A "target site" or "target sequence" is the nucleic acid sequence recognized (i.e., sufficiently complementary for hybridization) by an inhibitory nucleic acid. A single target site typically has about six to about ten nucleotides. The target site may be located within the 3' UTR, 5' UTR, or the coding region of a mRNA.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

"Administering" an inhibitory nucleic acid (e.g., miRNA, siRNA, shRNA, or anti-sense nucleic acid) or an expression vector or recombinant nucleic acid encoding an inhibitory nucleic acid to a cell comprises transducing, transfecting, electroporating, translocating, fusing, phagocytosing, shooting or ballistic methods, etc., i.e., any means by which a nucleic acid can be transported across a cell membrane.

The term "downregulating expression" refers to reduced expression of a mRNA or protein after administering or expressing an amount of an inhibitory nucleic acid (e.g., miRNA, siRNA, shRNA, or anti-sense nucleic acid). An inhibitory nucleic acid may downregulate expression, for example, by reducing translation of the target mRNA into protein, for example, through mRNA cleavage or through direct inhibition of translation. The reduction in expression of the target mRNA or the corresponding protein is commonly referred to as "knockdown." Downregulation or knockdown of expression may be complete or partial (i.e., all expression, some expression, or most expression of the target mRNA or protein is blocked by an inhibitory nucleic acid). For example, an inhibitory nucleic acid may reduce the expression of a mRNA or protein by 25%-100%, 30%-90%, 40%-80%, 50%-75%, or any amount in between these ranges, including at least 25%, 30%, 40%, 50%, 60%, 70%, 80%, or 90%, as compared to native or control levels. Downregulation of a target mRNA or protein may be the result of administering a single inhibitory nucleic acid or multiple (i.e., two or more) inhibitory nucleic acids, or vectors encoding them.

By "selectively binds" is meant that the molecule binds preferentially to the target of interest or binds with greater affinity to the target than to other molecules. For example, an inhibitory nucleic acid (e.g., miRNA, siRNA, shRNA, or anti-sense nucleic acid) will bind to a substantially complementary sequence and not to unrelated sequences. An inhibitory nucleic acid that selectively binds to a particular target mRNA will selectively downregulate expression of that target mRNA, that is, the expression of the target mRNA will be reduced to a greater extent than other mRNAs.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The terms "hybridize" and "hybridization" refer to formation of complexes between nucleotide sequences which are sufficiently complementary to form complexes via Watson-Crick base pairing.

As used herein, the terms "complementary" or "complementarity" refers to nucleic acids that are able to form base pairs with one another. Base pairs are typically formed by hydrogen bonds between nucleotide units in an anti-parallel orientation between polynucleotide strands. Complementary polynucleotide strands can base pair in a Watson-Crick manner (e.g., A to T, A to U, C to G), or in any other manner that allows for the formation of duplexes. As persons skilled in the art are aware, when using RNA as opposed to DNA, uracil (U) rather than thymine (T) is the base that is considered to be complementary to adenosine. However, when a uracil is denoted in the context of the present invention, the ability to substitute a thymine is implied, unless otherwise stated. "Complementarity" may exist between two RNA strands, two DNA strands, or between a RNA strand and a DNA strand. It is generally understood that two or more polynucleotides may be "complementary" and able to form a duplex despite having less than perfect or less than 100% complementarity. Two sequences are "perfectly complementary" or "100% complementary" if at least a contiguous portion of each polynucleotide sequence, comprising a region of complementarity, perfectly base pairs with the other polynucleotide without any mismatches or interruptions within such region. Two or more sequences are considered "perfectly complementary" or "100% complementary" even if either or both polynucleotides contain additional non-complementary sequences as long as the contiguous region of complementarity within each polynucleotide is able to perfectly hybridize with the other. "Less than perfect" complementarity refers to situations where less than all of the contiguous nucleotides within such region of complementarity are able to base pair with each other. Determining the percentage of complementarity between two polynucleotide sequences is a matter of ordinary skill in the art. For purposes of RNAi, sense and antisense strands of an siRNA or sense and antisense sequences of a shRNA composition may be deemed "complementary" if they have sufficient base-pairing to form a duplex (i.e., they hybridize with each other at a physiological temperature). The antisense (guide) strand of an siRNA or shRNA directs RNA-induced silencing complex (RISC) to mRNA that has a complementary sequence.

The term "hairpin" and "stem-loop" can be used interchangeably and refer to stem-loop structures. The stem results from two sequences of nucleic acid or modified nucleic acid annealing together to generate a duplex. The loop lies between the two strands comprising the stem.

The term "loop" refers to the part of the stem-loop between the two homologous regions (the stem) that can loop around to allow base-pairing of the two homologous regions. The loop can be composed of nucleic acid (e.g., DNA or RNA) or non-nucleic acid material(s), referred to herein as nucleotide or non-nucleotide loops. A non-nucleotide loop can also be situated at the end of a nucleotide molecule with or without a stem structure.

The term "sense RNA" refers to an RNA sequence corresponding to all or a portion of a coding sequence of a gene or all or a portion of a plus (+) strand or mRNA sequence generated from a gene, or an RNA sequence homologous thereto.

The term "antisense strand" refers to an RNA sequence corresponding to all or a portion of a template sequence of a gene, or a sequence homologous thereto, or a minus (−) strand or all or a portion of a sequence complementary to a mRNA sequence generated from a gene.

The term "transfection" is used to refer to the uptake of foreign DNA or RNA by a cell. A cell has been "transfected" when exogenous DNA or RNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA or RNA moieties into suitable host cells. The term refers to both stable and transient uptake of the genetic material, and includes uptake, for example, of inhibitory nucleic acids, such as microRNA, siRNA, shRNA, or antisense nucleic acids.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include post-expression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as catalytic activity, ligand binding activity, regulatory activity, degron protein degradation signaling, or fluorescence characteristics.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include glioma tumors in the brain or spine.

The term "glioma" includes any type of glioma, including but not limited to, ependymomas, astrocytomas, oligodendrogliomas, brainstem gliomas, optic nerve gliomas, and mixed gliomas, such as oligoastrocytomas containing cells from different types of glia. Further, the term includes supratentorial, infratentorial, and pontine gliomas and gliomas of any stage or grade, including low-grade gliomas (grades I and II) and high-grade gliomas (grades III and IV). Examples of gliomas include DIPG and its various subtypes (e.g., H3.3K27M mutant DIPG and H3.1 K27M mutant DIPG subtypes), adult glioblastoma, adult anaplastic oligodendroglioma, and pediatric spinal cord high-grade glioma.

An "effective amount" of an inhibitor of pleiotrophin signaling (e.g., an inhibitory nucleic acid, such as an shRNA, siRNA, miRNA, or antisense nucleic acid, a ribozyme, or a small molecule inhibitor) is an amount sufficient to effect beneficial or desired results, such as an amount that inhibits expression of one or more genes selected from the group consisting of PTN, HSP90B, SPARC, SPARCL1, and PTPRZ and/or interferes with assembly of a chemoattractant complex thereby reducing glioma invasion toward the brain subventricular zone. Additionally, an effective amount of an inhibitor of pleiotrophin signaling may inhibit pleiotrophin signaling through protein tyrosine phosphatase receptor type ζ and/or reduce activation of RhoA and Rho kinase (ROCK). An effective amount can be administered in one or more administrations, applications, or dosages.

The term "survival" as used herein means the time from the first dose of an inhibitor of pleiotrophin signaling to the time of death.

By "anti-tumor activity" is intended a reduction in the rate of cell proliferation, and hence a decline in growth rate of an existing tumor (e.g., glioma tumor) or in a tumor that arises during therapy, and/or destruction of existing anaplastic or neoplastic cells or newly formed anaplastic or neoplastic cells, and hence a decrease in the overall size of a tumor during therapy. Such activity can be assessed using animal models.

By "therapeutically effective dose or amount" of an inhibitor of pleiotrophin signaling (e.g., an inhibitory nucleic acid, such as an shRNA, siRNA, miRNA, or antisense nucleic acid, a ribozyme, or a small molecule inhibitor) is intended an amount that when administered in combination brings about a positive therapeutic response with respect to treatment of an individual for glioma. Of particular interest is an amount of the inhibitor of pleiotrophin signaling that provides anti-tumor activity, as defined herein. By "positive therapeutic response" is intended the individual undergoing treatment according to the invention exhibits an improvement in one or more symptoms of the glioma for which the individual is undergoing therapy. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease, determined by 2 assessments at least 4 weeks apart.

The term "partial response" (PR) as used herein means a 50% or greater reduction from baseline in the sum of the products of the longest perpendicular diameters of all measurable disease without progression of evaluable disease and without evidence of any new lesions as determined by at least two consecutive assessments at least four weeks apart. Assessments should show a partial decrease in the size of lytic lesions, recalcifications of lytic lesions, or decreased density of blastic lesions.

By "isolated" when referring to a polynucleotide, such as a mRNA, inhibitory nucleic acid (e.g., shRNA, siRNA, miRNA, or antisense nucleic acid), or other nucleic acid is meant that the indicated molecule is present in the substantial absence of other biological macromolecules of the same type. Thus, an "isolated shRNA, siRNA, miRNA, or antisense nucleic acid" refers to a polynucleotide molecule, which is substantially free of other polynucleotide molecules, e.g., other shRNA, siRNA, miRNA, or antisense nucleic acid molecules that do not target the same nucleotide sequence; however, the molecule may include some additional bases or moieties which do not deleteriously affect the basic characteristics of the composition.

"Substantially purified" generally refers to isolation of a substance (compound, nucleic acid, polynucleotide, oligonucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

The term "transfection" is used to refer to the uptake of foreign DNA or RNA by a cell. A cell has been "transfected" when exogenous DNA or RNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA or RNA moieties into suitable host cells. The term refers to both stable and transient uptake of the genetic material, and includes uptake, for example, of recombinant nucleic acids encoding fusion proteins.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

"Operably linked" refers to an arrangement of elements wherein the components so described are configured so as to perform their usual function. For example, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant" refers to biologically active derivatives of the reference molecule that retain desired activity, such as the ability of an inhibitor to cause RNA interference (RNAi) or inhibit pleiotrophin formation of a chemoattractant complex or inhibit binding of pleiotrophin to protein tyrosine phosphatase receptor type $\zeta$. In general, the term "variant" refers to molecules having a native sequence and structure with one or more additions, substitutions (generally conservative in nature) and/or deletions, relative to the native molecule, so long as the modifications do not destroy biological activity and which are "substantially homologous" to the reference molecule. In general, the sequences of such variants will have a high degree of sequence homology to the reference sequence, e.g., sequence homology of more than 50%, generally more than 60%-70%, even more particularly 80%-85% or more, such as at least 90%-95% or more, when the two sequences are aligned.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The terms "subject" refers to a vertebrate subject, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that the neurite outgrowth-promoting factor, pleiotrophin, in complexes with SPARC, SPARCL1, and HSP90B, acts as a chemoattractant for homing glioma cells to the ventricle subventricular zone (SVZ). In particular, the inventors have shown that pleiotrophin expression is strongly enriched in the SVZ, and knockdown of expression of pleiotrophin or any of its binding partners (i.e., SPARC, SPARCL1, or HSP90B) reduces glioma invasion of the SVZ (Example 1). In addition, pleiotrophin activates Rho/ROCK signaling through binding to the protein tyrosine phosphatase receptor type ζ, which if inhibited, also decreases glioma invasion toward the SVZ.

In order to further an understanding of the invention, a more detailed discussion is provided below regarding methods of treating glioma with inhibitors that block pleiotrophin formation of chemoattractant complexes and activation of Rho/ROCK signaling to limit glioma invasion of the SVZ.

A. Inhibitors of Pleiotrophin Signaling

An inhibitor of pleiotrophin signaling is used to decrease or prevent glioma invasion of the subventricular zone. Such an inhibitor may decrease pleiotrophin formation of chemoattractant complexes with SPARC, SPARCL1, and HSP90B, and/or interfere with pleiotrophin binding to tyrosine phosphatase receptor type ζ and activation of Rho/ROCK signaling. Inhibitors of pleiotrophin signaling can include, but are not limited to, inhibitory nucleic acids, such as miRNAs, siRNAs, shRNAs, and antisense nucleic acids, and ribozymes, and small molecule inhibitors.

In certain embodiments, the inhibitor of pleiotrophin signaling is an inhibitory nucleic acid that reduces expression of at least one gene selected from the group consisting of PTN, HSP90B, SPARC, SPARCL1, and PTPRZ. Various types of inhibitors for inhibiting nucleic acid function are well known in the art. See e.g., *Gene and Cell Therapy: Therapeutic Mechanisms and Strategies* (N. Smyth Templeton ed., CRC Press, 4$^{th}$ edition, 2015); *siRNA Design: Methods and Protocols* (Methods in Molecular Biology, D. J. Taxman ed., Humana Press, 2013); Antisense Drug Technology: Principles, Strategies, and Applications (S. T. Crooke ed., CRC Press, 2$^{nd}$ edition, 2007); International patent application WO/2012/018881; U.S. patent application 2011/0251261; U.S. Pat. No. 6,713,457; Kole et al. (2012) Nat. Rev. Drug Discov. 11(2):125-40; Sanghvi (2011) Curr. Protoc. Nucleic Acid Chem. Chapter 4: Unit 4.1.1-22; herein incorporated by reference in their entireties. Inhibitory nucleic acids can be single stranded or double stranded polynucleotides and may contain one or more chemical modifications, such as, but not limited to, locked nucleic acids, peptide nucleic acids, sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages. In addition, inhibitory RNA molecules may have a "tail" covalently attached to their 3'-end and/or 5'-end, which may be used to stabilize the RNA inhibitory molecule or enhance cellular uptake. Such tails include, but are not limited to, intercalating groups, various kinds of reporter groups, and lipophilic groups attached to the 3' or 5' ends of the RNA molecules. In certain embodiments, the RNA inhibitory molecule is conjugated to cholesterol or acridine. See, for example, the following for descriptions of syntheses of 3'-cholesterol or 3'-acridine modified oligonucleotides: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993); herein incorporated by reference in their entireties. Additional lipophilic moieties that can be used, include, but are not limited to, oleyl, retinyl, and cholesteryl residues, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, $O_3$-(oleoyl)lithocholic acid, $O_3$-(oleoyl) cholenic acid, dimethoxytrityl, or phenoxazine. Additional compounds, and methods of use, are set out in US Patent Publication Nos. 2010/0076056, 2009/0247608 and 2009/0131360; herein incorporated by reference in their entireties.

In one embodiment, inhibition of pleiotrophin signaling is achieved by administering antisense nucleic acids targeting PTN, HSP90B, SPARC, SPARCL1, or PTPRZ, or any combination thereof. The antisense nucleic acids may be ribonucleotides or deoxyribonucleotides. Preferably, the antisense nucleic acids have at least one chemical modification. Antisense nucleic acids may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the anti sense nucleic acids may comprise peptide nucleic acids (PNAs), which contain a peptide-based backbone rather than a sugar-phosphate backbone. The antisense nucleic acids may contain one or more chemical modifications, including, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense nucleic acids are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense nucleic acids to enhance stability and improve efficacy, such as those described in U.S. Pat. No. 6,838,283, which is herein incorporated by reference in its entirety, are known in the art and are suitable for use in the methods of the invention. Antisense nucleic acids may comprise a sequence that is at least partially complementary to a PTN, HSP90B, SPARC, SPARCL1, or PTPRZ target sequence, e.g., at least about 75%, 80%, 85%, 90%, 91%, 92%, 93%, 94%, 95%, 96%, 97%, 98%, or 99% complementary to the PTN, HSP90B, SPARC, SPARCL1, or PTPRZ target sequence. In some embodiments, the antisense oligonucleotide may be substantially complementary to the PTN, HSP90B, SPARC, SPARCL1, or PTPRZ target sequence, that is, at least about 95%, 96%, 97%, 98%, or 99% complementary to a target polynucleotide sequence. In one embodiment, the antisense oligonucleotide comprises a sequence that is 100% complementary to the PTN, HSP90B, SPARC, SPARCL1, or PTPRZ target sequence.

In another embodiment, the inhibitor of pleiotrophin signaling is an inhibitory RNA molecule (e.g., a miRNA, a siRNA, a shRNA, a piRNA, or a snRNA) having a single-stranded or double-stranded region that is at least partially complementary to a PTN, HSP90B, SPARC, SPARCL1, or PTPRZ target sequence, e.g., about 75%, 80%, 85%, 90%, 91%, 92%, 93%, 94%, 95%, 96%, 97%, 98%, or 99% complementary to the PTN, HSP90B, SPARC, SPARCL1, or PTPRZ target sequence. In some embodiments, the inhibitory RNA comprises a sequence that is substantially complementary to the PTN, HSP90B, SPARC, SPARCL1, or PTPRZ target sequence, e.g., about 95%, 96%, 97%, 98%, or 99% complementary to a target polynucleotide sequence. In other embodiments, the inhibitory RNA molecule may contain a region that has 100% complementarity to the target sequence. In certain embodiments, the inhibitory RNA molecule is a double-stranded, small interfering RNA or a short hairpin RNA molecule (shRNA) comprising a stem-loop structure. In one embodiment, the inhibitor of pleiotrophin signaling is an shRNA comprising a nucleotide sequence selected from the group consisting of SEQ ID NOS:7-13, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the shRNA is capable of inhibiting expression of one or more genes selected from the group consisting of PTN, HSP90B, SPARC, SPARCL1, and PTPRZ.

In certain embodiments, the inhibitory RNA molecule comprises two complementary, single-stranded RNA molecules, such as an siRNA comprising sense and antisense strands. In other embodiments, the sense RNA sequence and the antisense RNA sequence may be encoded by a single molecule, such as an shRNA comprising two complementary sequences forming a "stem" (corresponding to sense and antisense strands) covalently linked by a single-stranded "hairpin" or loop sequence. The hairpin sequence may be from about 3 to about 12 nucleotides in length, including any length in between, such as 3, 4, 5, 6, 7, 8, 9, 10, 11, or 12 nucleotides in length. The loop can be at either end of the molecule; that is, the sense strand can be either 5' or 3' relative to the loop. In addition, a non-complementary duplex region (approximately one to six base pairs, for example, four CG base pairs) can be placed between the targeting duplex and the loop, for example to serve as a "CG clamp" to strengthen duplex formation.

In certain embodiments, the sense RNA strand or sequence of the siRNA or shRNA is 19 to 29 nucleotides in length or any length in between, such as 19, 20, 21, 22, 23, 24, 25, 26, 27, 28, or 29 nucleotides in length. Similarly, the antisense strand or sequence of the siRNA or shRNA may be 19 to 29 nucleotides in length or any length in between, such as 19, 20, 21, 22, 23, 24, 25, 26, 27, 28, or 29 nucleotides in length. The regions of complementarity in sense and antisense strands or sequences may be the same length. Alternatively, the sense and antisense strands may further contain non-complementary sequences, such as 3' or 5' overhangs or other non-complementary sequences that provide different functions for the siRNA or shRNA composition that do not contribute to base-pairing between the sense and antisense strands or sequences. Overhangs may include ribonucleotides, deoxyribonucleotides, or chemically modified nucleotides that, for example, promote enhanced nuclease resistance.

In certain embodiments, an siRNA or shRNA may comprise a 3' overhang of from 1 to about 6 nucleotides in length, such as an overhang of 1 to about 5 nucleotides in length, 1 to about 4 nucleotides in length, or 2 to 4 nucleotides in length, including any length within these ranges, such as 1, 2, 3, 4, or 5 nucleotides in length. Either one or both strands of an siRNA may comprise a 3' overhang. If both strands of the siRNA comprise 3' overhangs, the length of the overhangs may be the same or different for each strand. In one embodiment, the 3' overhang present on either one or both strands of the siRNA may be 2 nucleotides in length. For example, each strand of an siRNA may comprise a 3' overhang of dithymidylic acid ("TT") or diuridylic acid ("UU") or other effective dinucleotide combinations known in the art. The 3' terminus of an shRNA can have a non-target-complementary overhang of two or more nucleotides, for example, UU or dTdT; however, the overhangs can comprise any nucleotide including chemically modified nucleotides that, for example, promote enhanced nuclease resistance. In other embodiments, siRNAs or shRNAs comprise one or zero nucleotides overhanging at the 3' end.

In order to enhance stability of an siRNA or shRNA, 3' overhangs may be stabilized by including purine nucleotides, such as adenosine or guanosine nucleotides. Alternatively, substitution of pyrimidine nucleotides by modified analogues, e.g., substitution of uridine nucleotides in 3' overhangs with 2'-deoxythymidine, may be tolerated and not affect the efficiency of RNAi degradation. In particular, the absence of a 2'-hydroxyl in the 2'-deoxythymidine may significantly enhance the nuclease resistance of the 3' overhang.

Inhibitory RNA molecules may further comprise one or more chemical modifications, such as, but not limited to, locked nucleic acids, peptide nucleic acids, sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages. Additionally, an inhibitory RNA molecule may be conjugated to a lipophilic molecule (e.g., cholesterol or fatty acid) to facilitate cellular uptake. Although predominantly composed of ribonucleotides, siRNAs or shRNAs may also contain one or more deoxyribonucleotides in addition to ribonucleotides along the length of one or both strands or sequences to improve efficacy or stability. The 5' end of one or both strands or sequences of an siRNA or shRNA may also contain a phosphate group.

An "effective amount" of an inhibitor of pleiotrophin signaling (e.g., inhibitory nucleic acid such as a miRNA, siRNA, shRNA, or antisense nucleic acid, or a ribozyme or small molecule inhibitor) is an amount sufficient to effect beneficial or desired results, such as an amount that reduces pleiotrophin formation of chemoattractant complexes with SPARC, SPARCL1, and HSP90B and/or interferes with pleiotrophin activation of the tyrosine phosphatase receptor type ζ and Rho/ROCK signaling. In some embodiments, an inhibitor of pleiotrophin signaling reduces the amount and/or activity of pleiotrophin or complexes thereof (e.g., with HSP90B, SPARC, SPARCL1, and/or PTPRZ) by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%.

In certain embodiments, the invention includes compositions comprising one or more inhibitory nucleic acids (e.g. miRNAs, siRNAs, shRNAs, or antisense nucleic acids) capable of inhibiting expression of one or more genes selected from the group consisting of HSP90B, SPARC, SPARCL1, and PTPRZ. Such compositions may comprise partially purified RNA, substantially pure RNA, synthetic RNA, or recombinantly produced RNA, as well as altered RNA that differs from naturally-occurring RNA by the addition, deletion, substitution, synthesis, and/or modification of one or more nucleotides. Such modifications may include addition of non-nucleotide material, such as to the end(s) of the inhibitory nucleic acid or to one or more internal nucleotides of the inhibitory nucleic acid, including modifications that make the inhibitory nucleic acid more effective or resistant to nuclease digestion.

Knockdown can be assessed by measuring levels of the mRNA targeted by an inhibitory nucleic acid using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knockdown include RNA solution hybridization, nuclease protection, northern hybridization, gene expression monitoring with a microarray, antibody binding, radioimmunoassay, and fluorescence activated cell analysis.

In certain embodiments, the invention includes a method of inhibiting glioma tropism towards a brain subventricular zone in response to a chemoattractant complex, the method comprising administering to a subject in need thereof at least one inhibitory nucleic acid that inhibits expression of one or more genes selected from the group consisting of PTN, HSP90B, SPARC, and SPARCL1, wherein said at least one inhibitory nucleic acid is administered in an amount sufficient to interfere with assembly of the chemoattractant complex in the brain subventricular zone.

Inhibitors can be detectably labeled by well-known techniques. Detectable labels include, for example, radioactive isotopes, fluorescent labels, chemiluminescent labels, bioluminescent labels and enzyme labels. Such labeled inhibitors can be used to determine cellular uptake efficiency, quantitate binding of inhibitors at target sites, or visualize inhibitor localization.

In certain embodiments, an inhibitory nucleic acid is expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing the inhibitory nucleic acid comprises a promoter "operably linked" to a polynucleotide encoding the inhibitory nucleic acid. The phrase "operably linked" or "under transcriptional control" as used herein means that the promoter is in the correct location and orientation in relation to a polynucleotide to control the initiation of transcription by RNA polymerase and expression of the inhibitory nucleic acid. In certain embodiments, the recombinant polynucleotide comprises a first polynucleotide sequence encoding the sense strand of an siRNA and a second polynucleotide sequence encoding the antisense strand of an siRNA. In another embodiment, the recombinant polynucleotide comprises a polynucleotide sequence encoding an shRNA, including the sense sequence, antisense sequence, and hairpin loop of the shRNA.

A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Typical promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences include UTRs which include an Internal Ribosome Entry Site (IRES) present in the leader sequences of picornaviruses such as the encephalomyocarditis virus (EMCV) UTR (Jang et al. J. Virol. (1989) 63:1651-1660. Other picornavirus UTR sequences that will also find use in the present invention include the polio leader sequence and hepatitis A virus leader and the hepatitis C IRES.

In certain embodiments, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Fluorescent markers (e.g., GFP, EGFP, Dronpa, mCherry, mOrange, mPlum, Venus, YPet, phycoerythrin), or immunologic markers can also be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may be introduced into cells. In certain embodiments of the invention, the expression construct comprises a virus or engineered construct derived from a viral genome. A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference in their entireties). The ability of certain viruses to enter cells via receptor-mediated endocytosis, to integrate into host cell genomes and express viral genes stably and efficiently have made them attractive candidates for the transfer of foreign genes into mammalian cells.

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr. Pharm. Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mitterder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules of interest include those derived from the pox family of viruses, including vaccinia virus and avian poxvirus. By way of example, vaccinia virus recombinants expressing a nucleic acid molecule of interest (e.g., encoding miRNA, siRNA, shRNA, or antisense nucleic acid) can be constructed as follows. The DNA encoding the particular nucleic acid sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the nucleic acid molecules of interest. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos.

WO 02/099035, WO 02/080982, WO 01/81609, and WO 00/61772; herein incorporated by reference in their entireties.

A vaccinia-based infection/transfection system can be conveniently used to provide for inducible, transient expression of the polynucleotides of interest (e.g., encoding miRNA, siRNA, shRNA, or antisense nucleic acid) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA. The method provides for high level, transient, cytoplasmic production of large quantities of RNA. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of nucleic acids using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135, 855.

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include the use of calcium phosphate precipitation, DEAE-dextran, electroporation, direct microinjection, DNA-loaded liposomes, lipofectamine-DNA complexes, cell sonication, gene bombardment using high velocity microprojectiles, and receptor-mediated transfection (see, e.g., Graham and Van Der Eb (1973) Virology 52:456-467; Chen and Okayama (1987) Mol. Cell Biol. 7:2745-2752; Rippe et al. (1990) Mol. Cell Biol. 10:689-695; Gopal (1985) Mol. Cell Biol. 5:1188-1190; Tur-Kaspa et al. (1986) Mol. Cell. Biol. 6:716-718; Potter et al. (1984) Proc. Natl. Acad. Sci. USA 81:7161-7165); Harland and Weintraub (1985) J. Cell Biol. 101: 1094-1099); Nicolau and Sene (1982) Biochim. Biophys. Acta 721:185-190; Fraley et al. (1979) Proc. Natl. Acad. Sci. USA 76:3348-3352; Fechheimer et al. (1987) Proc Natl. Acad. Sci. USA 84:8463-8467; Yang et al. (1990) Proc. Natl. Acad. Sci. USA 87:9568-9572; Wu and Wu (1987) J. Biol. Chem. 262:4429-4432; Wu and Wu (1988) Biochemistry 27:887-892; herein incorporated by reference). Some of these techniques may be successfully adapted for in vivo or ex vivo use.

Once the expression construct has been delivered into the cell the nucleic acid encoding the inhibitory nucleic acid may be positioned and expressed at different sites. In certain embodiments, the nucleic acid encoding the inhibitory nucleic acid may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (Proc. Natl. Acad. Sci. USA (1984) 81:7529-7533) successfully injected polyomavirus DNA in the form of calcium phosphate precipitates into liver and spleen of adult and newborn mice demonstrating active viral replication and acute infection. Benvenisty and Neshif (Proc. Natl. Acad. Sci. USA (1986) 83:9551-9555) also demonstrated that direct intraperitoneal injection of calcium phosphate-precipitated plasmids results in expression of the transfected genes. It is envisioned that DNA encoding an inhibitory nucleic acid may also be transferred in a similar manner in vivo and express the inhibitory nucleic acid.

In still another embodiment, a naked DNA expression construct may be transferred into cells by particle bombardment. This method depends on the ability to accelerate DNA-coated microprojectiles to a high velocity allowing them to pierce cell membranes and enter cells without killing them (Klein et al. (1987) Nature 327:70-73). Several devices for accelerating small particles have been developed. One such device relies on a high voltage discharge to generate an electrical current, which in turn provides the motive force (Yang et al. (1990) Proc. Natl. Acad. Sci. USA 87:9568-9572). The microprojectiles may consist of biologically inert substances, such as tungsten or gold beads.

In a further embodiment, the expression construct may be delivered using liposomes. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991) Liver Diseases, Targeted Diagnosis and Therapy Using Specific Receptors and Ligands, Wu et al. (Eds.), Marcel Dekker, NY, 87-104). Also contemplated is the use of lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al. (1989) Science 243:375-378). In other embodiments, the liposome may be complexed or employed in conjunction with nuclear non-histone chromosomal proteins (HMG-I) (Kato et al. (1991) J. Biol. Chem. 266(6): 3361-3364). In yet further embodiments, the liposome may be complexed or employed in conjunction with both HVJ and HMG-I. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular inhibitory nucleic acid into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993) Adv. Drug Delivery Rev. 12:159-167).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin (see, e.g., Wu and Wu (1987), supra; Wagner et al. (1990) Proc. Natl. Acad. Sci. USA 87(9):3410-3414). Recently, a synthetic neoglycoprotein, which recognizes the same receptor as ASOR, has been used as a gene delivery vehicle (Ferkol et al. (1993) FASEB J. 7:1081-1091; Perales et al. (1994) Proc. Natl. Acad. Sci. USA 91(9):4086-4090), and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (Methods Enzymoi. (1987) 149:157-176) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes.

In a particular example, an oligonucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

The inhibitory nucleic acid (e.g., miRNA, siRNA, shRNA, or antisense nucleic acid) may comprise a detectable label in order to facilitate detection of binding of the inhibitory nucleic acid to a target nucleic acid. Detectable labels suitable for use in the present invention include any composition detectable by spectroscopic, photochemical, biochemical, immunochemical, electrical, optical, or chemical means. Useful labels in the present invention include biotin or other streptavidin-binding proteins for staining with labeled streptavidin conjugate, magnetic beads (e.g., Dynabeads), fluorescent dyes (e.g., green fluorescent protein, mCherry, cerulean fluorescent protein, phycoerythrin, YPet, fluorescein, Texas red, rhodamine, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. In addition, magnetic resonance imaging (MRI) contrast agents (e.g., gadodiamide, gadobenic acid, gadopentetic acid, gadoteridol, gadofosveset, gadoversetamide, gadoxetic acid), and computed tomography (CT) contrast agents (e.g., Diatrizoic acid, Metrizoic acid, Iodamide, Iotalamic acid, Ioxitalamic acid, Ioglicic acid, Acetrizoic acid, Iocarmic acid, Methiodal, Diodone, Metrizamide, Iohexol, Ioxaglic acid, Iopamidol, Iopromide, Iotrolan, Ioversol, Iopentol, Iodixanol, Iomeprol, Iobitridol, Ioxilan, Iodoxamic acid, Iotroxic acid, Ioglycamic acid, Adipiodone, Iobenzamic acid, Iopanoic acid, Iocetamic acid, Sodium iopodate, Tyropanoic acid, Calcium iopodate) are useful as labels in medical imaging. Patents teaching the use of such labels include U.S. Pat. Nos. 3,817,837; 3,850,752; 3,939,350; 3,996,345; 4,277,437; 4,275,149; 4,366,241; 5,798,092; 5,695,739; 5,733,528; and 5,888,576.

The present invention also encompasses pharmaceutical compositions comprising one or more inhibitory nucleic acids (e.g., miRNAs, siRNAs, shRNAs, or antisense nucleic acids) or recombinant polynucleotides or vectors encoding them and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the inhibitory nucleic acids (e.g., miRNAs, siRNAs, shRNAs, or antisense nucleic acids) or recombinant polynucleotides or vectors encoding them described herein. Commercially available fat emulsions that are suitable for delivering the nucleic acids of the invention to tissues, such as cardiac muscle tissue and smooth muscle tissue, include Intralipid, Liposyn, Liposyn II, Liposyn III, Nutrilipid, and other similar lipid emulsions. A preferred colloidal system for use as a delivery vehicle in vivo is a liposome (i.e., an artificial membrane vesicle). The preparation and use of such systems are well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO 03/093449, which are herein incorporated by reference in their entireties.

One will generally desire to employ appropriate salts and buffers to render delivery vehicles stable and allow for uptake by target cells. Buffers also will be employed when recombinant cells are introduced into a patient. Aqueous compositions of the present invention comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the nucleic acids of the compositions.

Compositions for use in the invention will comprise a therapeutically effective amount of at least one inhibitory nucleic acid (e.g., miRNA, siRNA, shRNA, or antisense nucleic acid) or recombinant polynucleotide or vector encoding an inhibitory nucleic acid. An "effective amount" of an inhibitory nucleic acid (e.g., miRNA, siRNA, shRNA, or antisense nucleic acid) or a recombinant polynucleotide or vector encoding an inhibitory nucleic acid is an amount sufficient to effect beneficial or desired results, such as an amount that downregulates expression of a target mRNA or protein (e.g., PTN, HSP90B, SPARC, SPARCL1, or PTPRZ). For an inhibitory nucleic acid (e.g., miRNA, siRNA, shRNA, or antisense nucleic acid), an effective amount may reduce translation or increase degradation of the mRNA targeted by the inhibitory nucleic acid. An effective amount can be administered in one or more administrations, applications or dosages. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards B. Administration At least one therapeutically effective dose of an inhibitor of pleiotrophin signaling will be administered. The inhibitor of pleiotrophin signaling may be an inhibitory nucleic acid, such as an antisense nucleic acid or inhibitory RNA molecule such as, a miRNA, siRNA, or shRNA, or a small molecule inhibitor. By "therapeutically effective dose or amount" of an inhibitor of pleiotrophin signaling is intended an amount that when administered brings about a positive therapeutic response with respect to treatment of an individual for glioma. Of particular interest is an amount that provides an anti-tumor effect, as defined herein. By "positive therapeutic response" is intended the individual undergoing the treatment according to the invention exhibits an improvement in one or more symptoms of the glioma for which the individual is undergoing therapy.

Thus, for example, a "positive therapeutic response" would be an improvement in the disease in association with the therapy, and/or an improvement in one or more symptoms of the disease in association with the therapy. Therefore, for example, a positive therapeutic response would refer to one or more of the following improvements in the disease: (1) reduction in tumor size; (2) reduction in the number of glioma cells; (3) inhibition (i.e., slowing to some extent, preferably halting) of tumor growth; (4) inhibition (i.e., slowing to some extent, preferably halting) of glioma cell infiltration into the brain and spine, particularly the SVZ; (5) inhibition (i.e., slowing to some extent, preferably halting) of tumor metastasis; and (6) some extent of relief from one or more symptoms associated with the glioma. Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as being a partial response. By "partial response" is intended a reduction of greater than 50% in the sum of the products of the perpendicular diameters of all measurable lesions when compared with pretreatment measurements.

The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. Generally, a therapeutically effective amount will range from about 0.50 mg to 5 grams NSAID daily, more preferably from about 5 mg to 2 grams daily, even more preferably from about 7 mg to 1.5 grams daily. Preferably, such doses are in the range of 10-600 mg four times a day (QID), 200-500 mg QID, 25-600 mg three times a day (TID), 25-50 mg TID, 50-100 mg TID, 50-200 mg TID, 300-600 mg TID, 200-400 mg TID, 200-600 mg TID, 100 to 700 mg twice daily (BID), 100-600 mg BID, 200-500 mg BID, or 200-300 mg BID.

In certain embodiments, multiple therapeutically effective doses of at least one inhibitor of pleiotrophin signaling (e.g., inhibitory nucleic acid such as miRNA, siRNA, shRNA, or anti-sense nucleic acid, or a small molecule inhibitor) and/or one or more other therapeutic agents for treating glioma, such as chemotherapeutic agents, anti-angiogenic agents, immunotherapeutic agents, or biologic agents will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, at least one inhibitor of pleiotrophin signaling and/or other therapeutic agents for treating glioma, will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

In other embodiments of the invention, the pharmaceutical composition comprising the agents, such as one or more inhibitors of pleiotrophin signaling and/or other therapeutic agents is a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The pharmaceutical compositions comprising one or more inhibitors of pleiotrophin signaling and/or other therapeutic agents for treating glioma may be administered using the same or different routes of administration in accordance with any medically acceptable method known in the art. Suitable routes of administration include parenteral administration, such as by injection, intracerebroventricularly, intraparenchymatously, intracephalically, intracerebrally, intracerebellarly, intracranially, intraneurally, intraspinally, subcutaneously, intraperitoneally, intramuscularly, intra-arterially, or intravenously. In certain embodiments, compositions are administered by stereotactic injection into the brain. Compositions may be injected directly into glioma lesions or into the arterial blood supply of a lesion. Additional formulations suitable for other modes of administration include oral and pulmonary formulations, suppositories, and transdermal formulations, aerosol, intranasal, and sustained release formulations.

Factors influencing the respective amount of the various compositions to be administered include, but are not limited to, the mode of administration, the frequency of administration (i.e., daily, or intermittent administration, such as twice- or thrice-weekly), the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of an agent is preferred with increasing weight of the subject undergoing therapy.

An inhibitor of pleiotrophin signaling can be administered prior to, concurrent with, or subsequent to other agents. If provided at the same time as other agents, one or more inhibitors of pleiotrophin signaling can be provided in the same or in a different composition. Thus, one or more inhibitors of pleiotrophin signaling and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising an inhibitor of pleiotrophin signaling and a dose of a pharmaceutical composition comprising at least one other agent, such as another anti-glioma drug or other medication, which in combination comprise a therapeutically effective dose, according to a particular dosing regimen. Similarly, one or more inhibitors of pleiotrophin signaling and one or more other anti-glioma therapeutic agents or other medications can be administered in at least one therapeutic dose. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Where a subject undergoing therapy in accordance with the previously mentioned dosing regimens exhibits a partial response, or a relapse following a prolonged period of remission, subsequent courses of therapy may be needed to achieve complete remission of the disease. Thus, subsequent to a period of time off from a first treatment period, a subject may receive one or more additional treatment periods of treatment with an inhibitor of pleiotrophin signaling. Such a period of time off between treatment periods is referred to herein as a time period of discontinuance. It is recognized that the length of the time period of discontinuance is dependent upon the degree of tumor response (i.e., complete versus partial) achieved with any prior treatment periods.

C. Kits

Any of the compositions described herein may be included in a kit. For example, at least one inhibitor of pleiotrophin signaling (e.g. an inhibitory nucleic such as an shRNA, siRNA, miRNA, or an antisense oligonucleotide, or a small molecule inhibitor) may be included in a kit. The kit may also include one or more transfection reagents to facilitate delivery of inhibitory nucleic acids to cells. Additionally, the kit may also include other anti-glioma therapeutic agents.

The components of the kit may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the inhibitor of pleiotrophin signaling or that protect against their degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include information on treating glioma as described herein and variations that can be implemented. A kit may also include utensils or devices for administering an inhibitor of pleiotrophin signaling by various administration routes, such as parenteral or catheter administration, or coated stent.

In certain embodiments, the kit comprises at least one shRNA capable of inhibiting expression of PTN, HSP90B, SPARC, SPARCL1, or PTPRZ.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Neural Precursor Cell-Derived Pleiotrophin Mediates Glioma Invasion of the Subventricular Zone Introduction In the present study, we sought to understand how and why diffuse intrinsic pontine glioma (DIPG) and other high-grade gliomas spread so frequently to the subventricular zone (SVZ), hypothesizing that this predilection could be mediated by interactions between the glioma cells and the neural precursor cells (NPCs) that normally reside in the SVZ.

Results

DIPG Cells Isolated from the SVZ Recapitulate Supratentorial Invasion in an Orthotopic Xenograft Model We had the opportunity to create a patient-derived culture of DIPG at the time of early postmortem autopsy from tumor in the pons and tumor in the SVZ (cultures designated SU-DIPG-XIII pons and SU-DIPG-XIII frontal lobe, also referred to as SVZ DIPG cells; FIG. 1A; please see FIGS. 8A-8D for genomic and gene expression characterizations of both cultures).

Figure 1D:
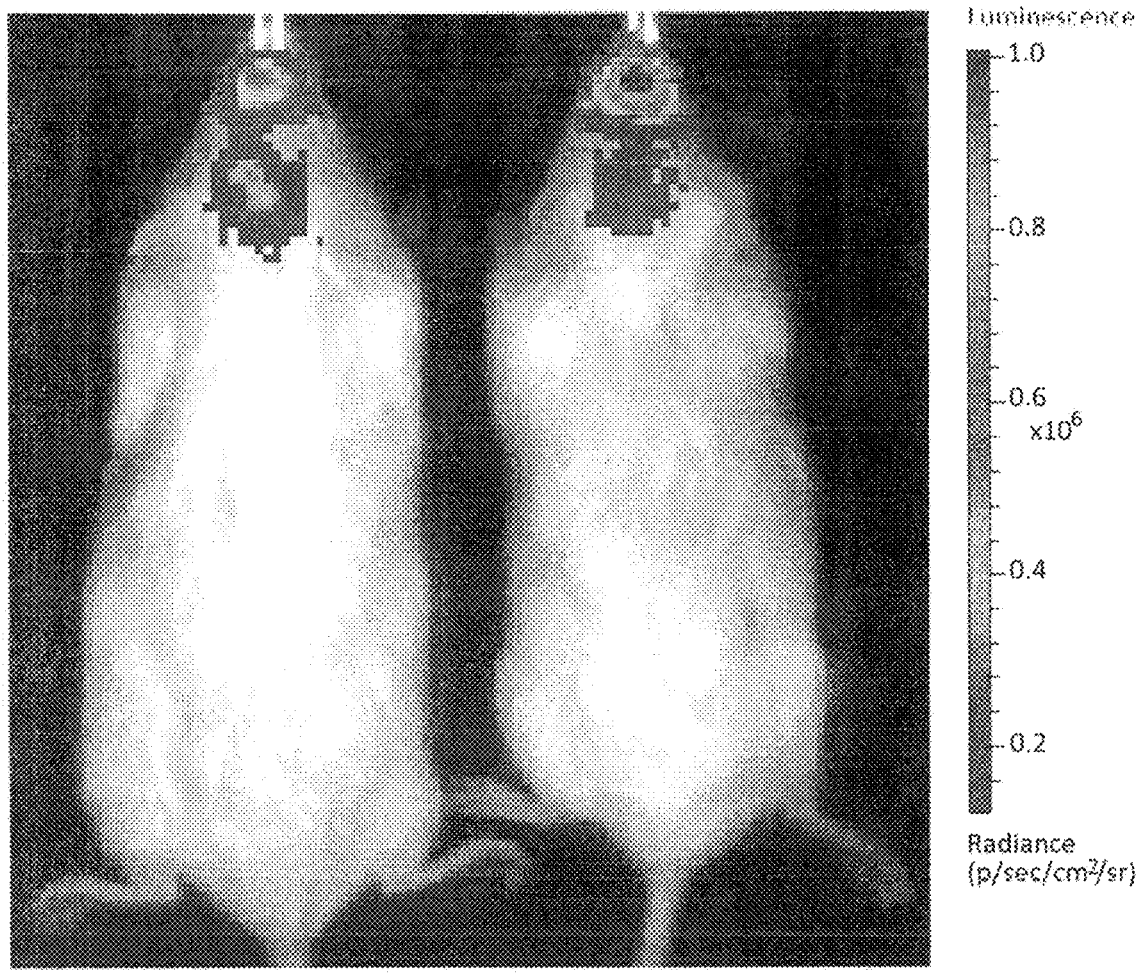
Figure 1E:
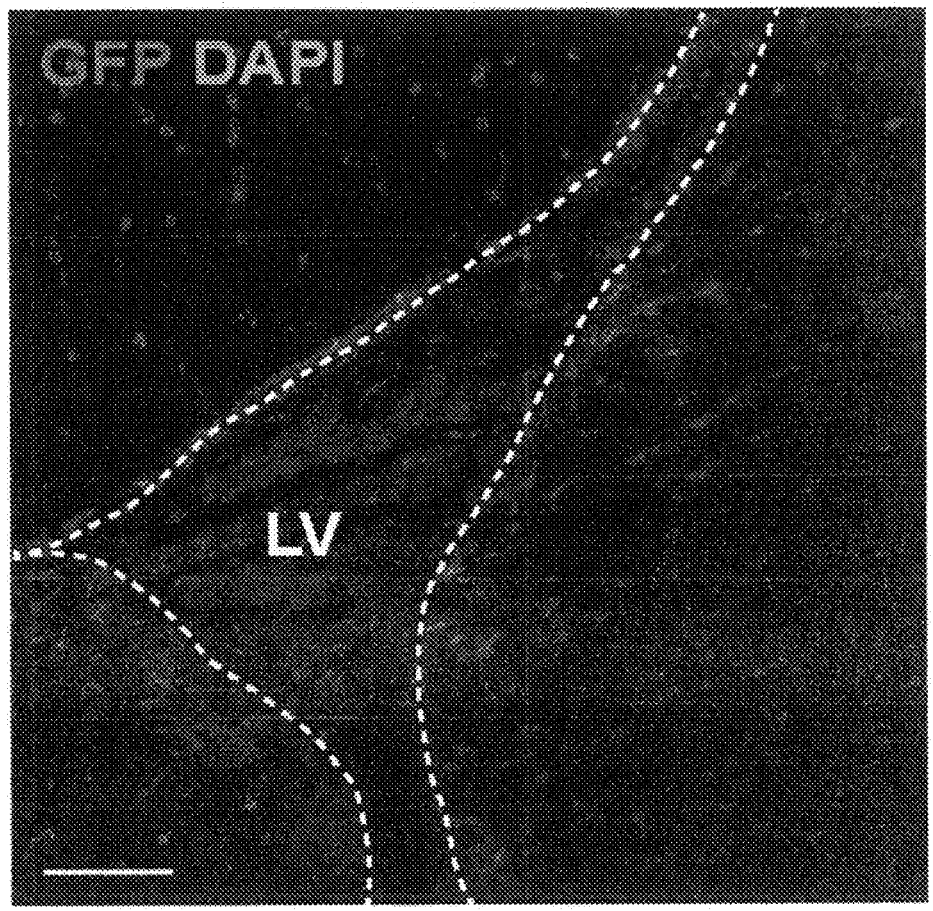
Figure 1F:
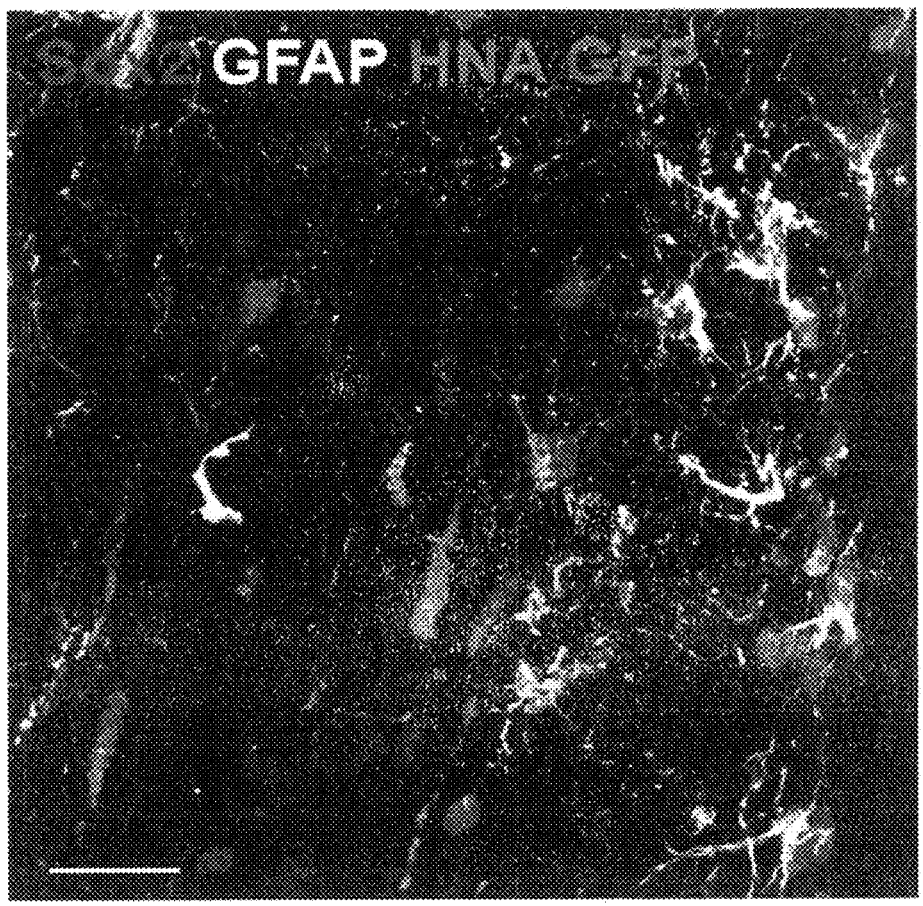
Figure 1G:
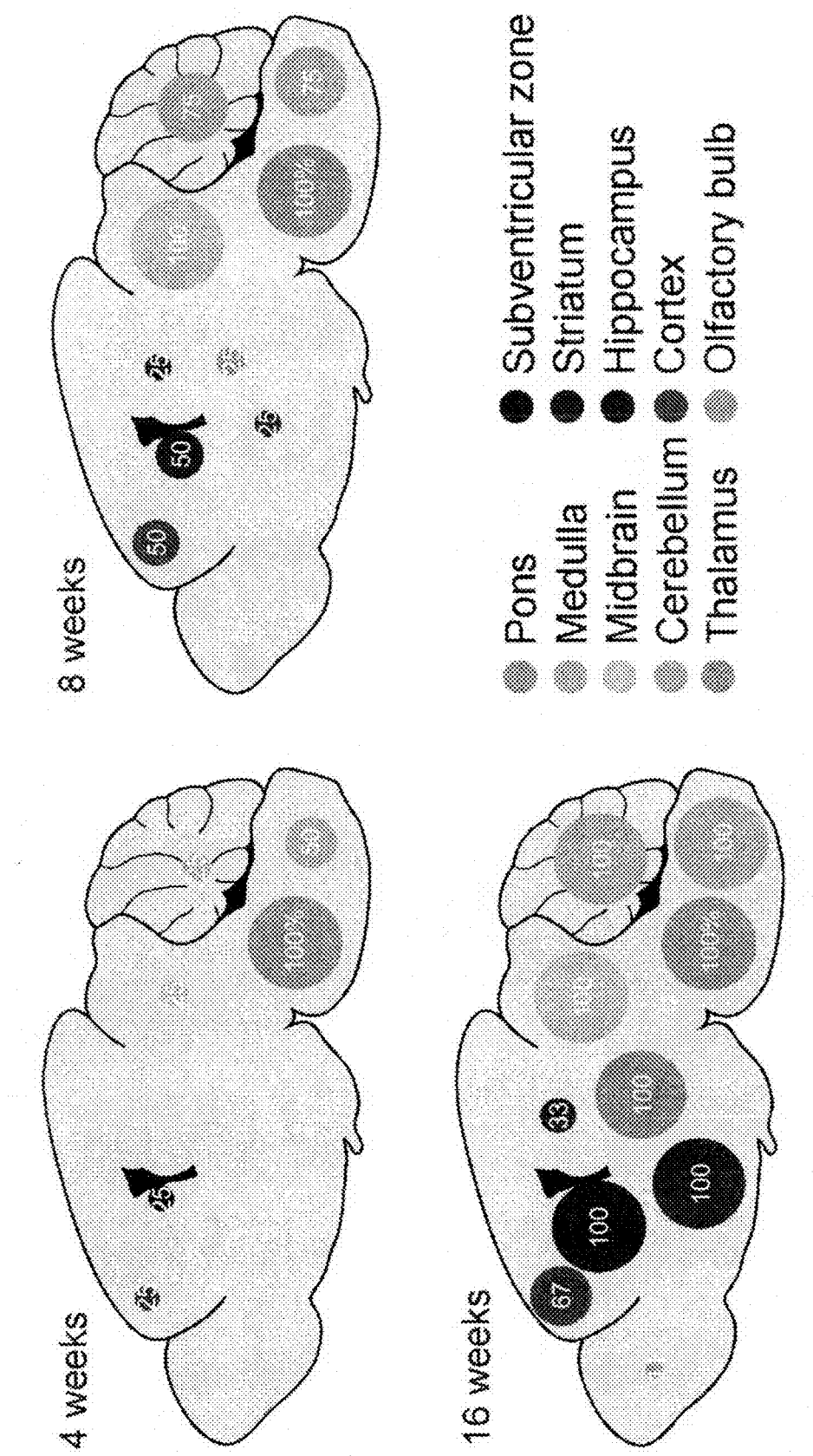
Figure 8A:
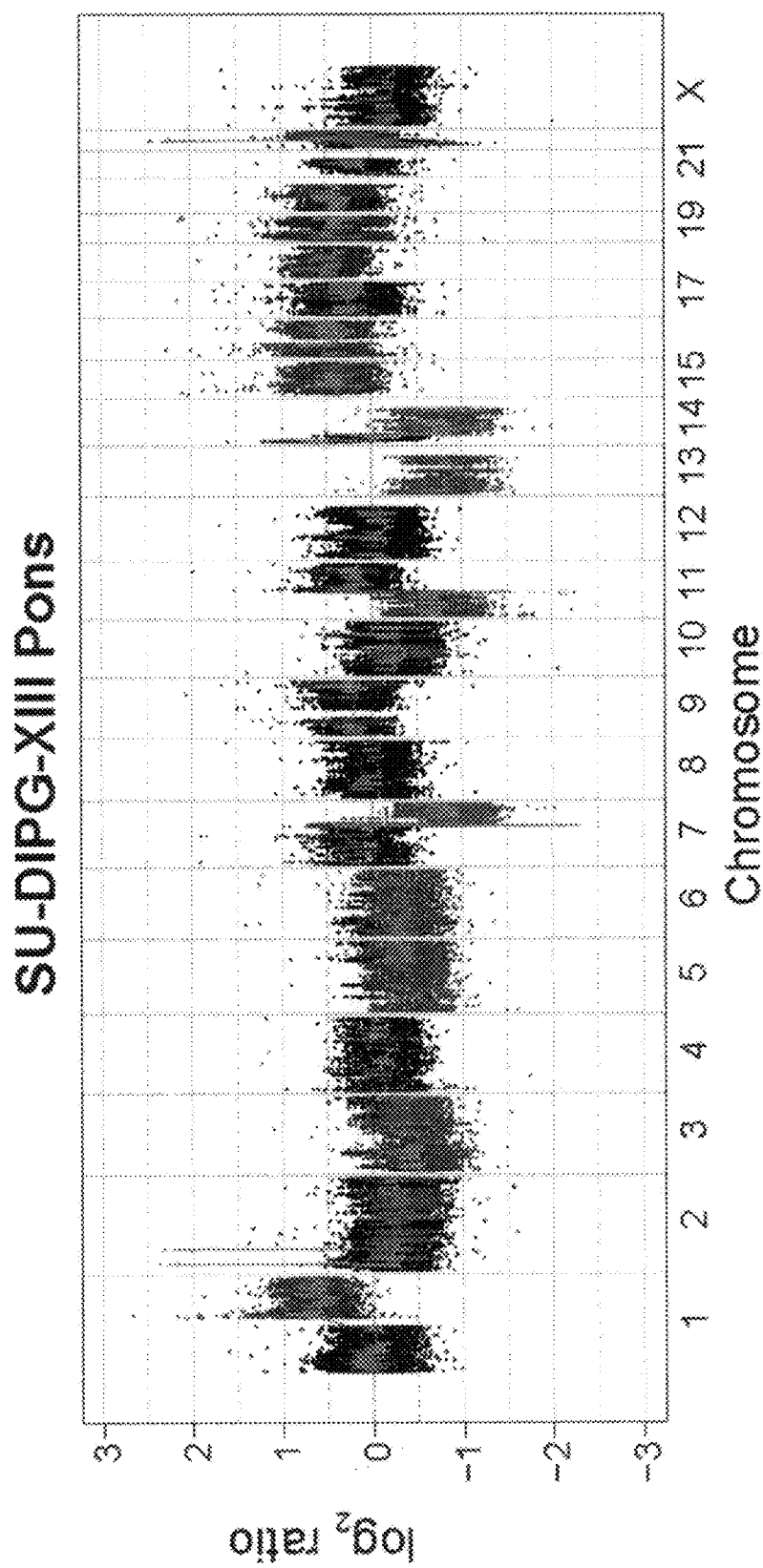
FIGS. 8A-8I show characterization of pontine and SVZ DIPG cells (related to FIG. 1).
Figure 8B:
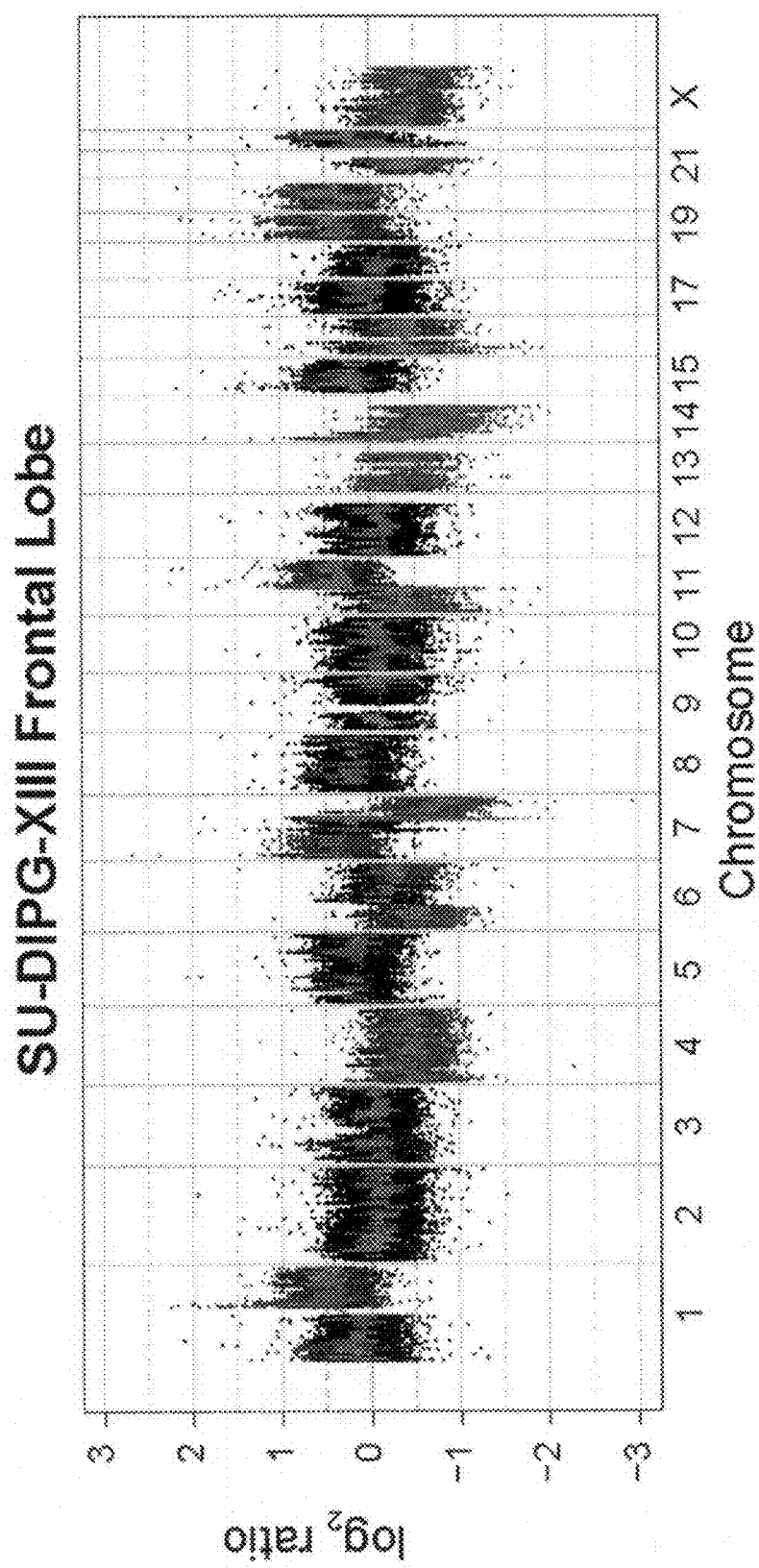
Figure 8C:
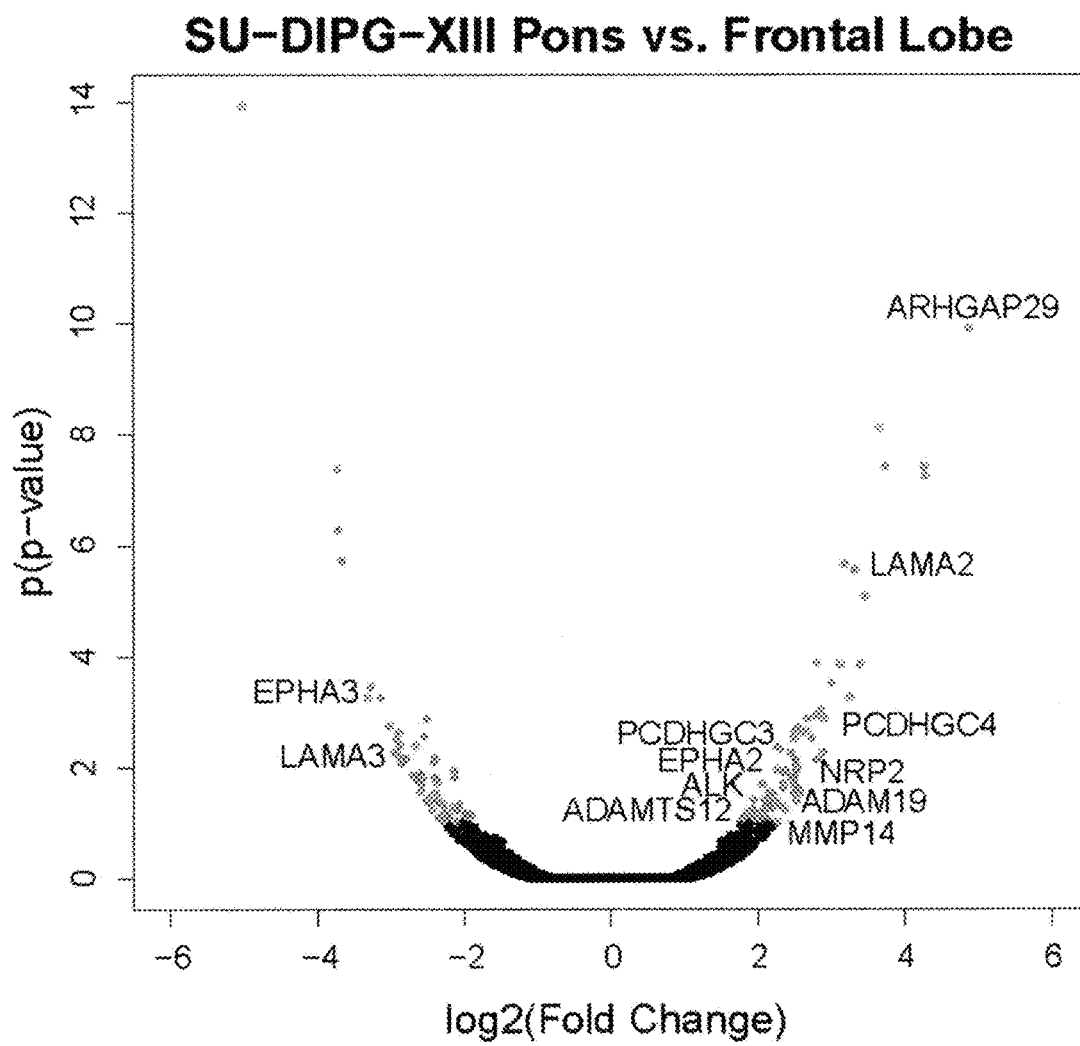
Figure 8D:
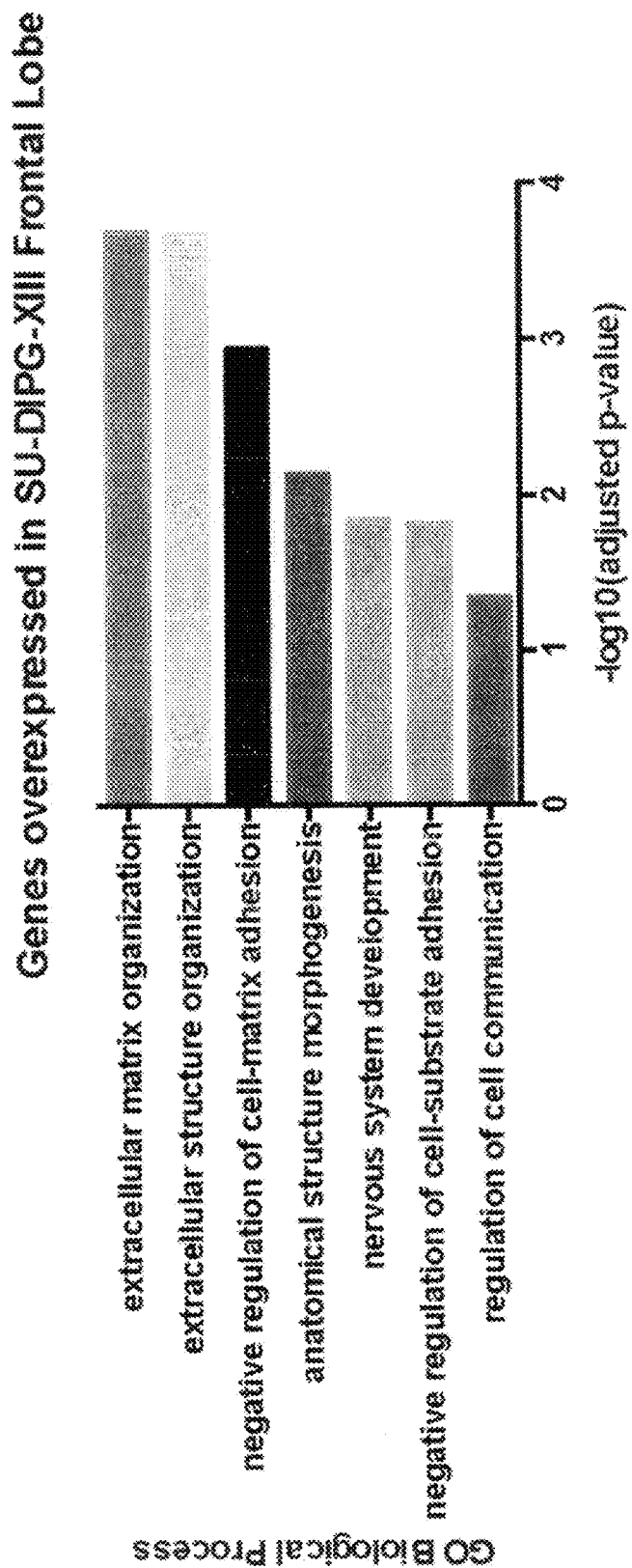
Figure 8E:
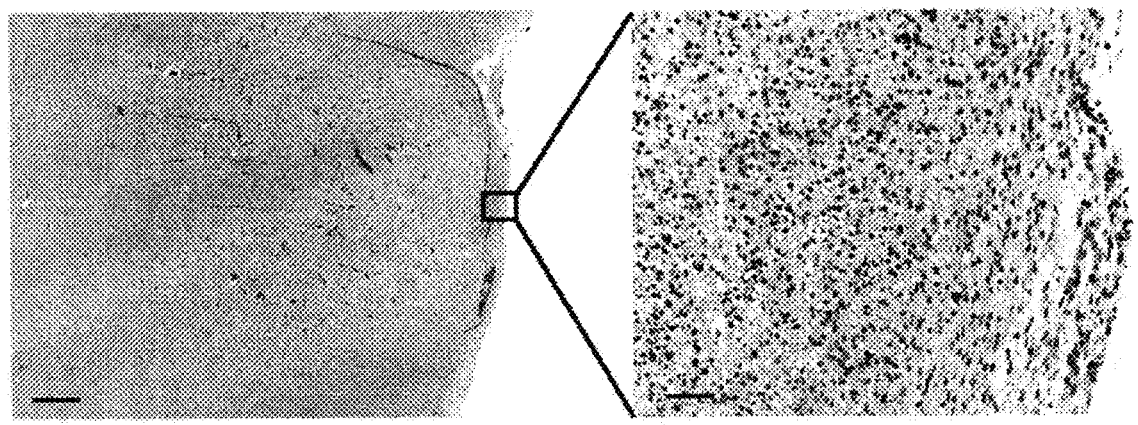
Figure 8F:
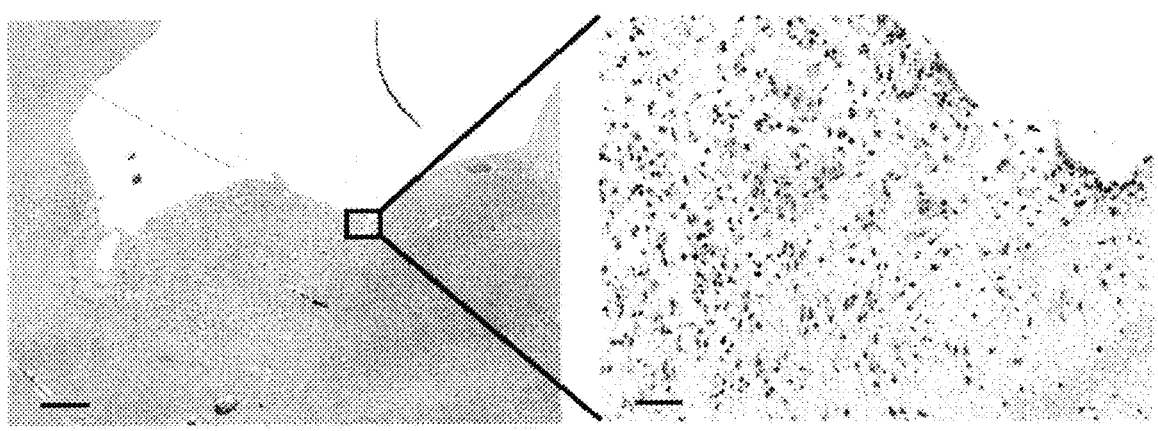
Figure 8G:
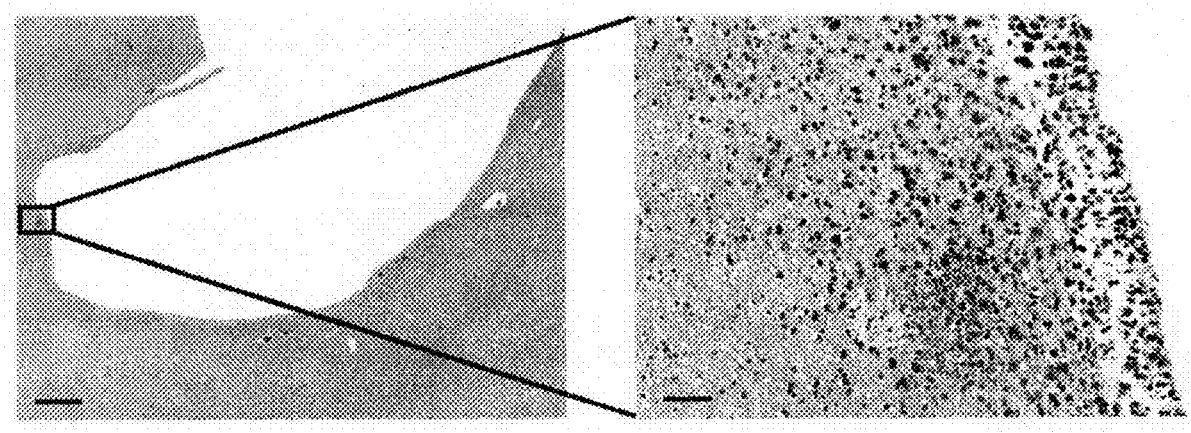
Figure 8H:
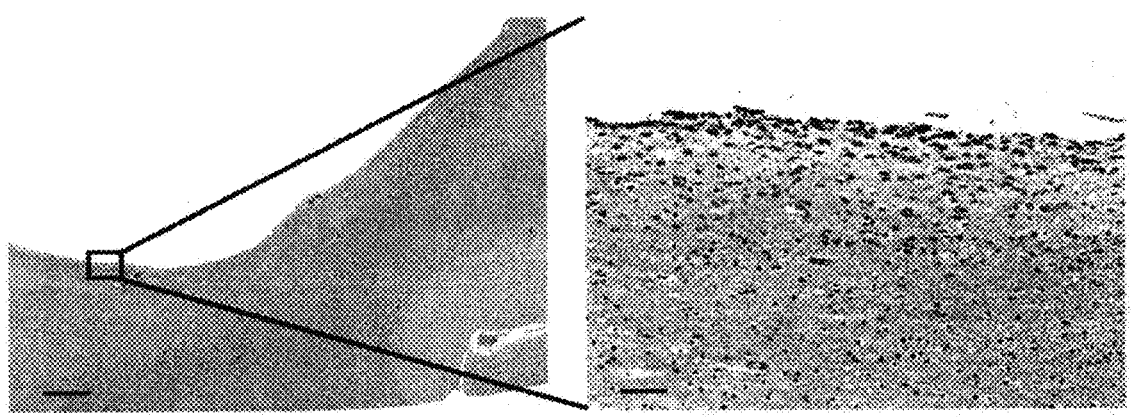
Figure 8I:
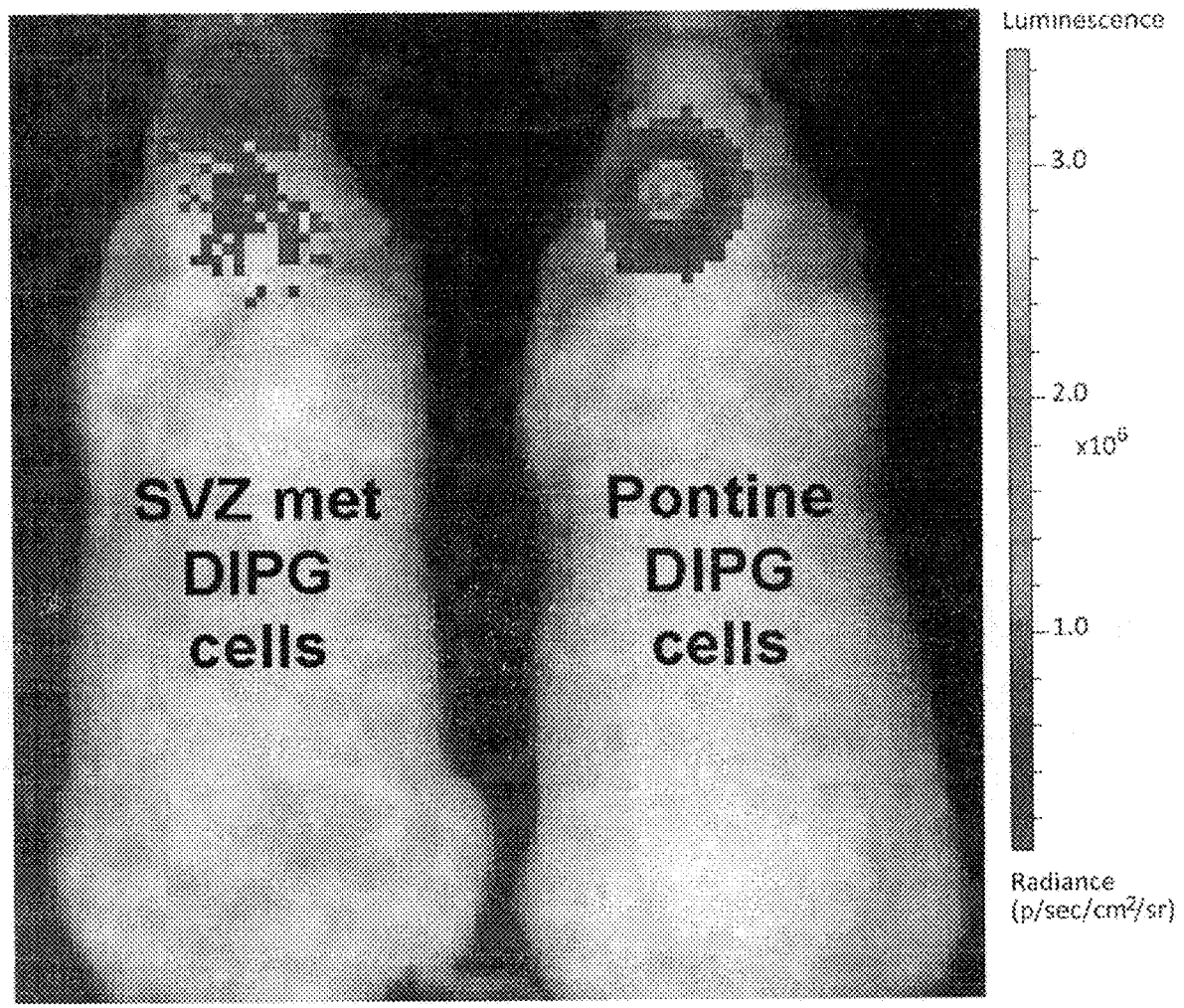

In this case, the pontine tumor had been treated with radiation therapy while the SVZ metastases were treatment-naive. While tumor spread to the lateral ventricle SVZ is frequent (FIGS. 1B, 1C, and 8E-8H), a culture of DIPG cells from an SVZ site of spread has not previously been established and provides a rare and valuable resource. Pontine and SVZ DIPG cells were transduced to express GFP and luciferase, and were subsequently orthotopically xenografted into the pons of juvenile immunodeficient (NOD-SCID-IL2R γ-chain-deficient; NSG) mice. Bioluminescent IVIS imaging demonstrated that the SVZ DIPG cells invaded supratentorially to the cerebrum (FIG. 1D), while the pontine DIPG cells from this case remained localized primarily to the hindbrain (FIG. 8I). The ability of the SVZ DIPG cells to invade widely may be due to higher expression of genes involved in extracellular matrix degradation, including matrix metalloproteinases and ADAM metallopeptidases (FIGS. 8C-8D). Histological analyses showed a diffusely infiltrating pattern of spread of SVZ DIPG cells that consistently demonstrated spread into the mouse SVZ (FIG. 1E), with glioma cells in close proximity to the SVZ neural precursor cells within the stem cell niche (FIG. 1F). Spread of SVZ DIPG cells throughout the brain increased over time, with 100% of mice exhibiting widespread tumor and infiltration of the SVZ by 16 weeks post-xenograft (FIG. 1G). This mouse model of SVZ invasion recapitulates the clinical behavior of the tumor and enables study of the mechanisms mediating invasion of the neural precursor cell niche.

Secreted Factors from NPCs Promote Glioma Invasion

Figure 2A:
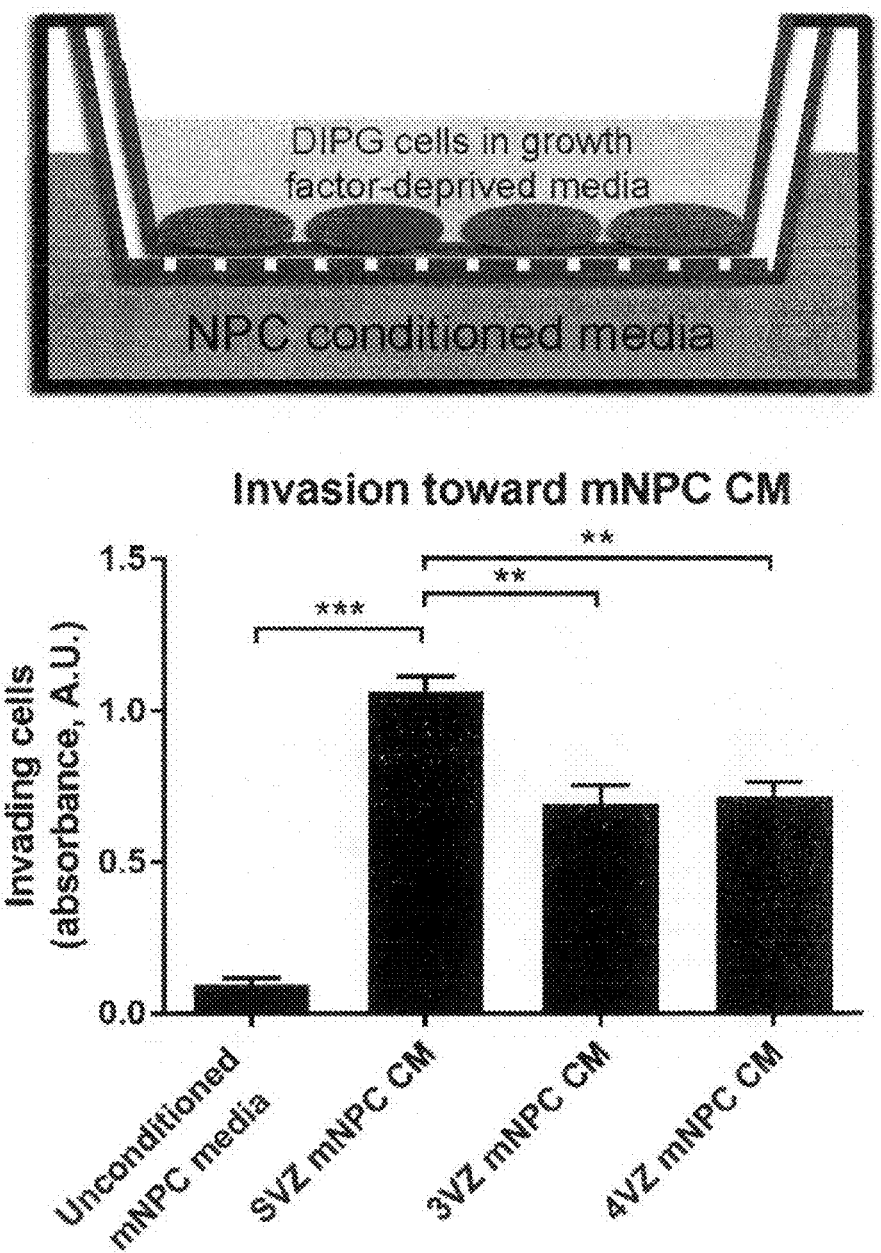
FIGS. 2A-2C show that factors secreted by NPCs promote high-grade glioma invasion.
Figure 2B:
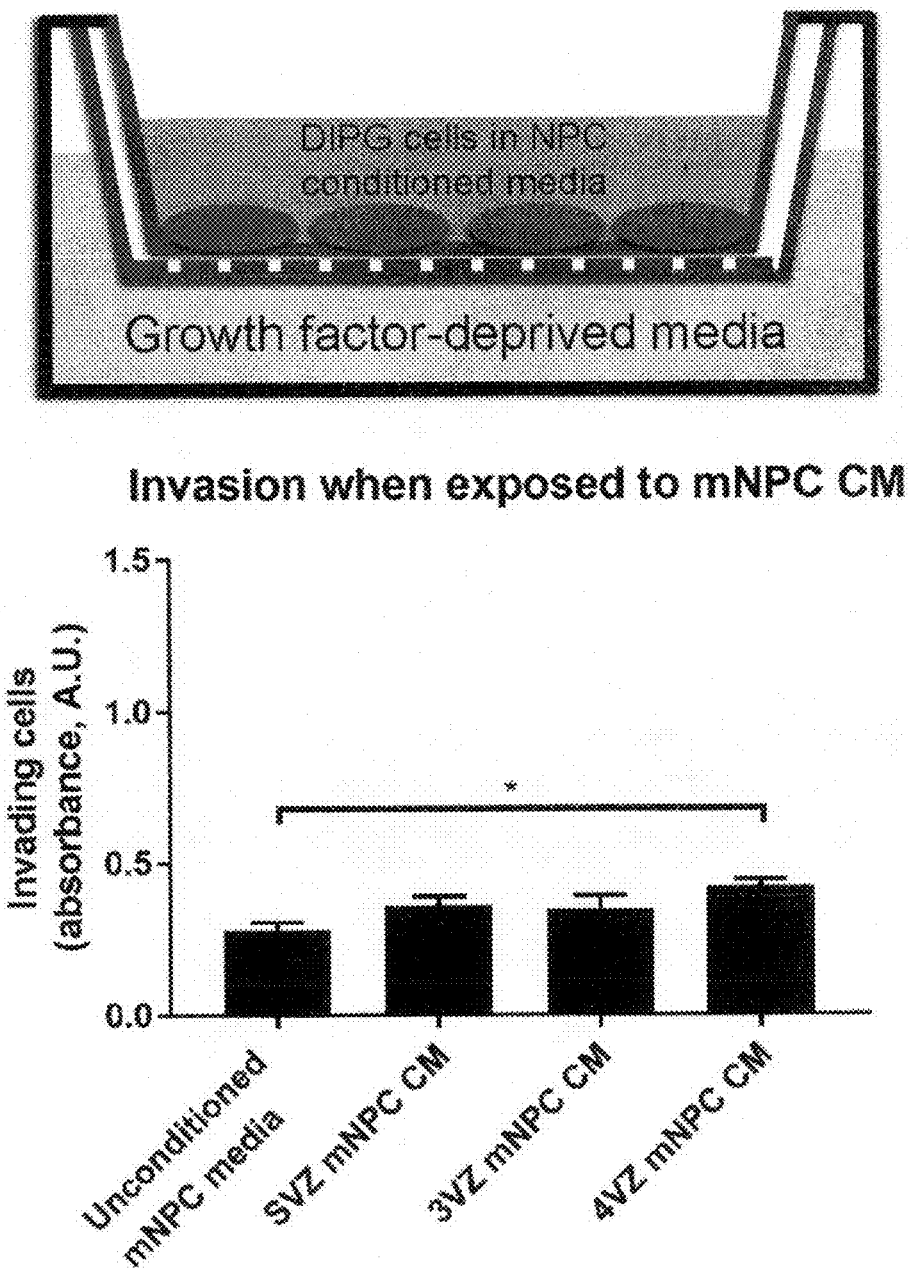
Figure 2C:
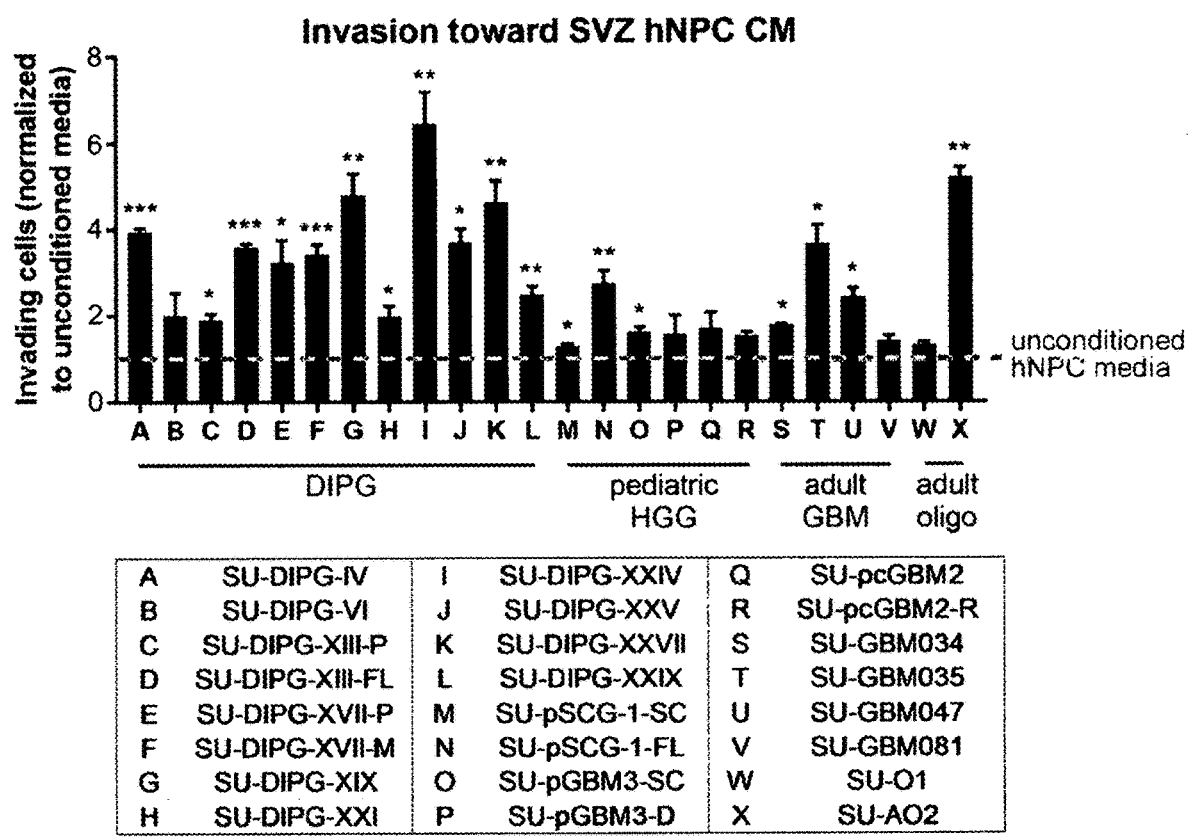
Figure 9A:
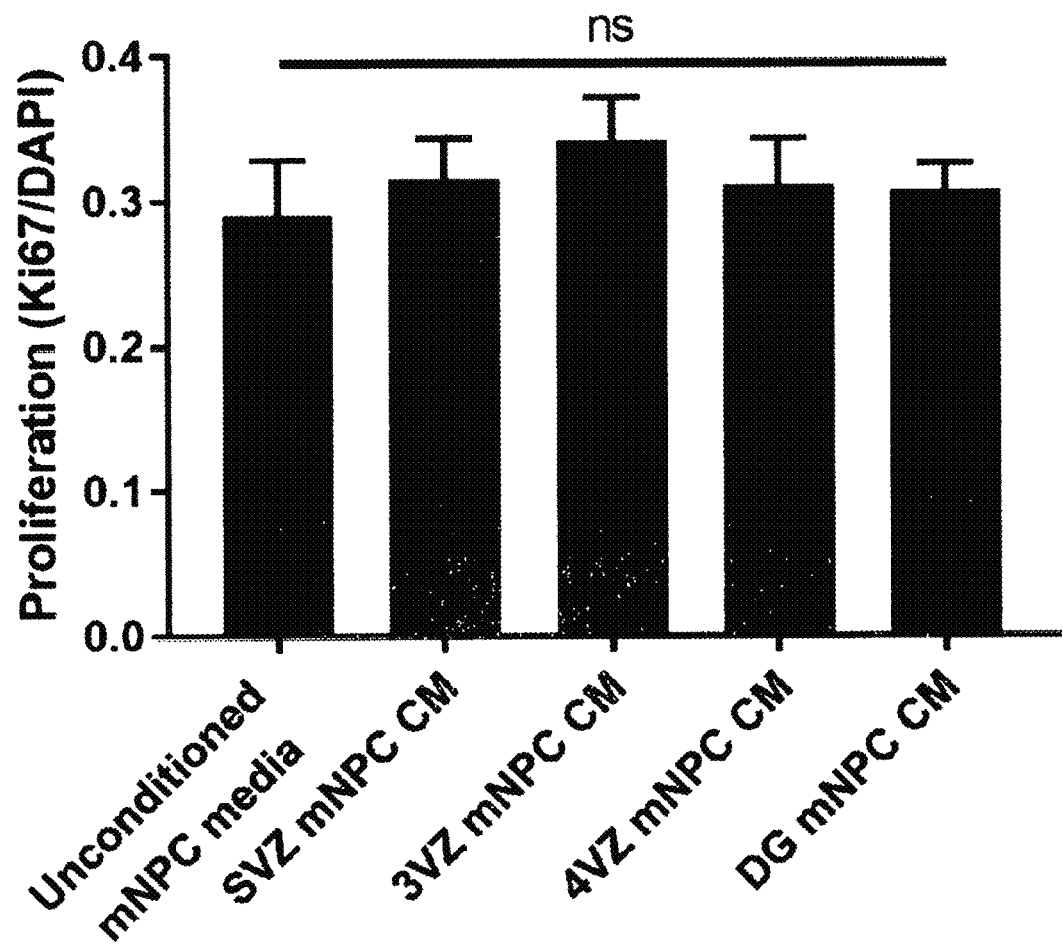
FIGS. 9A-9C show mNPC CM has no effect on DIPG cell proliferation or viability, Related to FIG. 2.
Figure 9B:
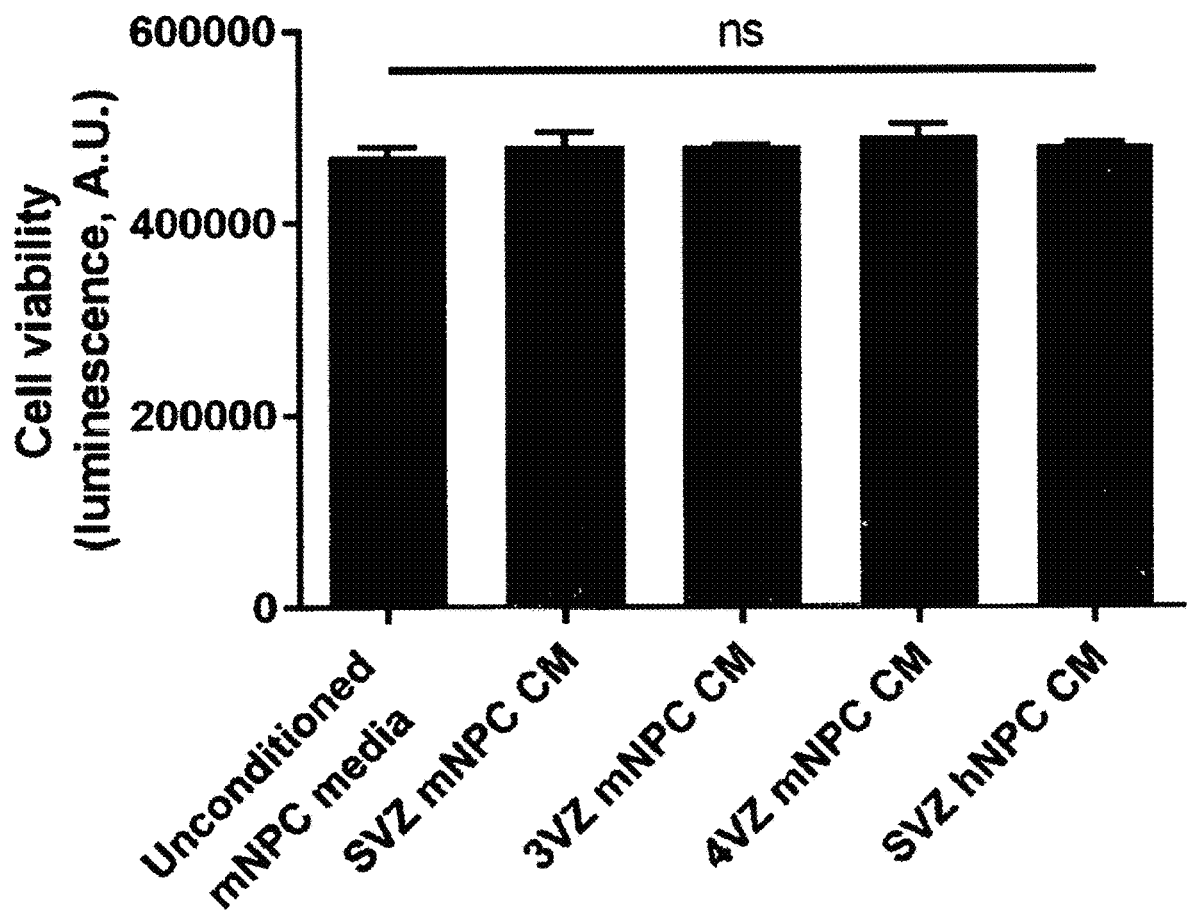
Figure 9C:
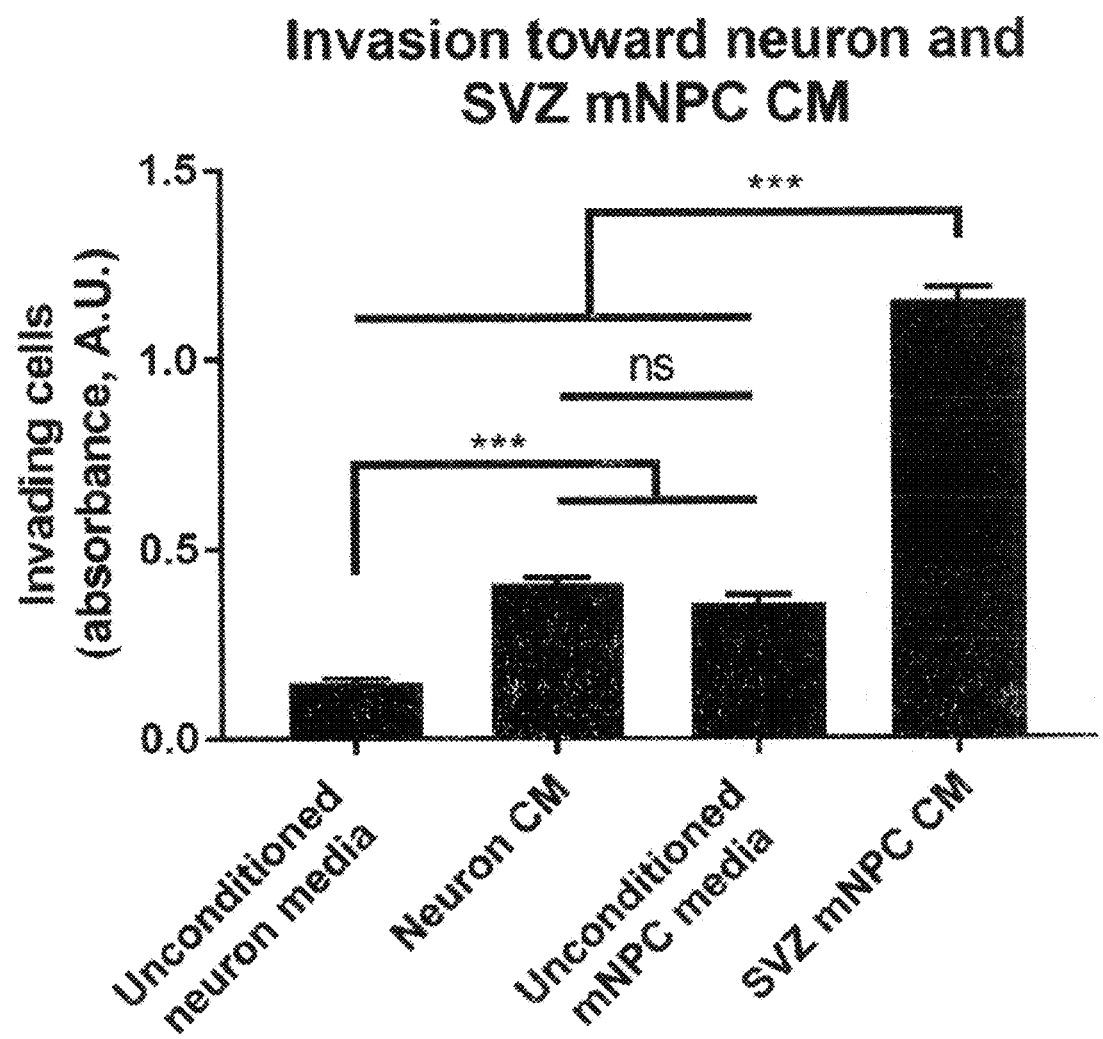

To test the invasion of glioma toward NPCs in vitro, we utilized a Boyden chamber Matrigel invasion assay, which allows for chemoattraction testing and mimics invasion through an extracellular matrix. A suspension of SVZ DIPG cells placed on top of the Matrigel layer was allowed to invade toward media conditioned by mouse NPCs (mNPC CM) isolated from the lateral ventricle subventricular zone (SVZ), third ventricular zone (3VZ), or fourth ventricular zone (4VZ), or toward unconditioned mNPC media for 72 hours. In this paradigm, SVZ DIPG cells showed the strongest preferential invasion toward SVZ mNPC CM, with less robust preferential invasion toward 3VZ or 4VZ mNPC CM, compared to unconditioned mNPC media (FIG. 2A). When the paradigm was reversed (SVZ DIPG cells co-incubated with mNPC CM, and allowed to invade toward growth factor-deprived media), SVZ DIPG cells co-incubated with 4VZ mNPC CM showed a small increase in general invasion (FIG. 2B). Exposure to media conditioned by any of the mNPC populations did not affect DIPG cell proliferation or viability (FIGS. 9A-9B). These data suggest that SVZ DIPG cells, which are intrinsically invasive, can modestly increase general invasiveness upon direct exposure to molecules secreted by 4VZ mNPCs, and have strong preferential invasion toward chemoattractant molecules secreted by SVZ mNPCs. To assess the relative specificity of invasion toward NPCs and to control for the possible chemoattractant effects of molecules secreted by cells in general, we tested invasion toward factors secreted by cultured murine neurons and found only a minimal effect; SVZ mNPC CM promoted a substantially more robust increase in DIPG invasion compared to murine neuronal CM (FIG. 9C). We next evaluated the CM from a culture of human fetal SVZ NPCs and found a similar chemoattractant effect on SVZ DIPG cells (FIG. 2C). Expanding these observations, we found that 18 out of a panel of 24 patient-derived glioma cell cultures, including DIPG, pediatric spinal cord glioma, pediatric cortical GBM, adult GBM, and oligodendroglioma, demonstrated increased invasion toward human SVZ NPC CM compared to unconditioned hNPC media (FIG. 2C; please see Tables 1 and 2 for clinical and molecular characteristics as well as STR DNA fingerprints of these patient-derived cultures). These results indicate that a range of molecularly distinct classes of HGGs exhibit preferential invasion toward factors secreted by SVZ NPCs.

NPC-Derived Secreted Factors Promoting Glioma Invasion are Proteins

Figure 3A:
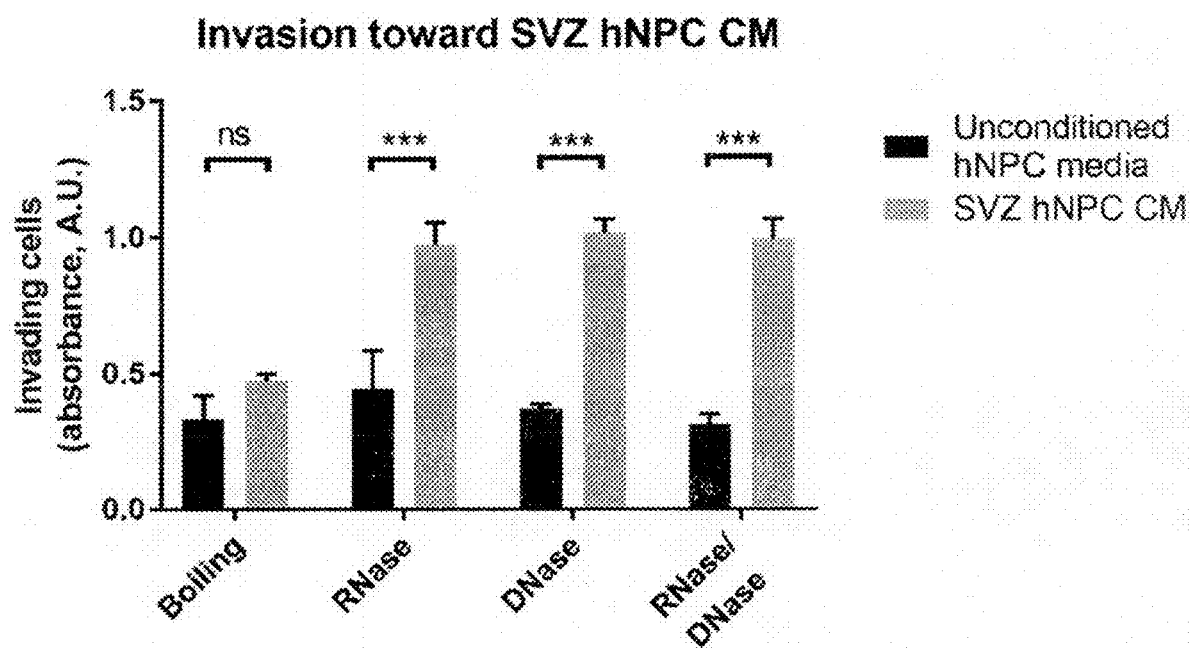
Figure 3B:
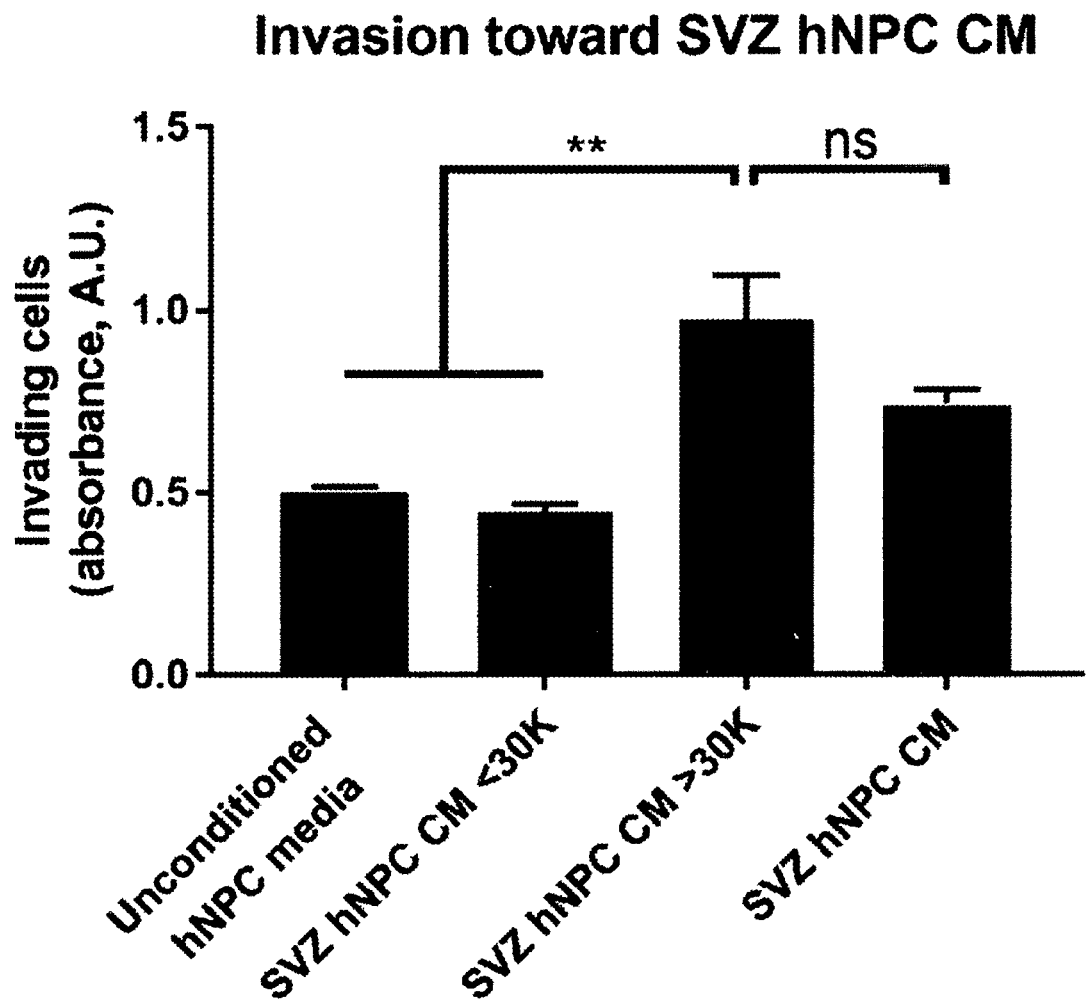
Figure 3C:
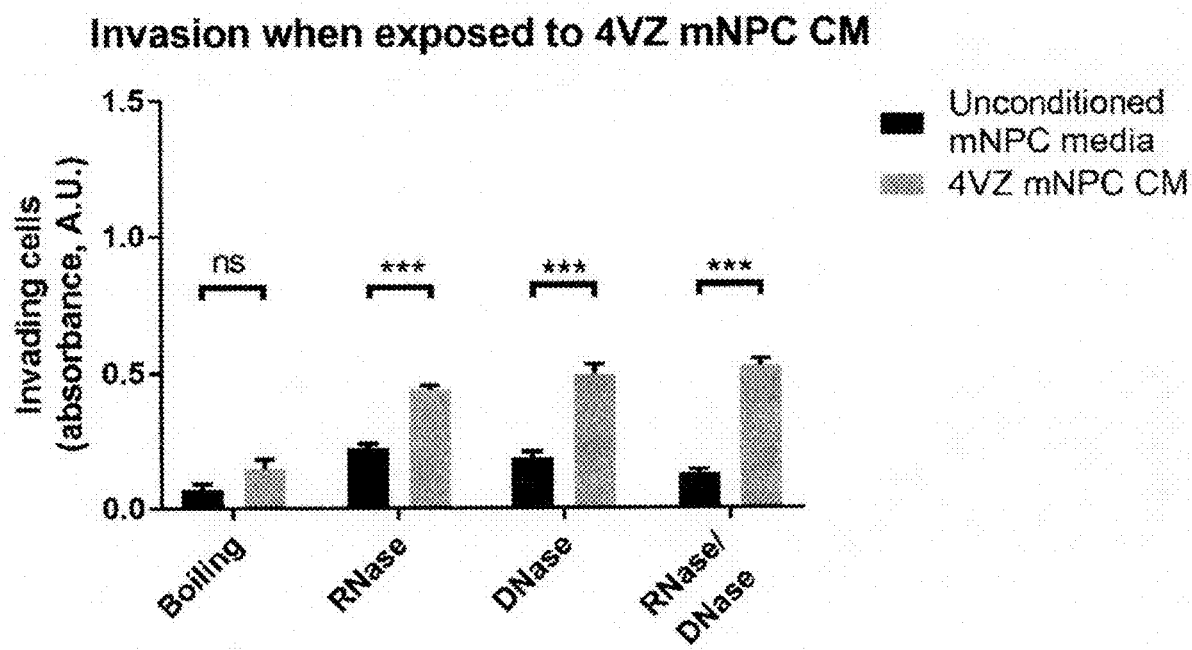
Figure 3D:
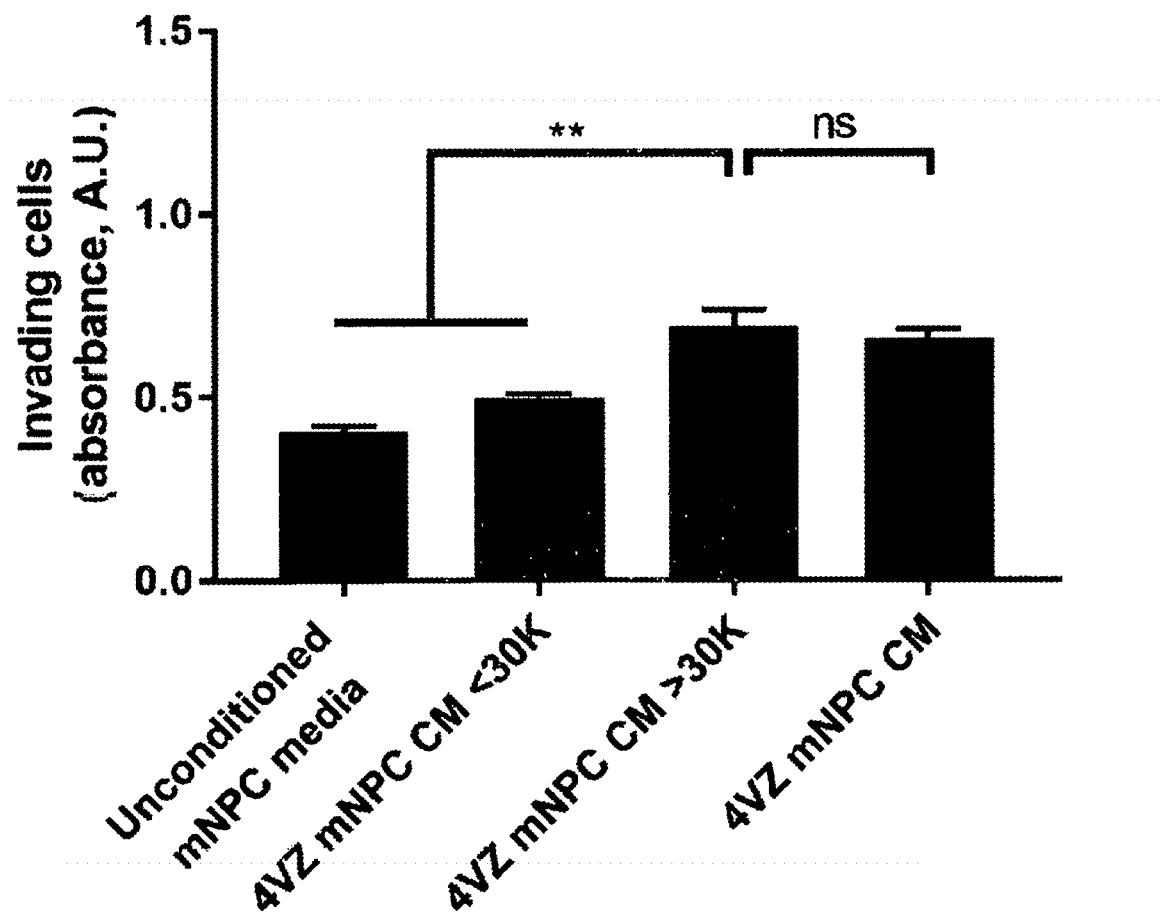
Figure 3E:
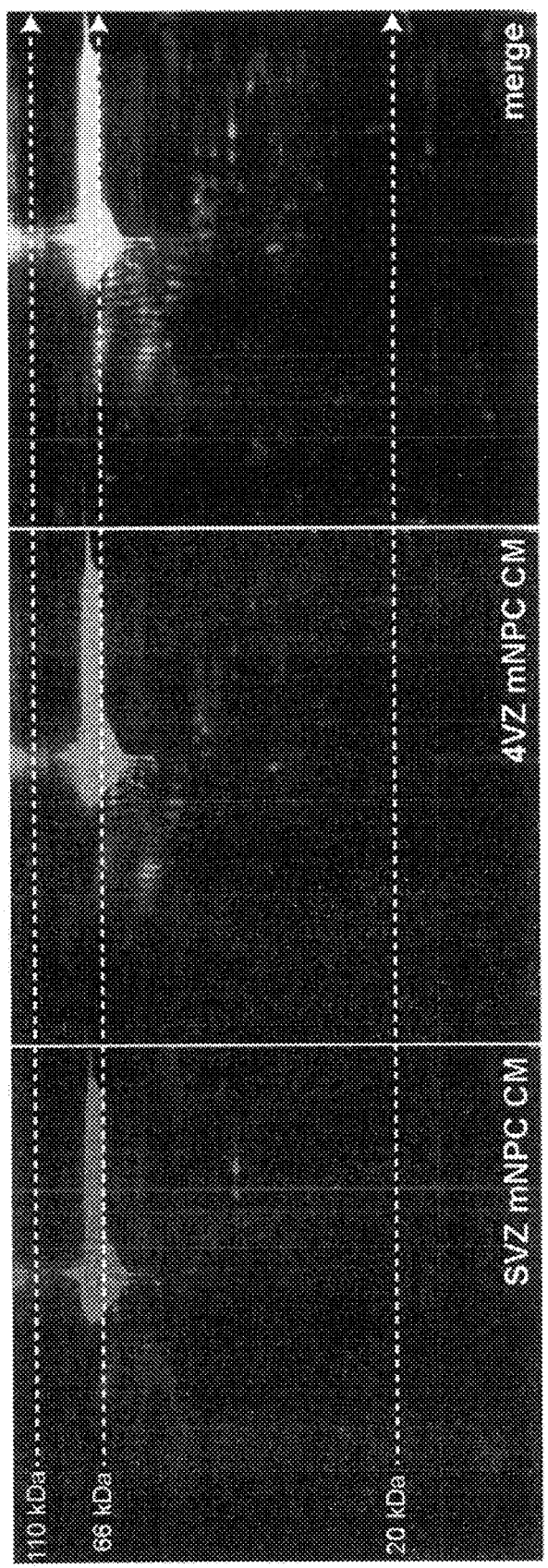

We performed several biochemical analyses to determine the nature of the NPC-secreted factors. Heat inactivation of SVZ hNPC CM abrogated its chemoattractant effect, whereas RNase and DNase treatment did not (FIG. 3A). Size fractionation of the CM showed that DIPG cells exhibited strong invasion toward the >30 kDa fraction, but not toward the <30 kDa fraction (FIG. 3B). Together, these data indicate that the SVZ hNPC-secreted chemoattractant(s) are protein(s) greater than 30 kDa in size. Similarly, the invasion-promoting factor(s) in the 4VZ mNPC CM also appear to be protein(s) greater than 30 kDa (FIGS. 3C and 3D). To identify the invasion-promoting proteins present in SVZ and 4VZ mNPC CM, we utilized 2D gel electrophoresis to separate the secreted proteins by size and charge, followed by mass spectrometry to identify the differentially secreted protein spots (FIG. 3E). Spots differentially detected in SVZ mNPC CM compared to 4VZ mNPC CM by a factor of 1.5 were selected for further investigation. These analyses generated a list of candidate proteins that were differentially secreted by SVZ and 4VZ mNPCs (FIG. 3F).

Figure 4A:
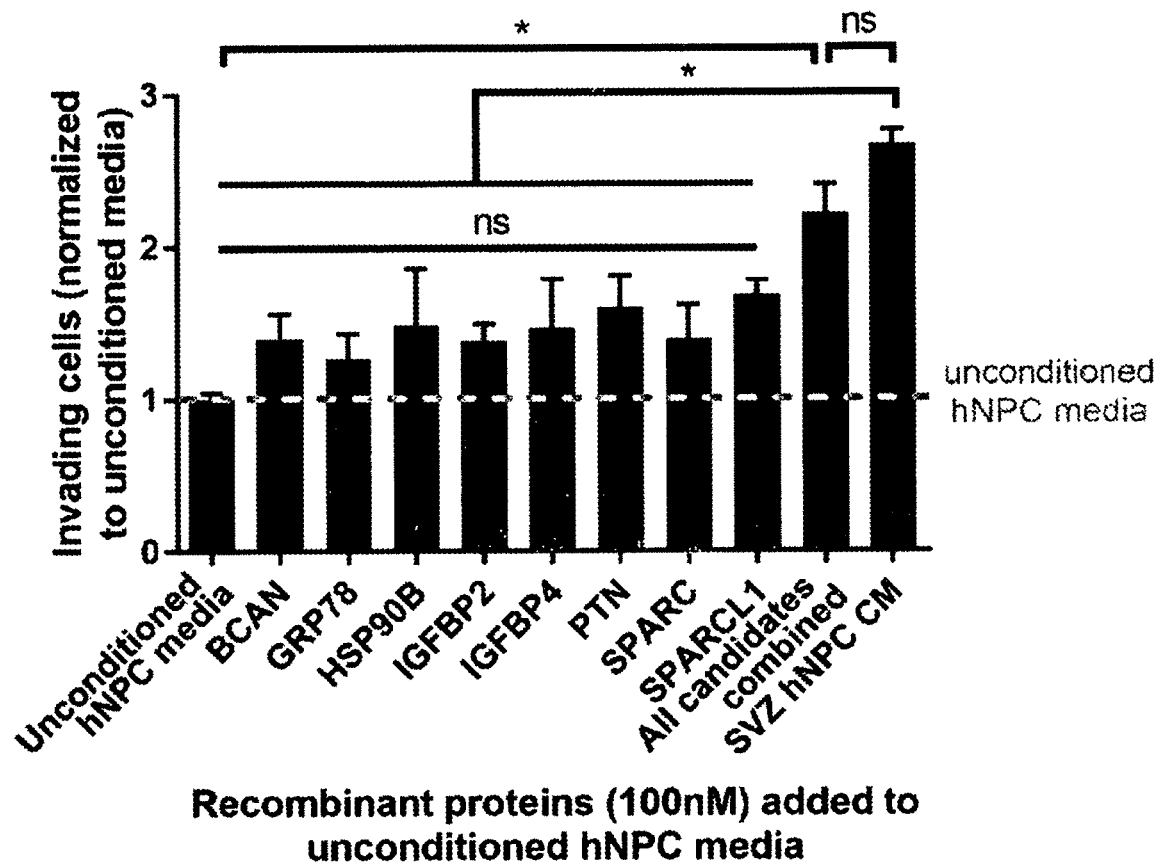
FIGS. 4A-4E show that the combination of PTN and three required binding partners promotes DIPG invasion toward SVZ hNPC CM.
Figure 4B:
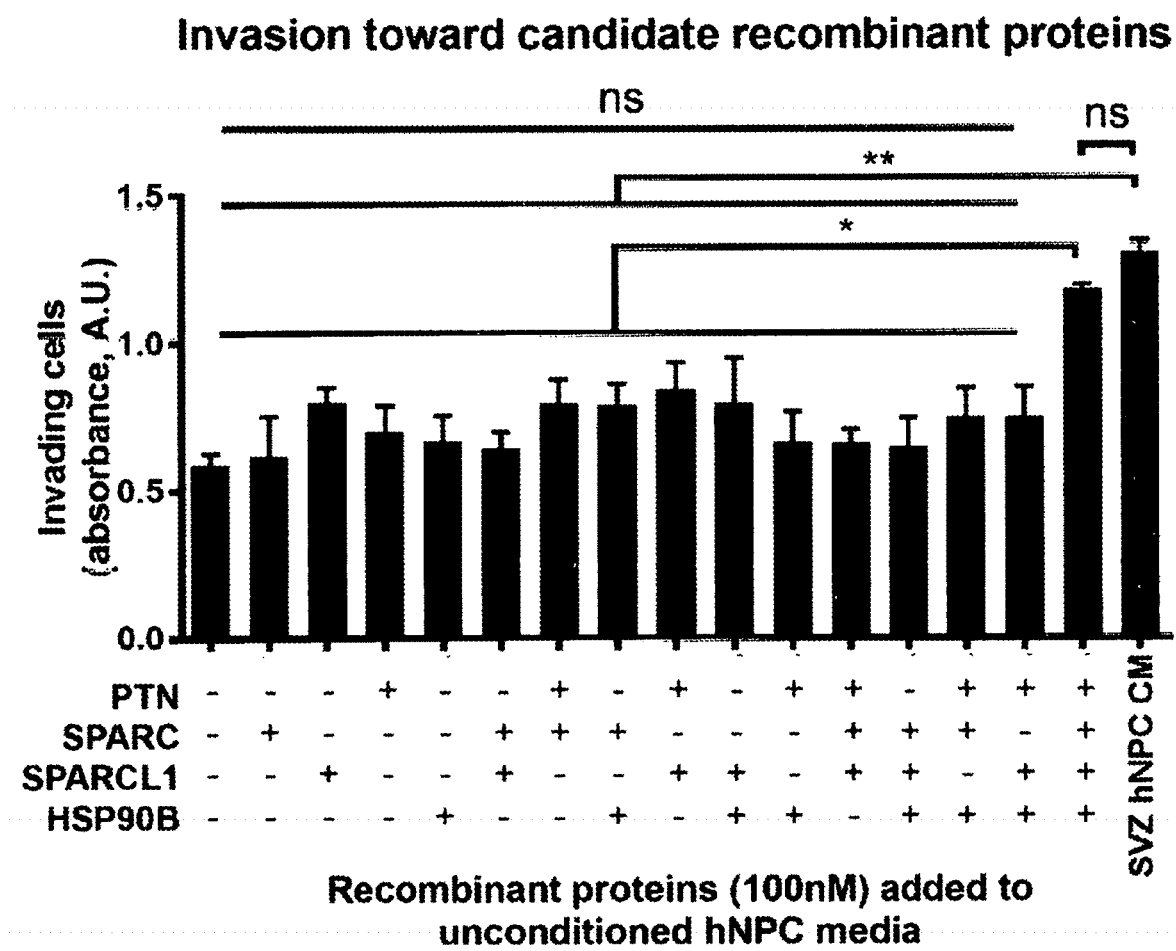
Figure 10A:
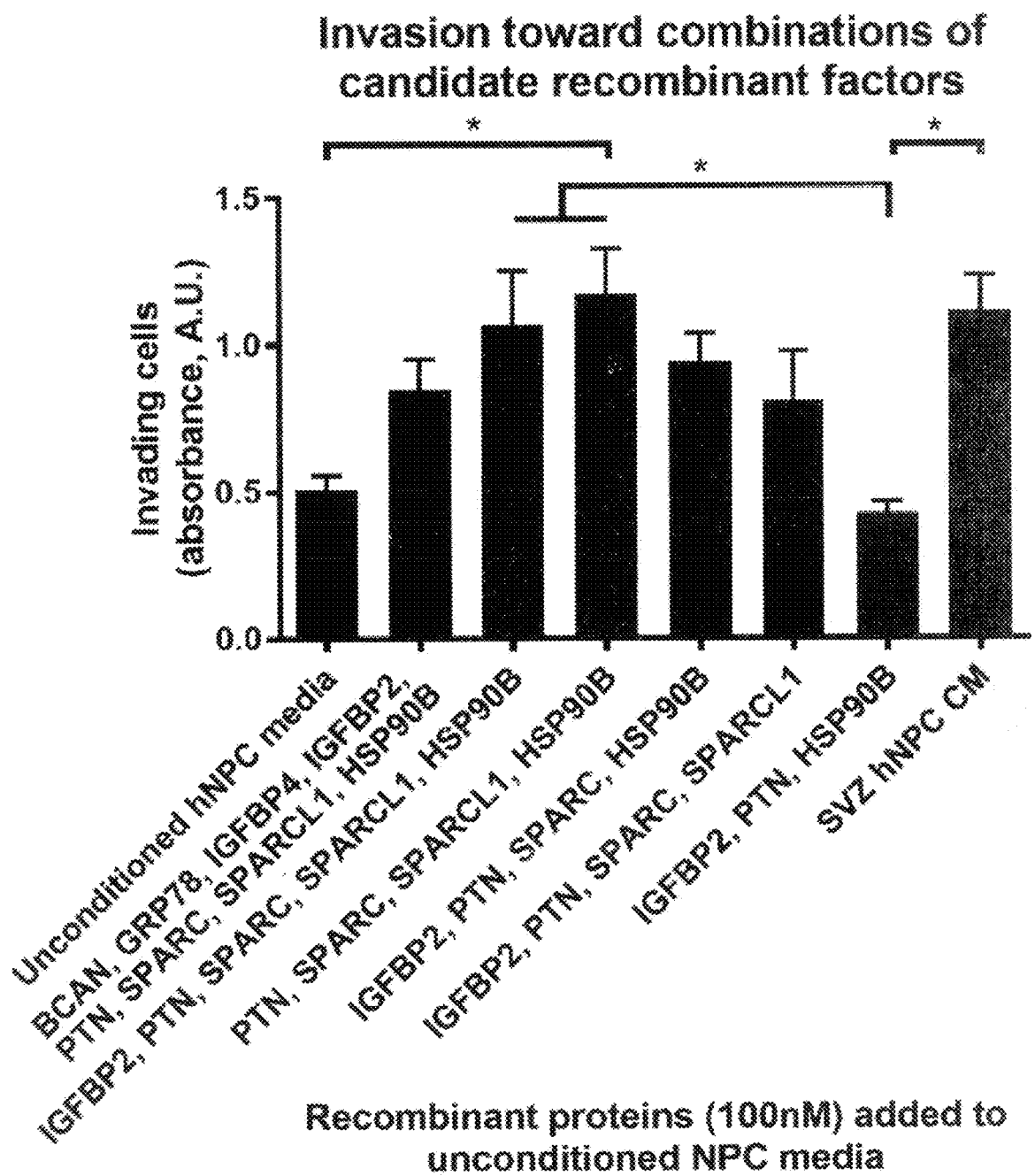
FIGS. 10A-10D show invasion of DIPG cells toward candidate recombinant proteins, Related to FIG. 4.
Figure 10B:
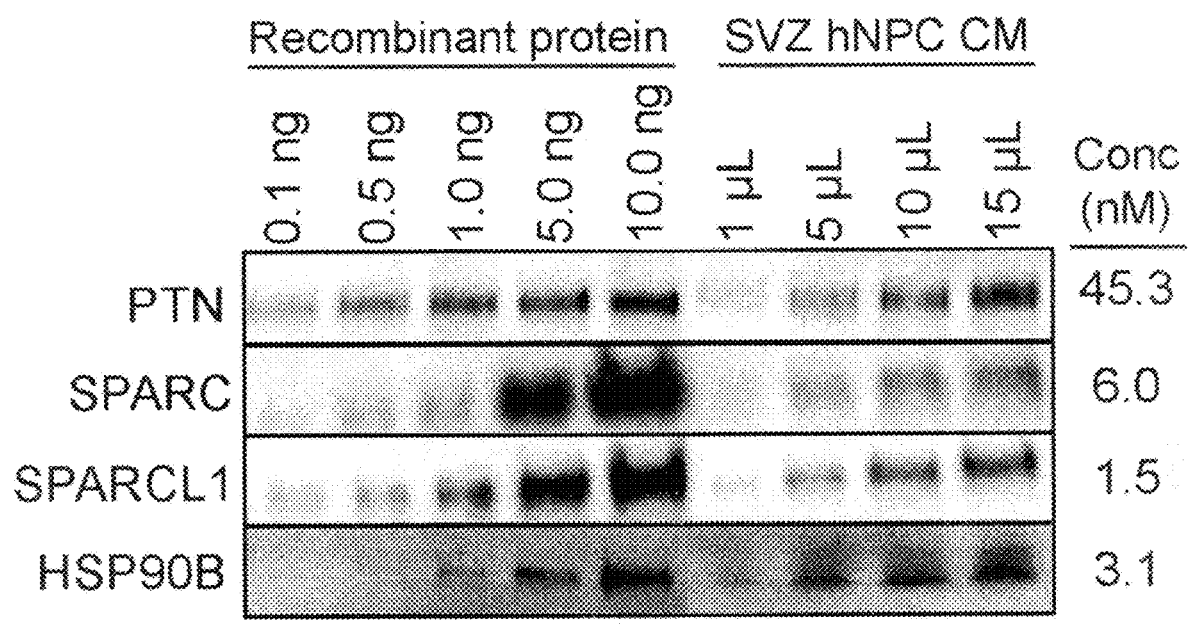
Figure 10C:
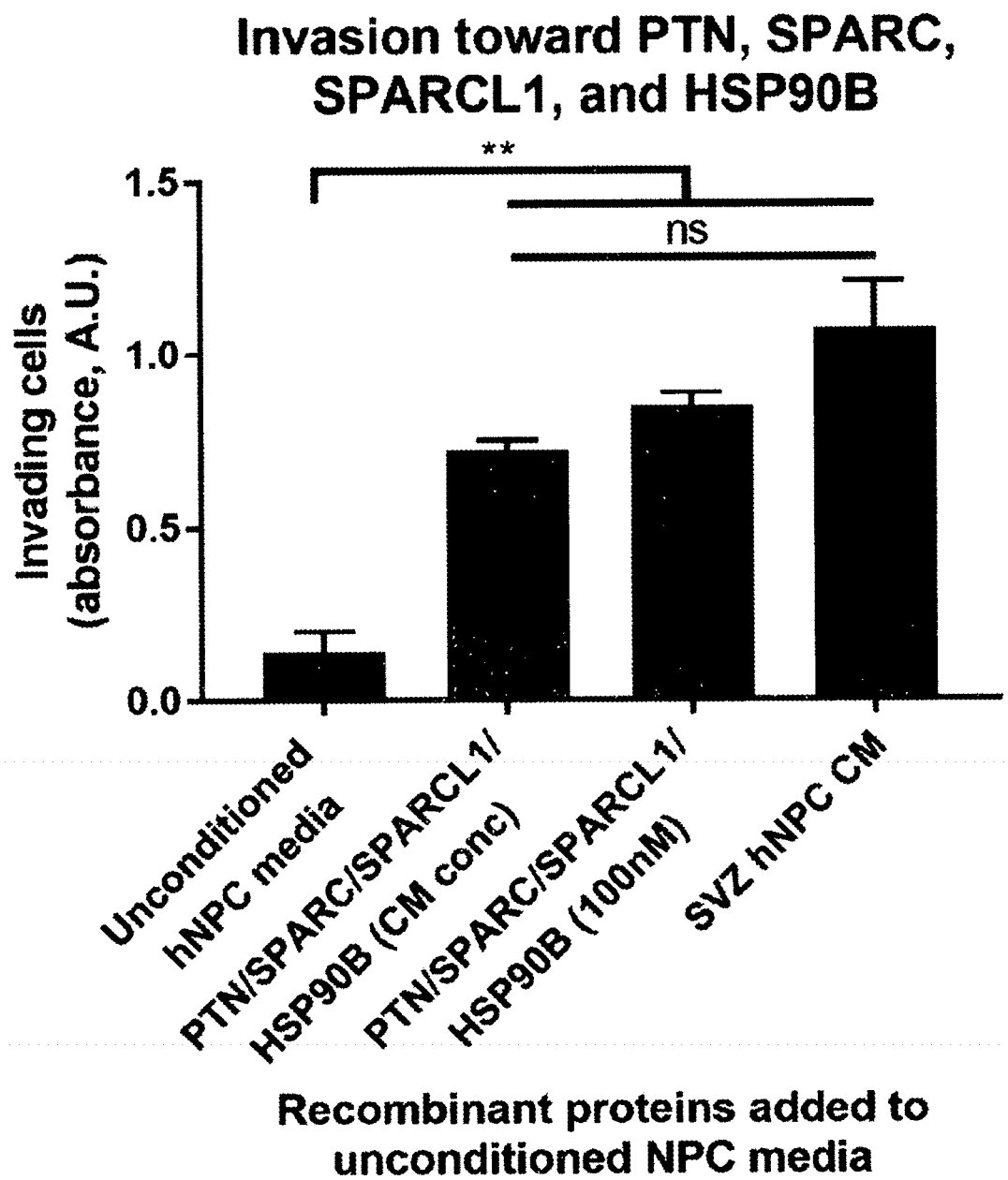

Pleiotrophin, in Combination with Required Binding Partners, Promotes Glioma Invasion Toward the SVZ We subsequently tested the sufficiency of each of the eight candidate proteins to chemoattract DIPG cells. Using human recombinant proteins in the Matrigel invasion assay, we tested directed invasion of DIPG cells toward each candidate factor. No significant increase in invasion was observed for individual candidate proteins compared to unconditioned media (FIG. 4A). We then tested DIPG invasion toward various combinations of the candidate proteins, and found the combination of four proteins: pleiotrophin (PTN), secreted protein acidic and rich in cysteine (SPARC), SPARC-like protein 1 (SPARCL1), and heat shock protein 90B (HSP90B), to exhibit a chemoattractant effect most similar to that of the SVZ hNPC CM (FIG. 10A). Testing combinations of two, three, or all four of these proteins demonstrated that only the combination of all four proteins was sufficient to recapitulate the full invasion-promoting effect of SVZ hNPC CM (FIG. 4B). PTN is present in the highest concentration of the four proteins in SVZ hNPC CM as estimated by immunoblot (FIG. 10B). The estimated concentrations of the four proteins in SVZ hNPC CM were confirmed to be sufficient for DIPG invasion (FIG. 10C).

Figure 4C:
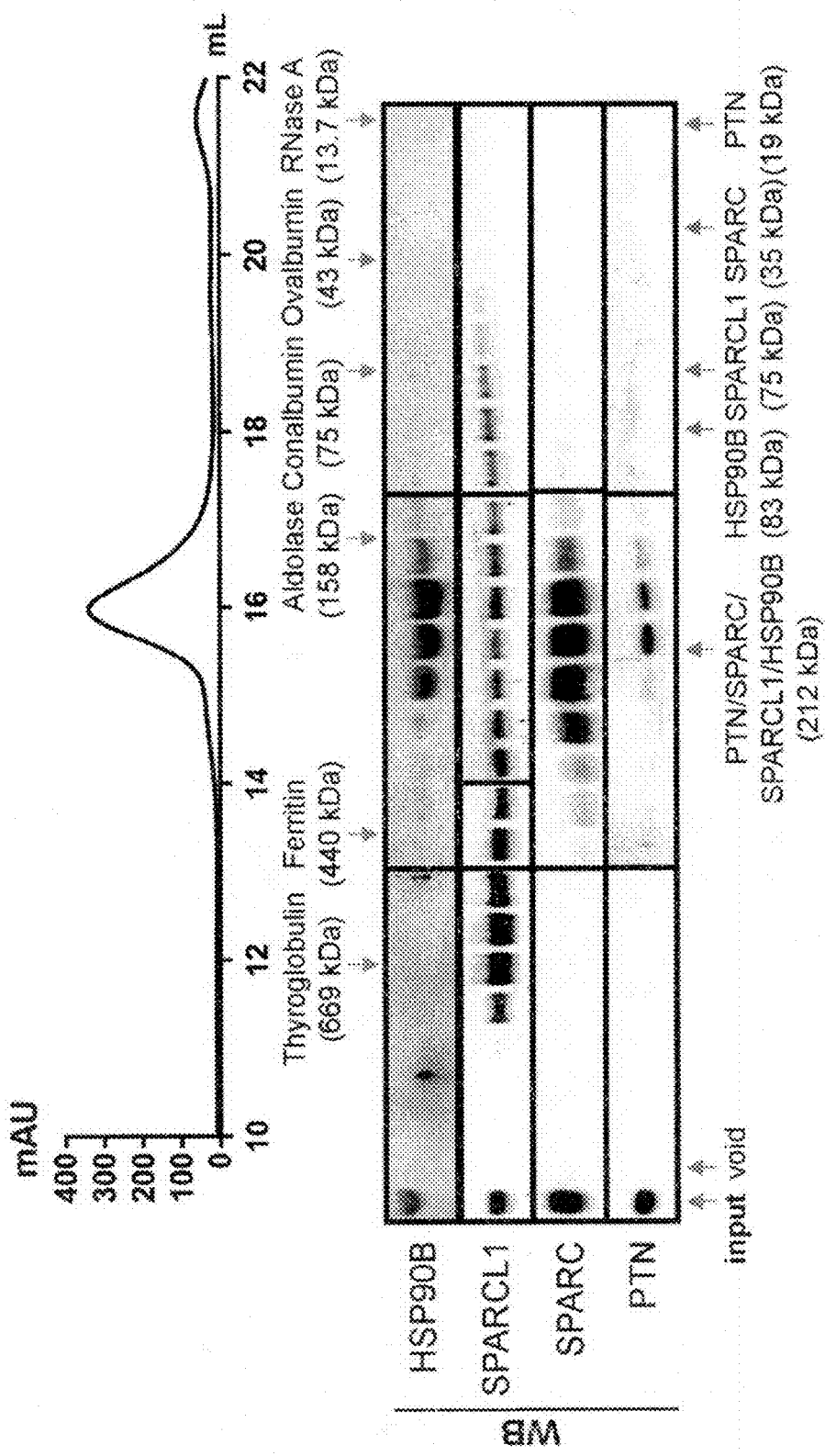
Figure 4D:
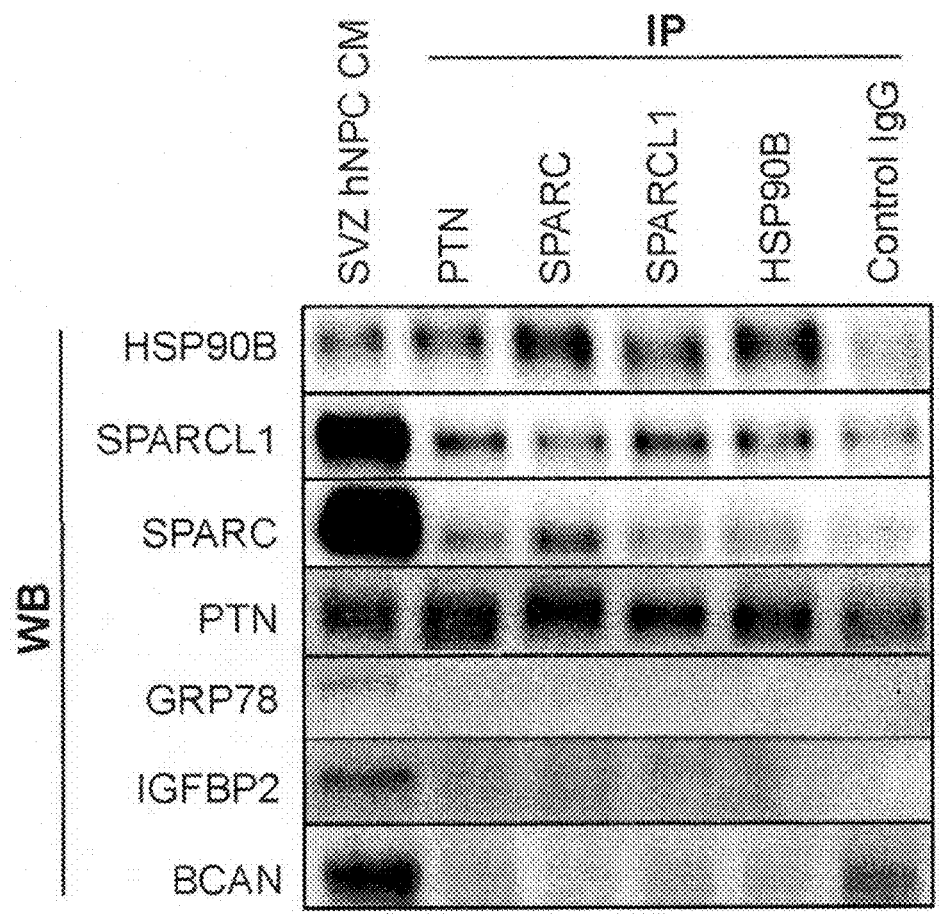

In order to elucidate the nature of the interaction between the four proteins, we performed biochemical analyses to determine the size and binding interactions of the proteins of interest in SVZ hNPC CM. By size exclusion chromatography of concentrated SVZ hNPC CM and subsequent Western blot analysis of the eluted fractions, we found that the four proteins of interest all coeluted at approximately the size that would be expected for a complex of all four proteins (FIG. 4C). With the exception of SPARCL1, the four proteins had similar patterns of elution and fractionated mostly at the larger size of all four proteins combined, and did not fractionate at the sizes of the single proteins. This suggests that the proteins exist primarily as part of a four-protein complex, rather than as free monomers. Furthermore, in immunoprecipitation reactions, we found that by immunoprecipitating any one of the four proteins, all four proteins copurified and did not precipitate with a control IgG antibody (FIG. 4D). To assess the specificity of the pull-down assay, three control proteins also present in SVZ hNPC CM: 78 kDa glucose-regulated protein (GRP78), insulin-like growth factor binding protein 2 (IGFBP2), and brevican (BCAN), were immunoprecipitated and were not found to copurify with any of the four proteins (FIG. 4D). These results further demonstrate that the four proteins physically interact and specifically bind together as a single complex. Of the four identified proteins, PTN was of particular interest, as it has been demonstrated to promote adult GBM cell migration through autocrine/paracrine action (Lu et al. (2005) J. Biol. Chem. 280, 26953-26964; Ulbricht et al. (2003) J. Neuropathol. Exp. Neurol. 62, 1265-1275).

The requirement of SPARC, SPARCL1, and HSP90B as binding partners for PTN in promoting glioma invasion is consistent with the role of SPARC and SPARCL1 as adapter proteins that act as connecting molecules (Lane and Sage (1994) FASEB J. 8, 163-173), and the role of HSP90B as a chaperone protein facilitating the interactions of other proteins (Csermely et al. (1998) Pharmacol. Ther. 79, 129-168; Wiech et al. (1992) Nature 358, 169-170). The binding of these three proteins may act to stabilize PTN, which has been shown to promote haptotactic glioma cell migration, i.e. migration toward immobilized PTN, as opposed to chemotactic migration toward free soluble PTN molecules (Lu et al. (2005) J. Biol. Chem. 280, 26953-26964; Ulbricht et al. (2003) J. Neuropathol. Exp. Neurol. 62, 1265-1275).

Figure 4E:
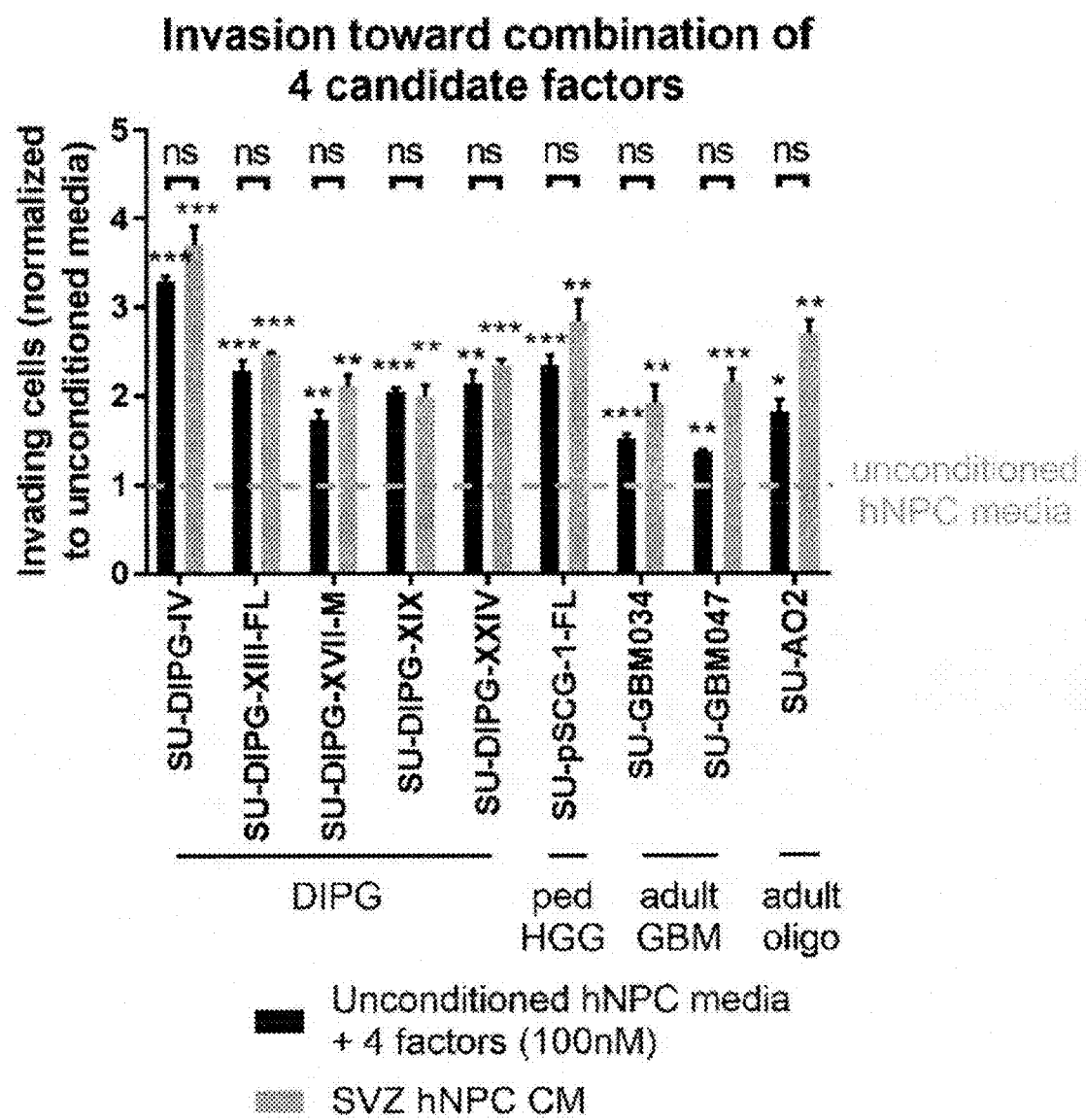
Figure 10D:
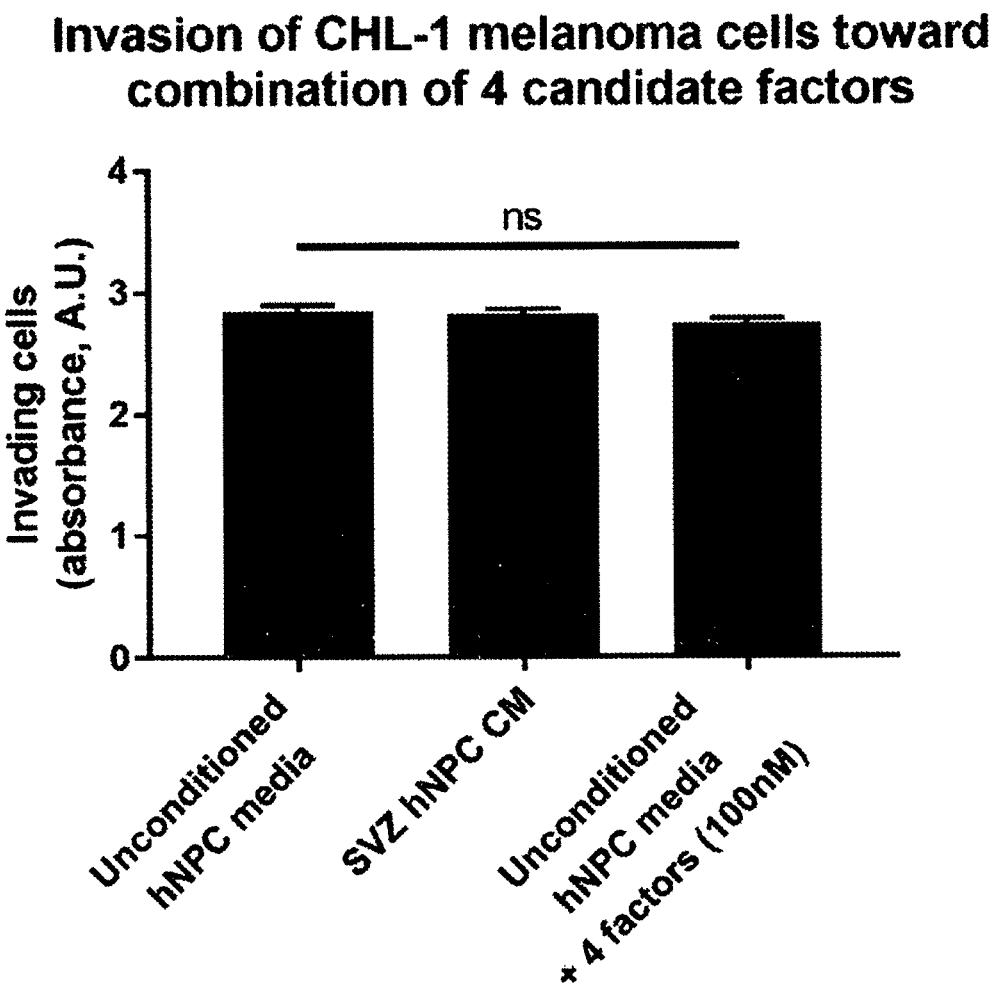

Similar to the conserved invasive response toward SVZ hNPC CM, we found that 9 out of 9 patient-derived glioma cell cultures, including DIPG, pediatric spinal cord glioma, adult GBM, and anaplastic oligodendroglioma, invaded toward the combination of PTN and its three binding partners (FIG. 4E). As an example of a cancer with known metastatic tropism for the brain, but that does not preferentially spread to the SVZ, we tested a melanoma cell line and found that it did not invade toward SVZ hNPC CM or toward the PTN complex (FIG. 10D). Together, these results indicate that rather than acting individually, PTN and its three binding partners form a complex and signal as a unit in promoting the directional invasion of a range of HGGs.

Figure 5A:
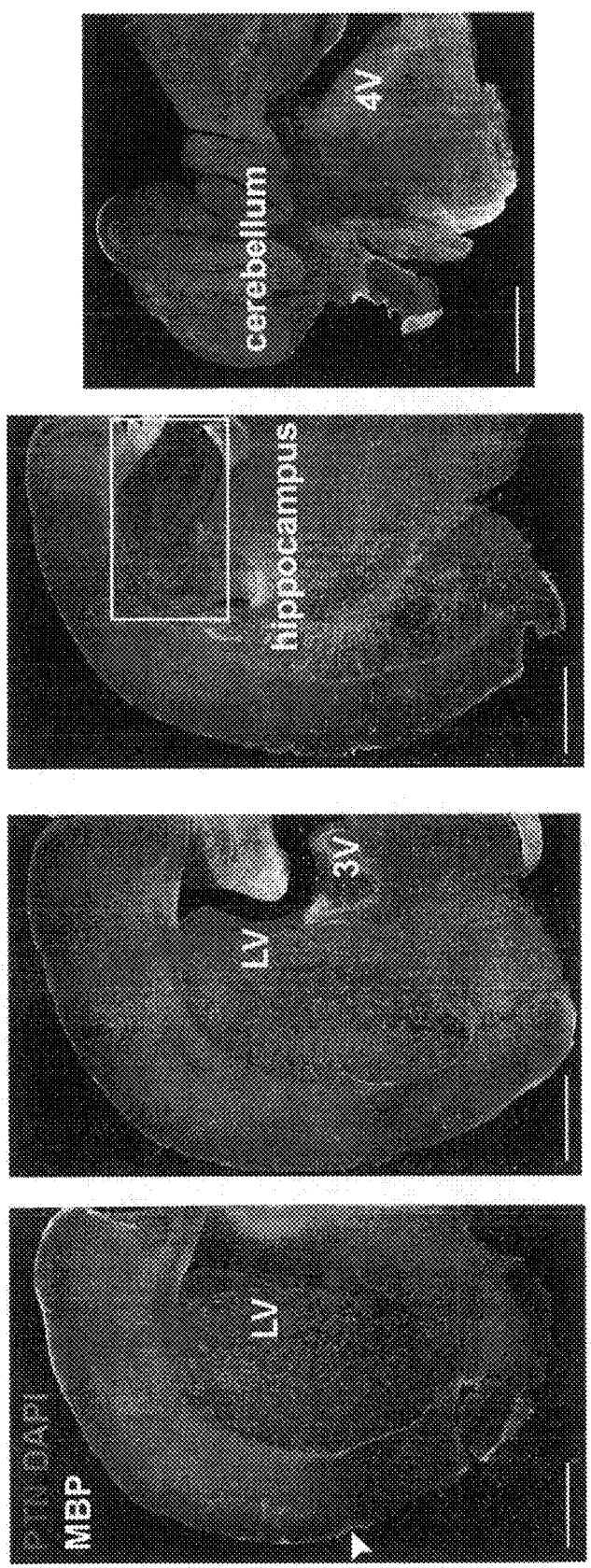
FIGS. 5A-5H show that PTN expression is enriched in the postnatal SVZ.
Figure 5B:
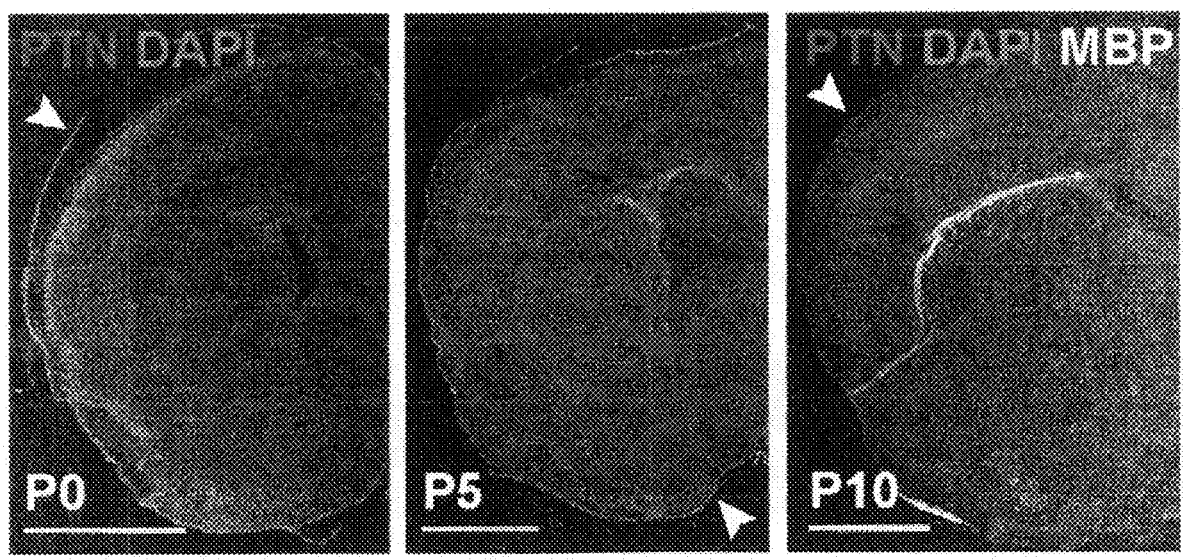
Figure 5C:
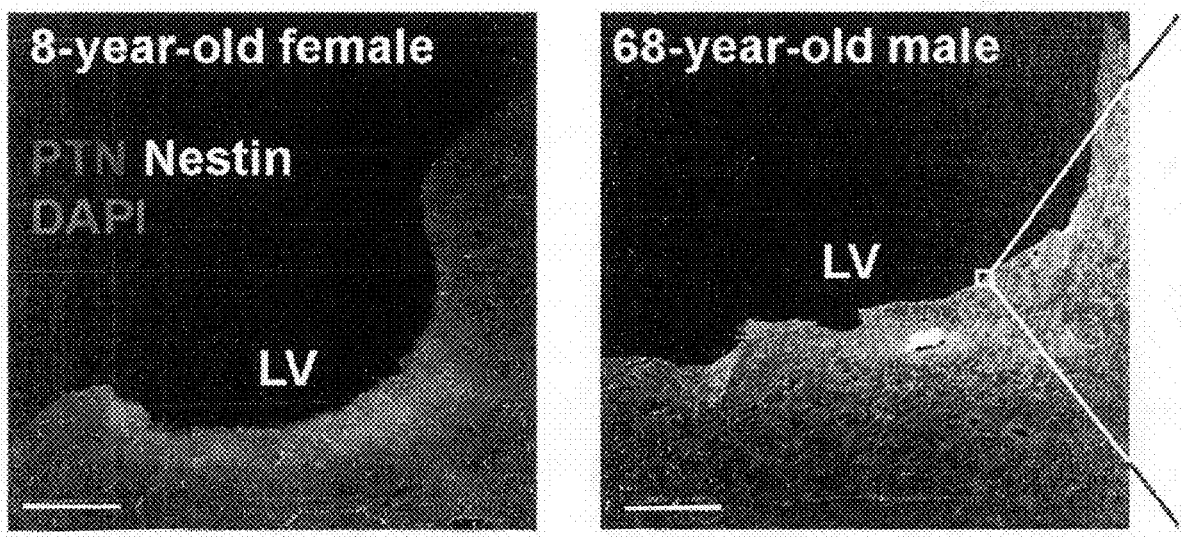
Figure 5D:
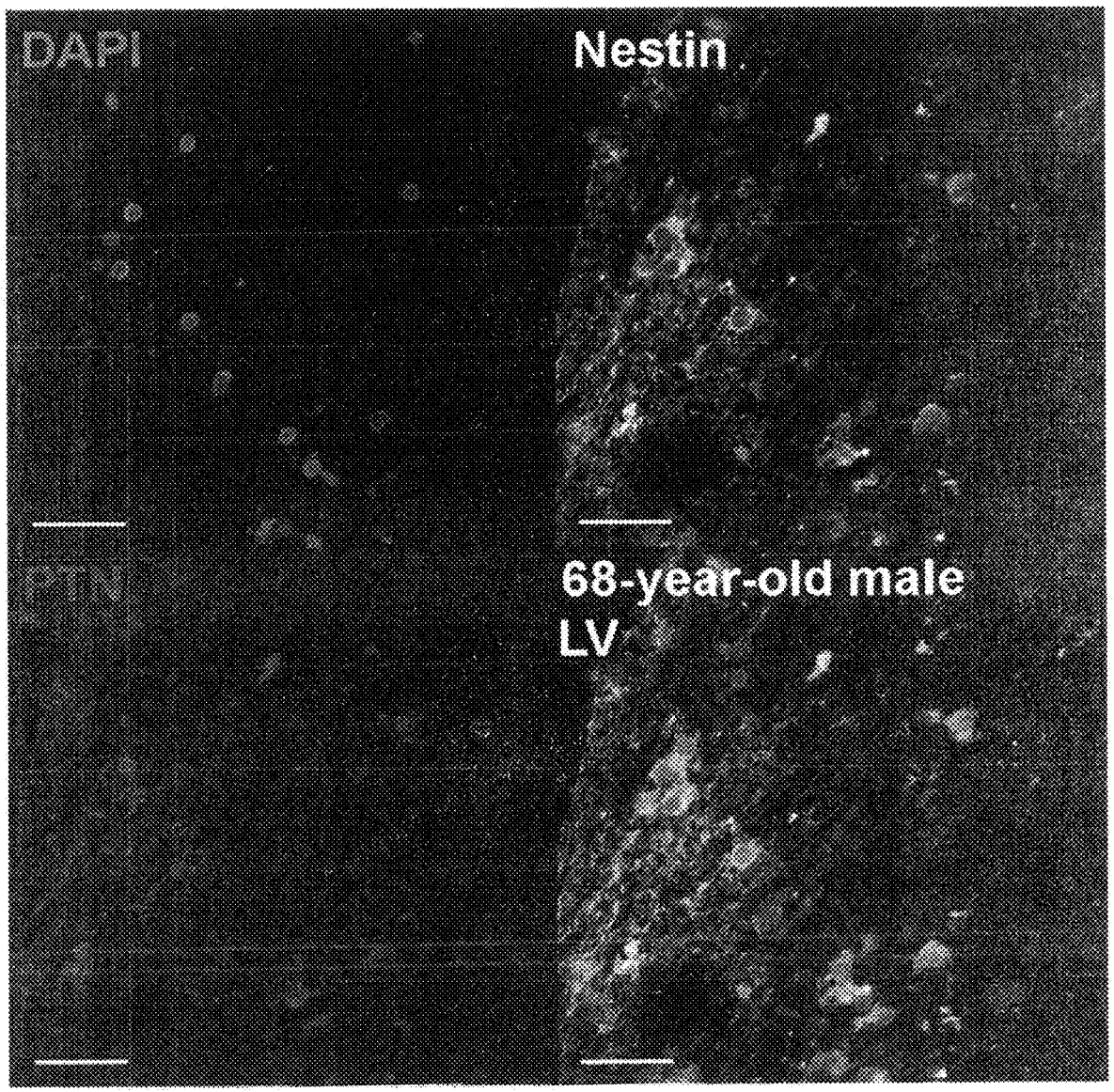
Figure 5E:
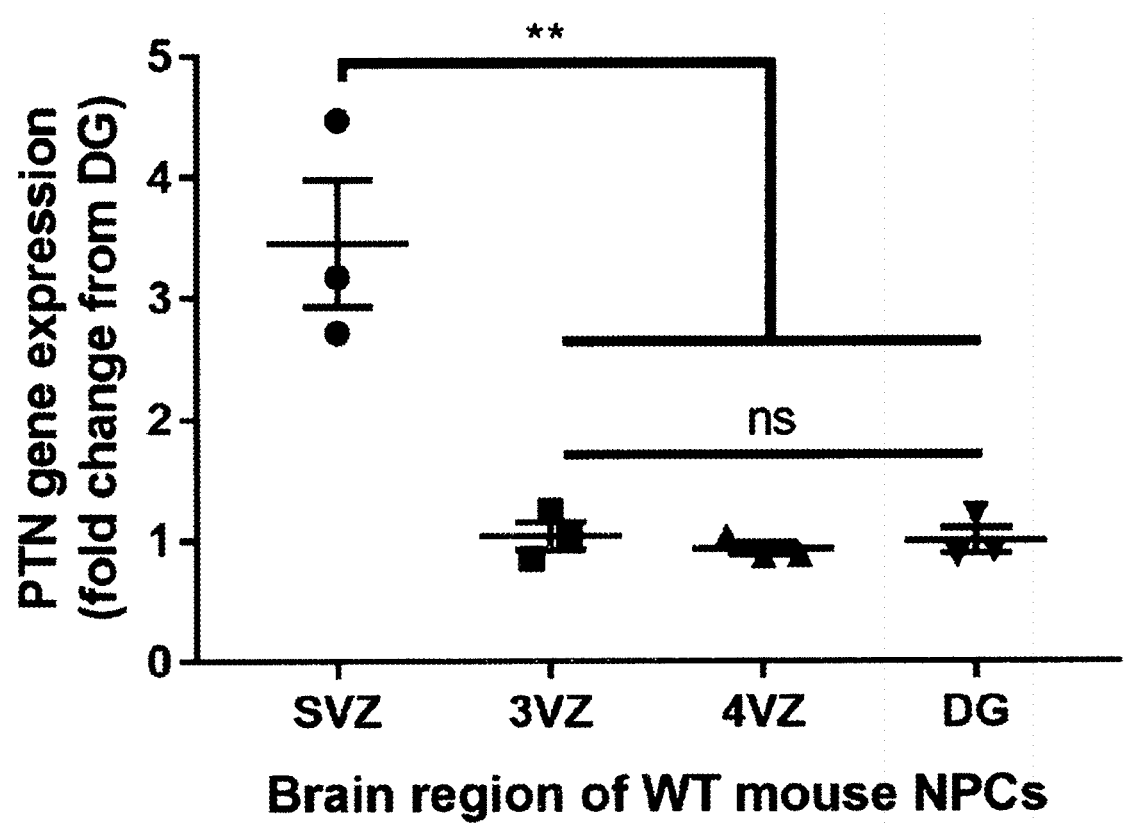
Figure 5F:
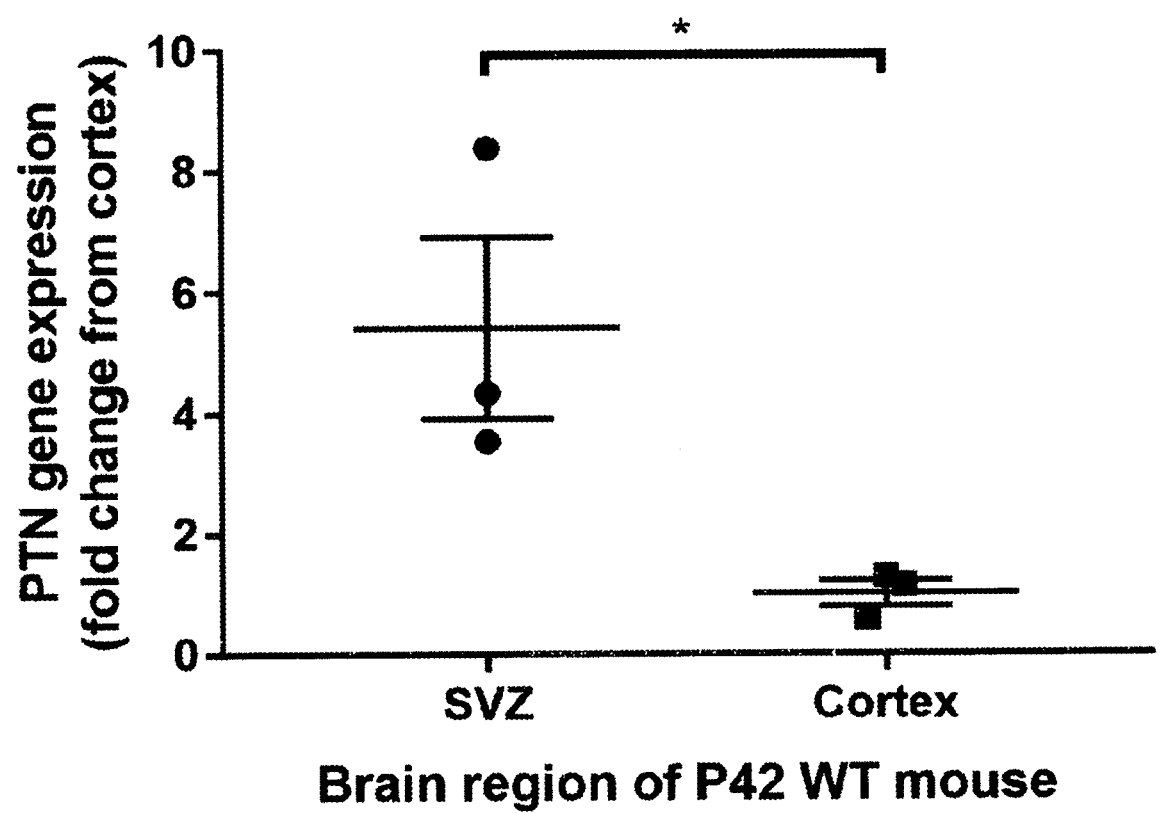
Figure 5G:
Figure 5H:
Figure 11A:
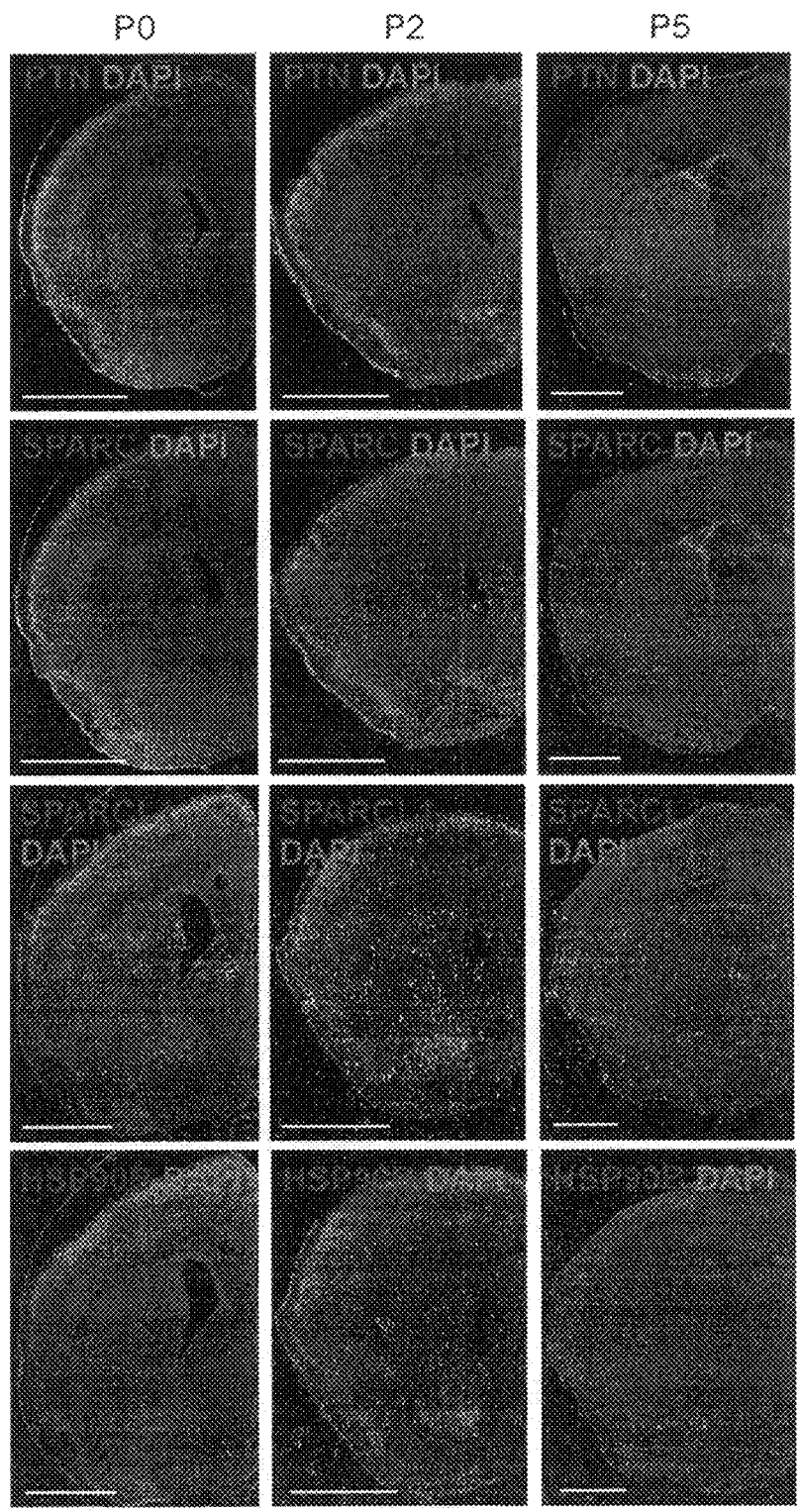
FIGS. 11A and 11B show expression of PTN and its binding partners (related to FIG. 5). Expression of PTN, SPARC, SPARCL1, and HSP90B around the lateral ventricles in postnatal mice ages P0, P2, and P5, (FIG. 11A) and P10, P14, and P21 (FIG. 11B). PTN is more broadly expressed in the forebrain in P0-P5 mice, and becomes more restricted to the SVZ by P10. PTN is also expressed in the pia mater. SPARC, SPARCL1, and HSP90B are more broadly expressed in the brain.
Figure 11B:
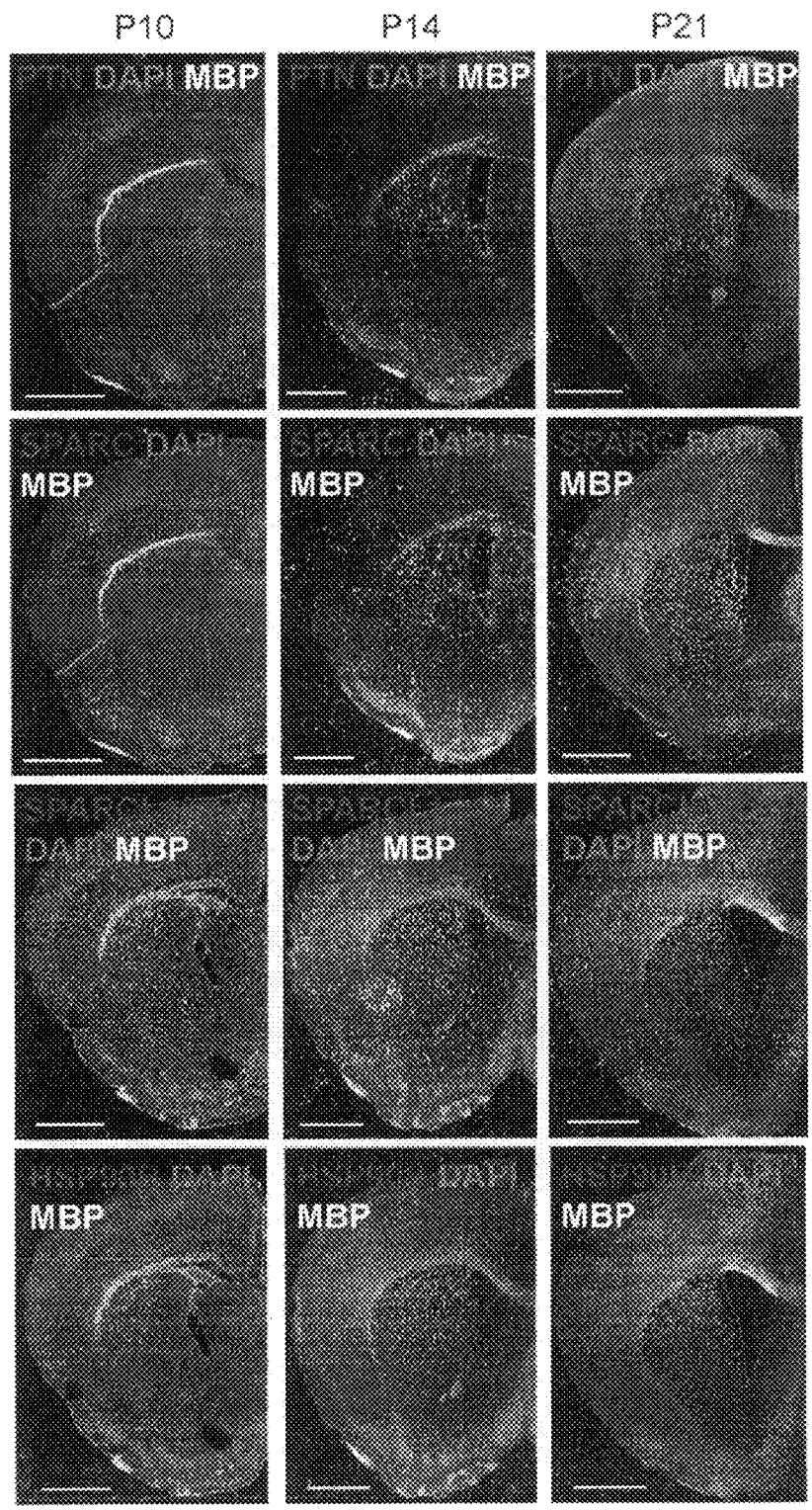

Expression of Pleiotrophin is Strongly Enriched in the Mouse and Human Postnatal SVZ The role of pleiotrophin in glioma invasion of the SVZ is of particular interest, as it has been found to promote neurite outgrowth and neuroblast migration during neurodevelopment (Li et al. (1990) Science 250, 1690-1694; Rauvala and Pihlaskari (1987) J. Biol. Chem. 262, 16625-16635; Maeda and Noda (1998) J. Cell Biol. 142(1), 203-216), as well as migration of adult GBM cells through autocrine/paracrine mechanisms (Lu et al. (2005) J. Biol. Chem. 280, 26953-26964; Ulbricht et al. (2003) J. Neuropathol. Exp. Neurol. 62, 1265-1275). We found that PTN protein expression is enriched in the SVZ stem cell niche compared to other brain regions, with PTN expression strongest in the lateral ventricle SVZ, particularly in the lateral walls, and is less strongly expressed in the third and fourth ventricular zone in the adult murine brain (FIG. 5A). In the developing postnatal murine brain, we found that PTN protein is more broadly expressed in the brain at P0-5, and becomes largely restricted to the lateral ventricle SVZ by P10 (FIGS. 5B, 11A). PTN protein is also expressed in the pia mater, which is interesting to note as HGGs can also spread to the leptomeninges; in DIPG, leptomeningeal spread has been observed in 25-30% of cases at the time of autopsy (Caretti et al (2014) Acta Neuropathol. 128, 605-607; FIGS. 5B, 11A). Of the four identified proteins, PTN is the most localized to the SVZ after early postnatal development in mice, whereas SPARC, SPARCL1, and HSP90B are more broadly expressed in the brain (FIG. 11A). In the childhood and adult human SVZ, we found strong PTN expression specific to the first few millimeters subjacent to the ventricular epithelium and expression co-localized with Nestin$^+$ NPCs as well as extracellularly (FIGS. 5C, 5D). NPCs isolated from the murine lateral ventricle SVZ at P14 exhibited higher gene and protein expression of PTN compared to NPCs isolated at the same age from the 3VZ, 4VZ, or hippocampal dentate gyrus (another neural stem cell niche; FIGS. 5E, 5G). Whole SVZ tissue isolated from P42 mice also exhibited higher gene and protein expression of PTN compared to cortical tissue (FIGS. 5F, 5H). These results demonstrate the specific enrichment of PTN in murine and human postnatal SVZ NPCs, suggesting that this molecule could mediate NPC:glioma chemoattraction and underlie the pattern of SVZ invasion observed clinically. Together, these results suggest that PTN is a primary factor responsible for the chemoattraction toward SVZ hNPC CM, and that the other three proteins act as accessory factors.

PTN is Necessary for Glioma Invasion Toward the SVZ

Figure 6A:
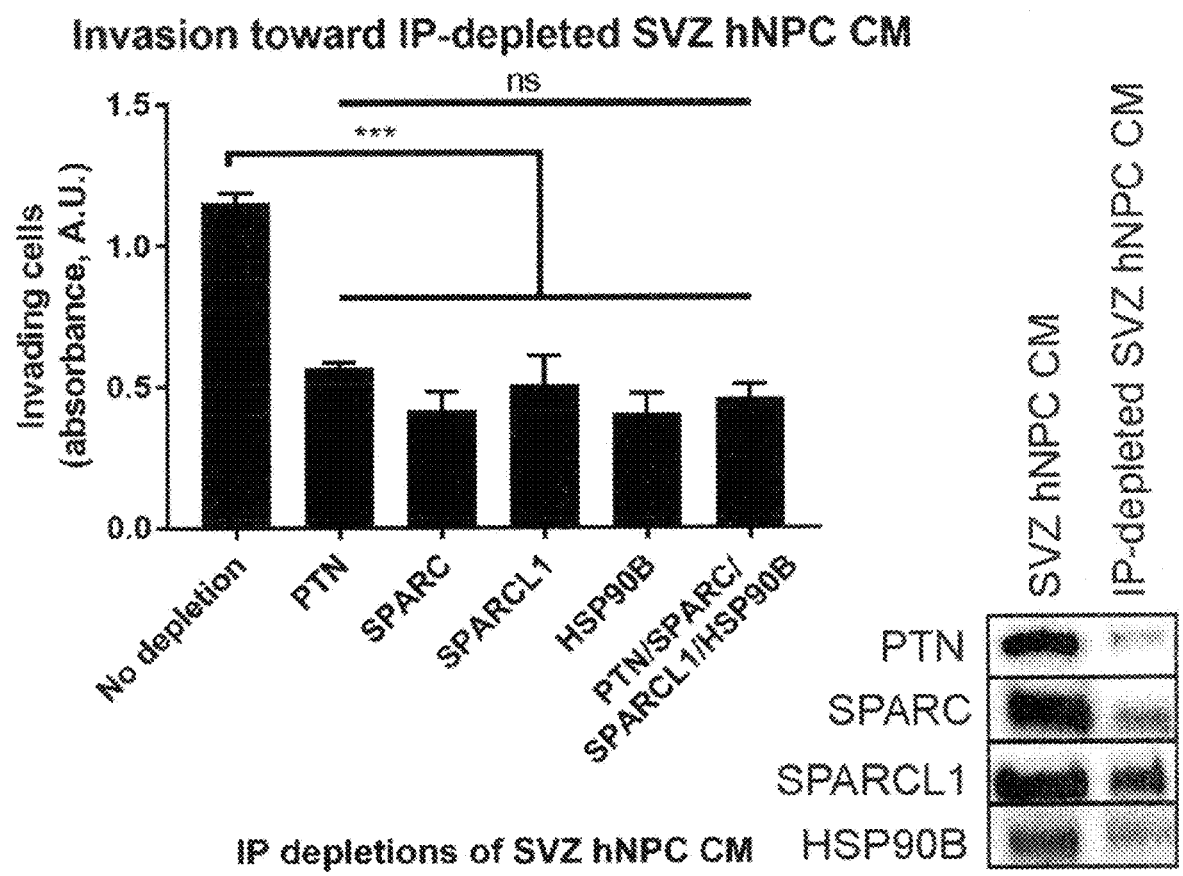
FIGS. 6A-6F show that PTN is necessary for glioma invasion toward the SVZ.
Figure 6B:
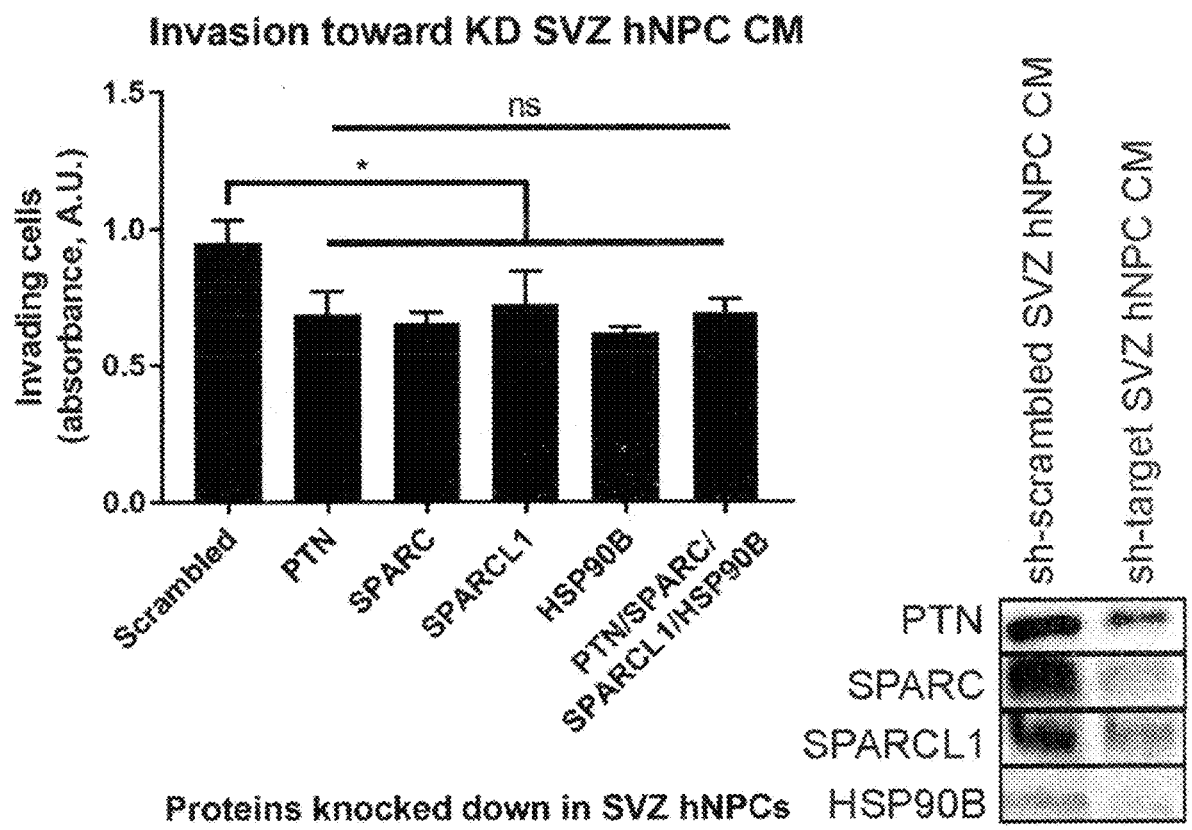
Figure 12A:
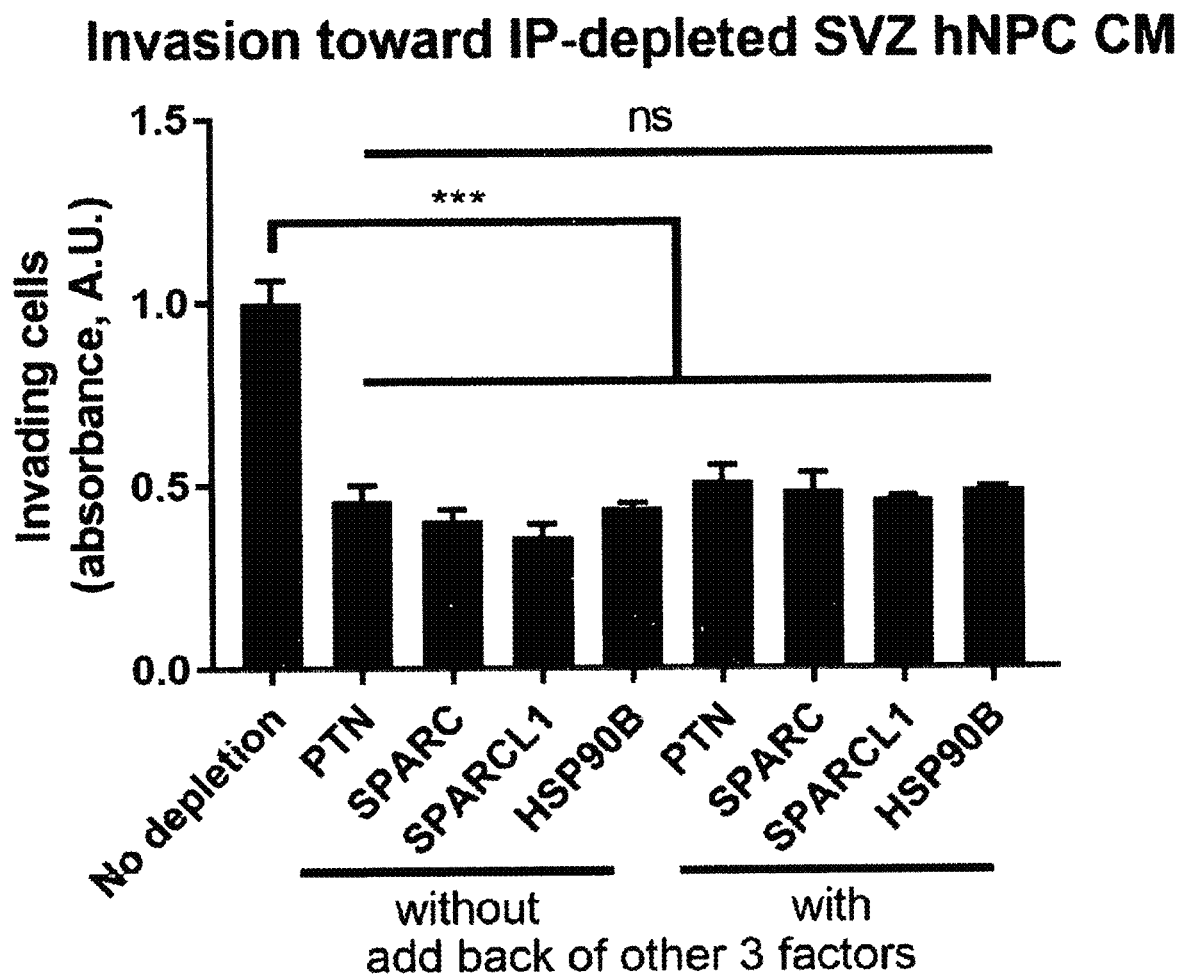
FIGS. 12A-12J show that knock down of PTPRZ1 decreases tumor engraftment and invasion of the SVZ (related to FIG. 6).

To test the necessity of the PTN complex for DIPG invasion toward SVZ NPCs, we depleted each factor from SVZ hNPC CM by two different methods. Immunodepletion of any of the four proteins (with or without add back of the other three proteins) abrogated the chemoattractant effect of the CM (FIGS. 6A, 12A). shRNA-mediated knockdown of SVZ hNPC gene expression of any of the four genes decreased DIPG cell invasion toward CM from those NPCs (FIG. 6B). These results indicate that each of the four proteins is necessary for DIPG invasion toward SVZ NPCs in vitro.

Figure 6C:
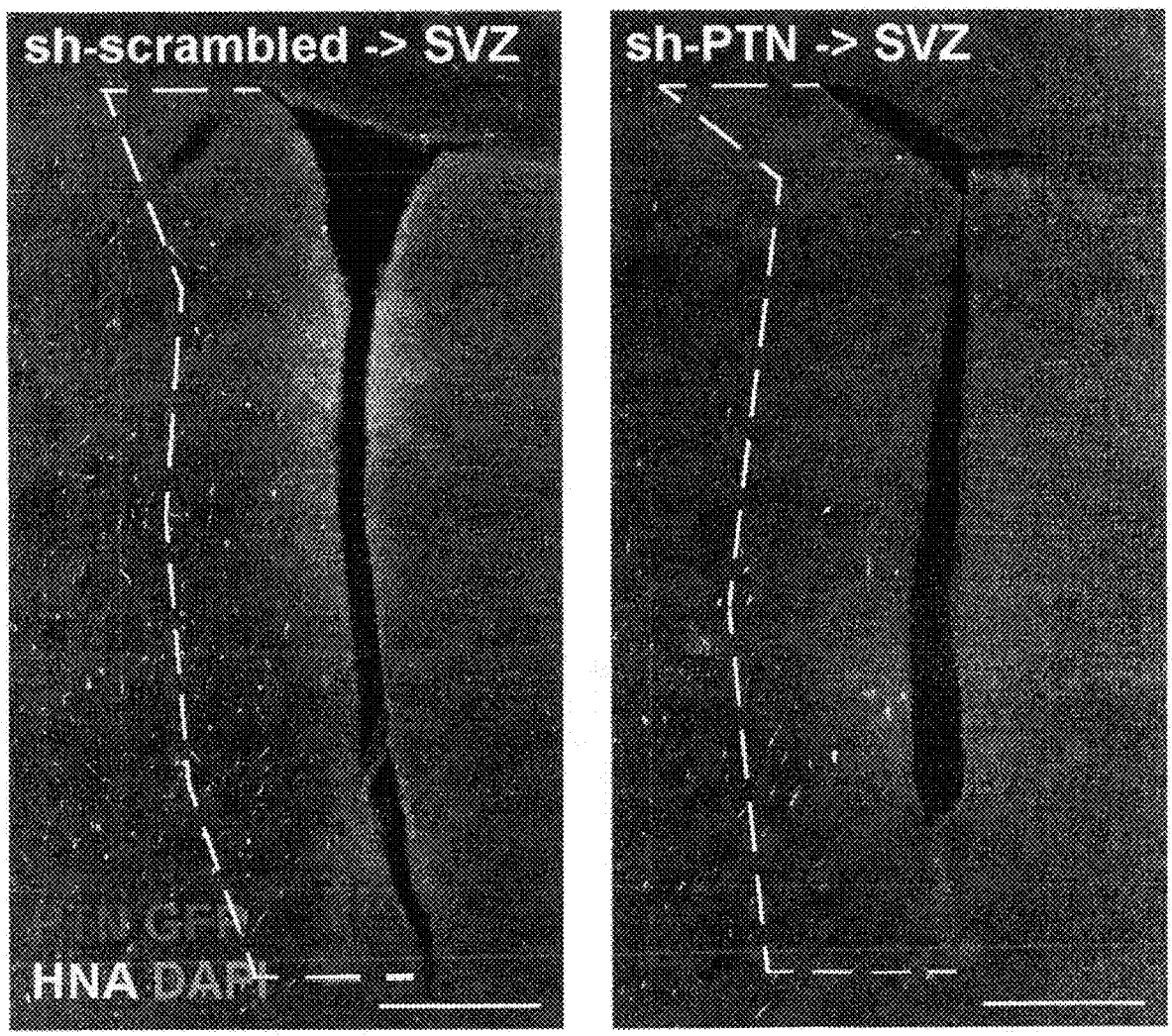
Figure 6D:
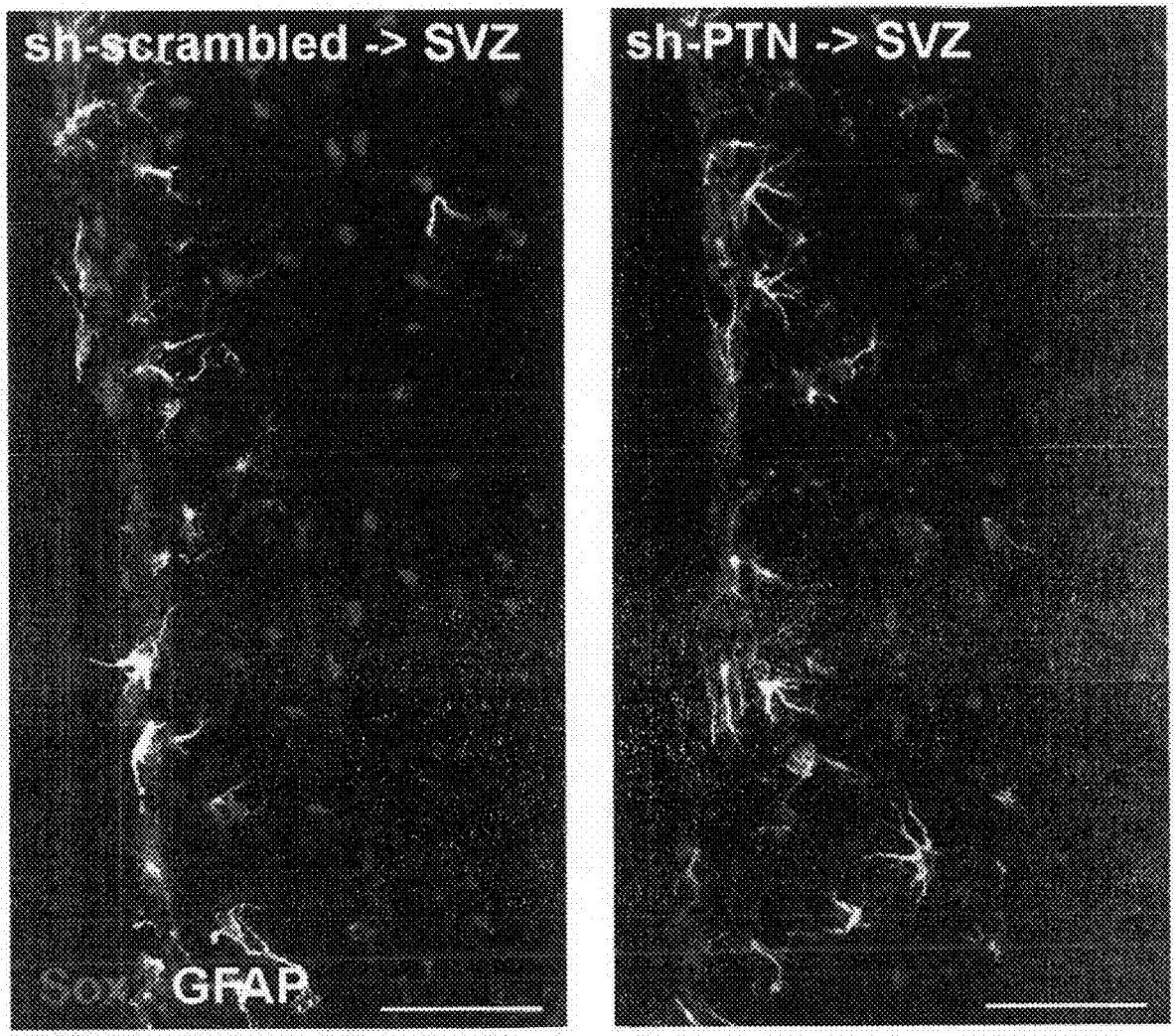
Figure 6E:
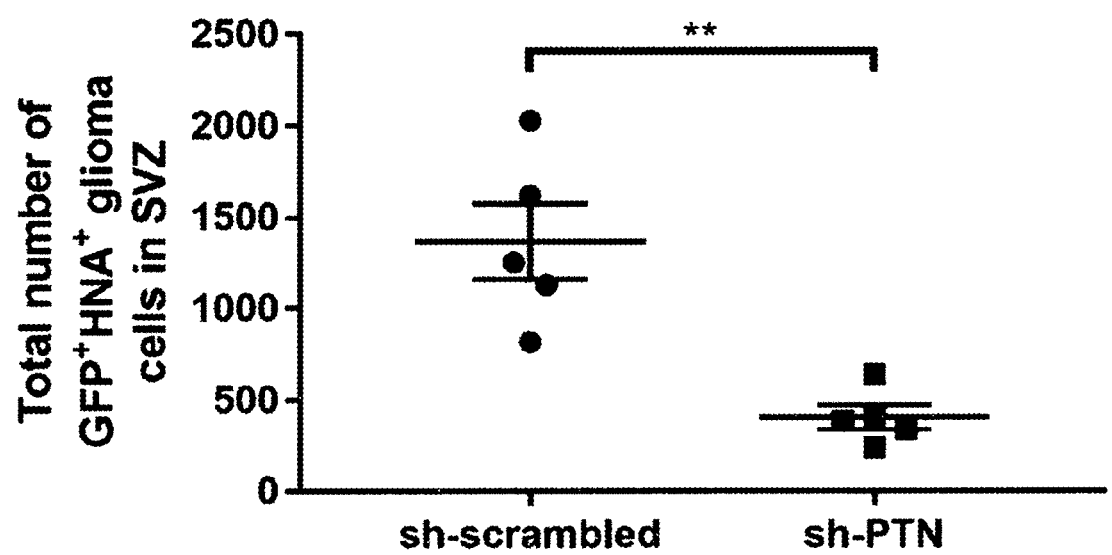
Figure 6F:
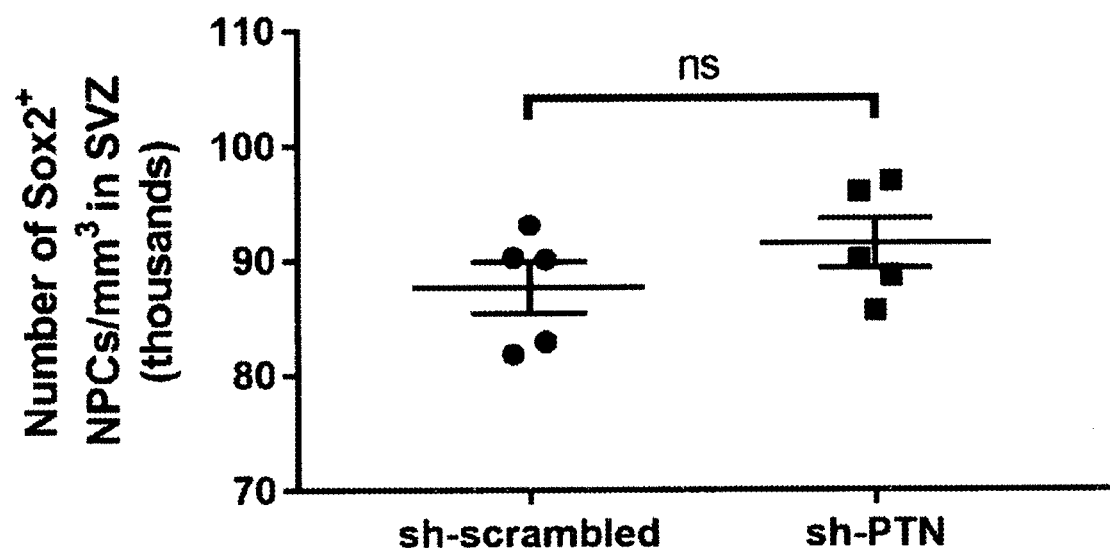
Figure 12B:
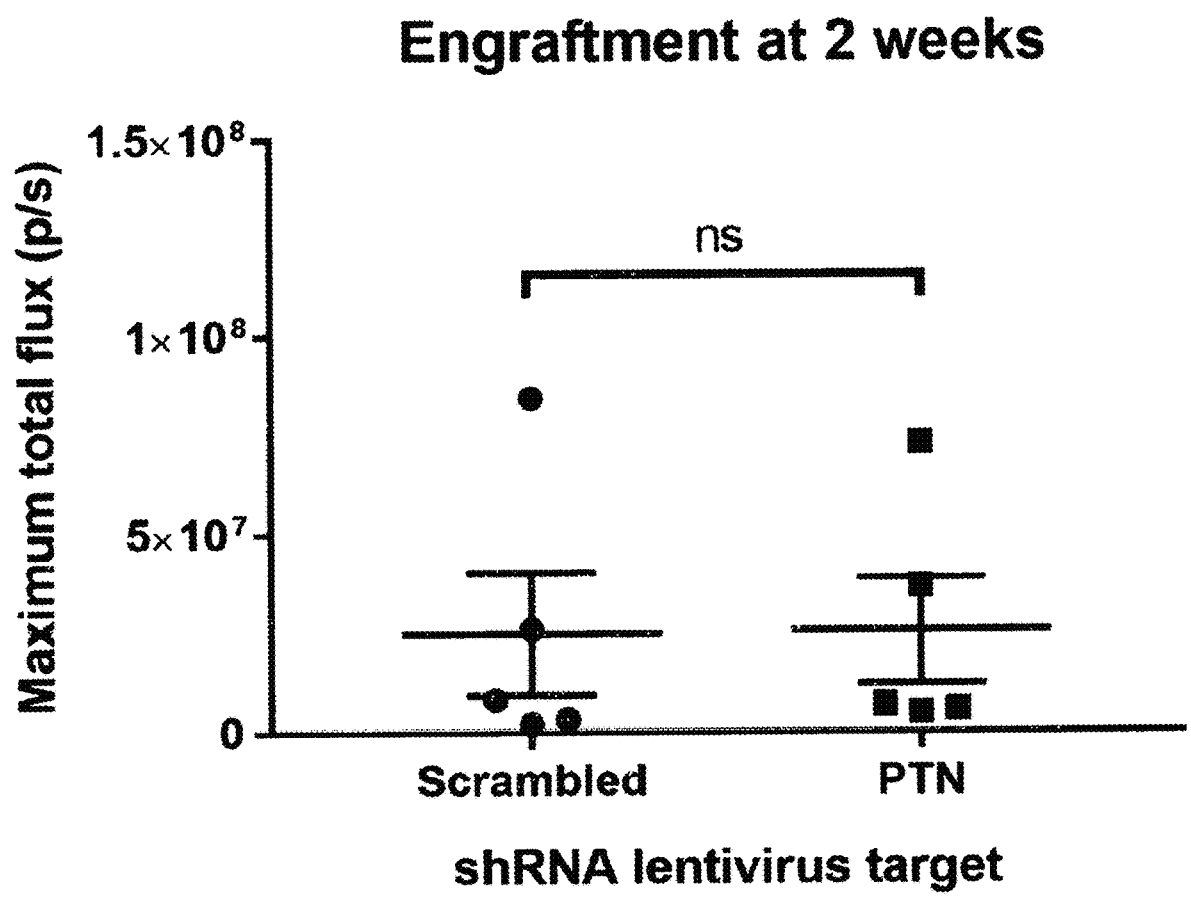
Figure 12C:
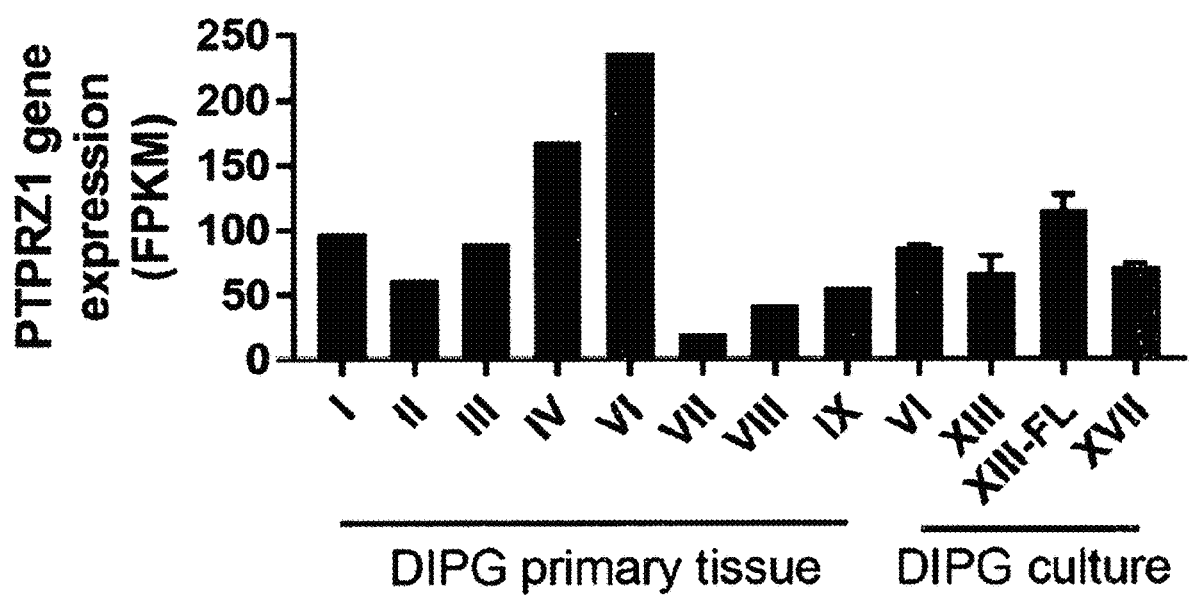
Figure 12D:
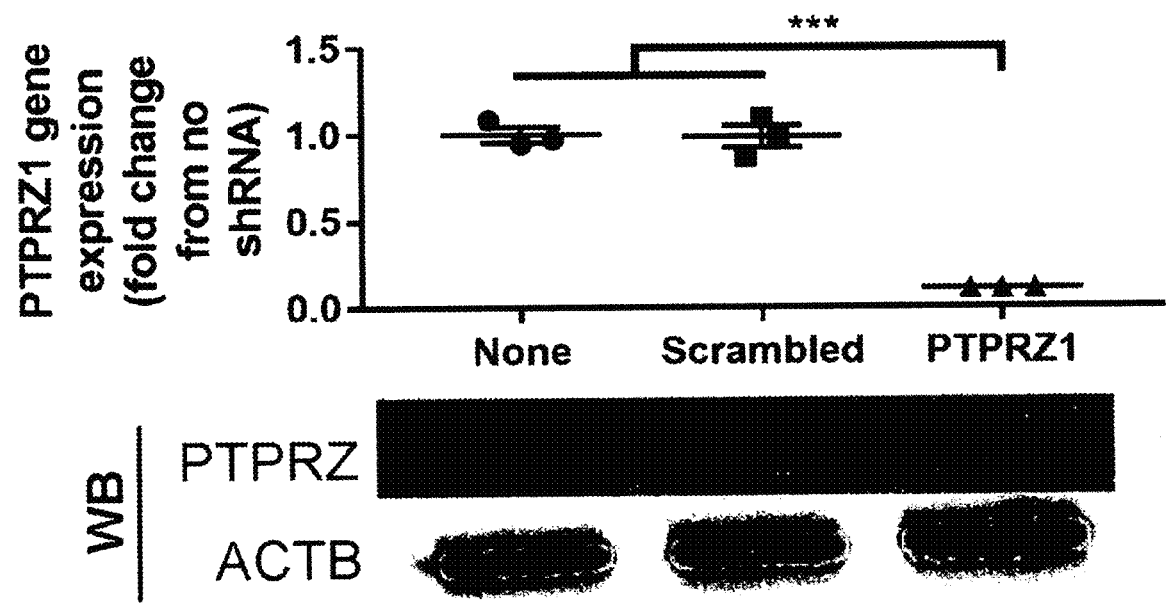
Figure 12E:
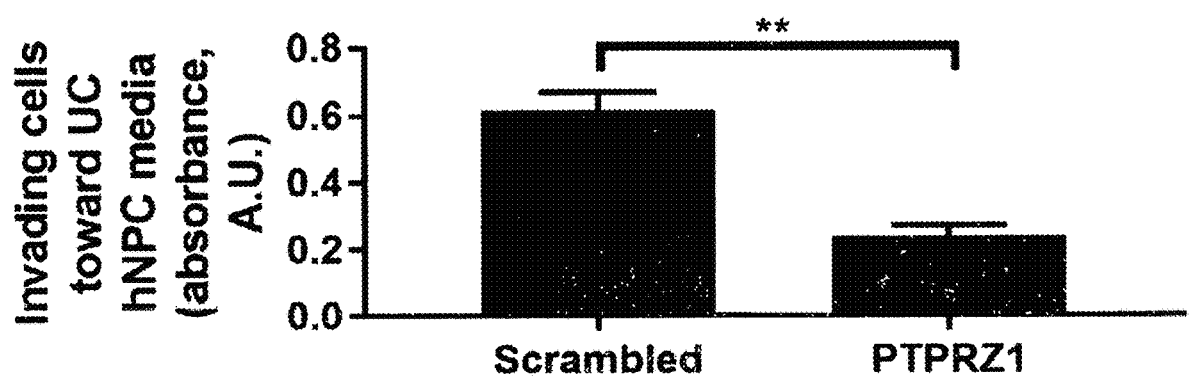
Figure 12F:
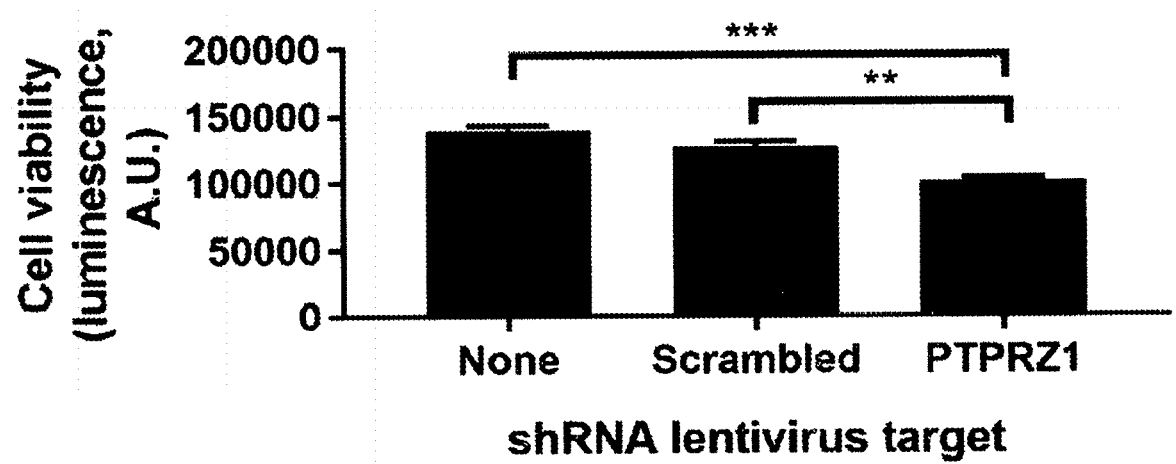
Figure 12G:
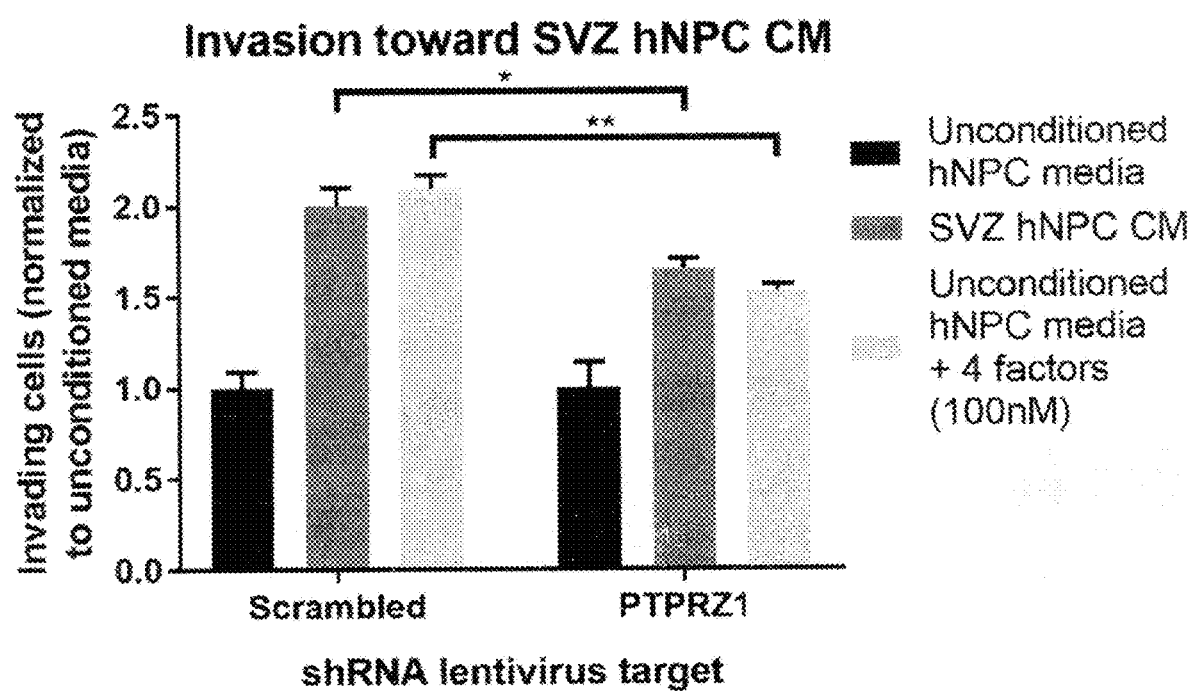
Figure 12H:
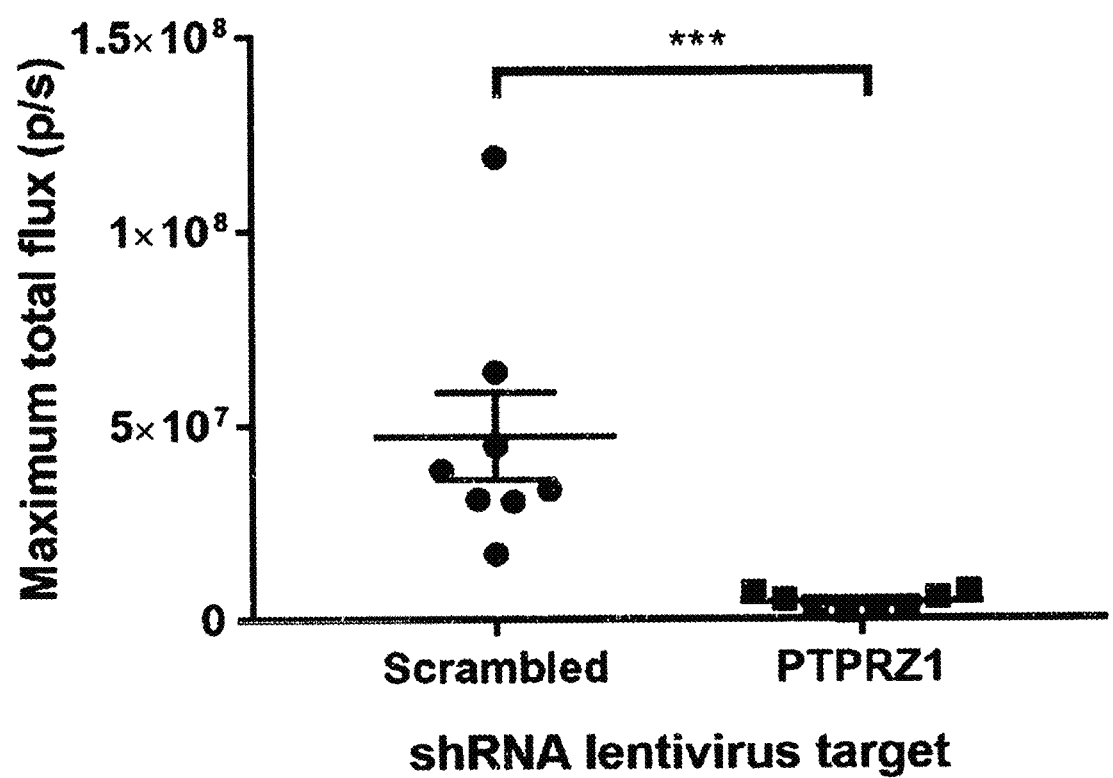
Figure 12I:
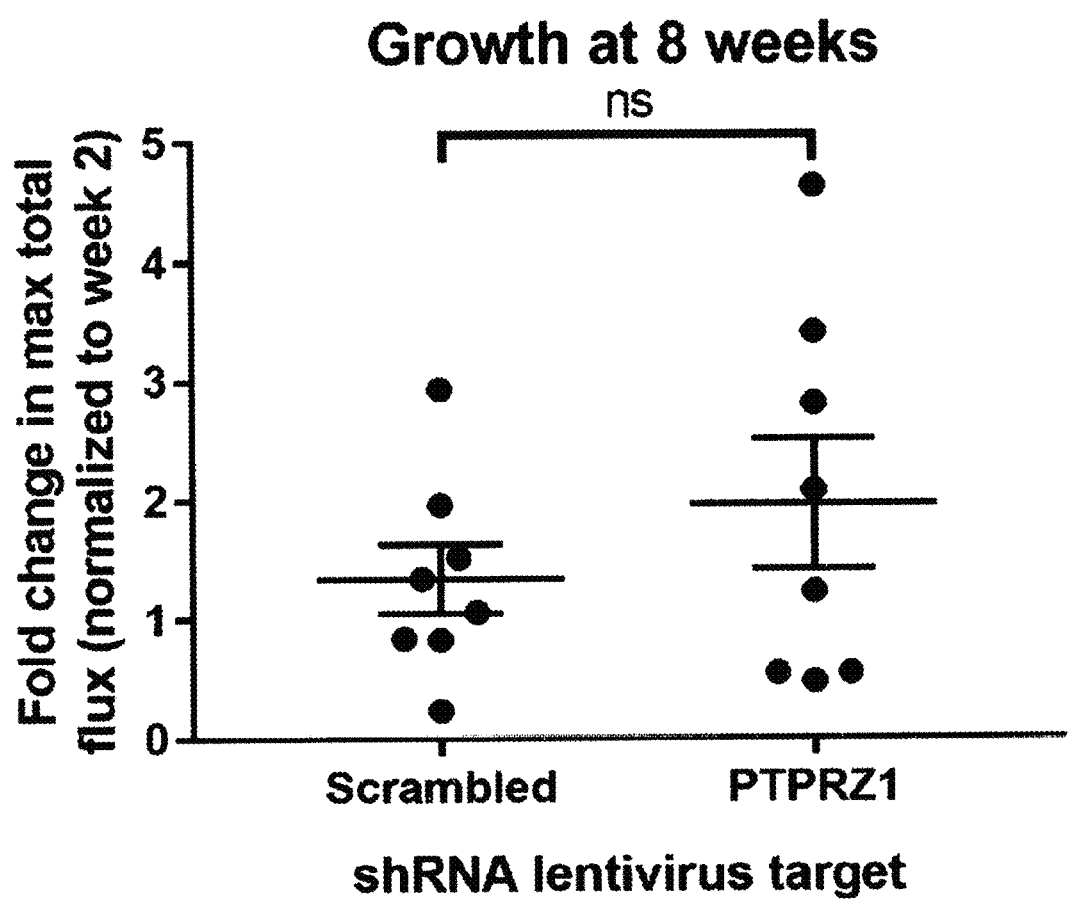
Figure 12J:
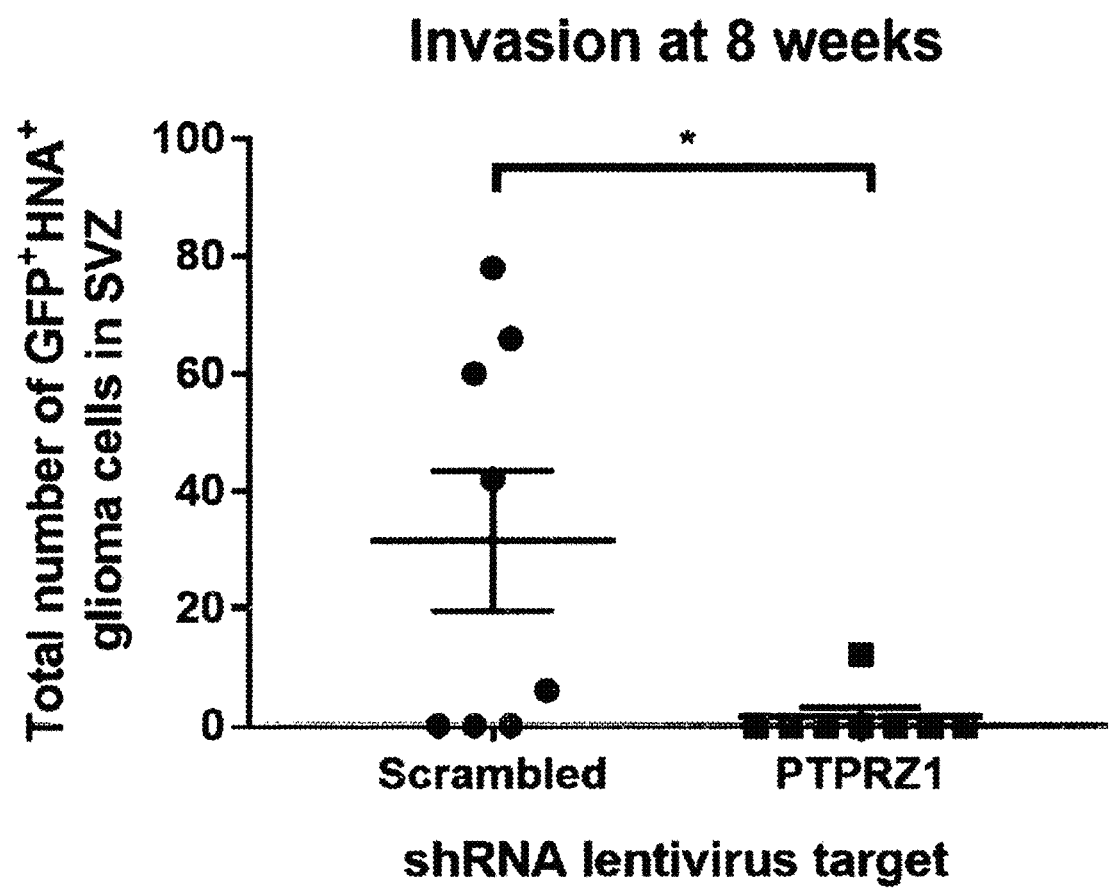

We then tested the necessity of pleiotrophin for DIPG invasion of the SVZ in vivo. Stereotactic injection of lentivirus expressing shRNA targeting Ptn into the mouse SVZ achieved effective knockdown of pleiotrophin expression, compared to a non-targeting scrambled shRNA control (FIG. 6C). Tumor engraftment in the two groups was equivalent (FIG. 12B). At 16 weeks following pontine xenograft, we found that fewer DIPG cells invaded the SVZ in mice with shRNA-mediated knockdown of Ptn in the SVZ, compared to mice that received a scrambled shRNA control (FIGS. 6C, 6E). While the role of pleiotrophin in postnatal SVZ NPCs remains to be elucidated, we assessed the number of SVZ NPCs present following Ptn knockdown to confirm that the striking decrease in SVZ glioma invasion was not explained by a reduction in the NPC population. We found equivalent numbers of Sox2$^+$ NPCs in mice injected with Ptn shRNA or scrambled shRNA control vectors (FIGS. 6D, 6F), confirming that the observed reduction in glioma invasion was not due to NPC loss but rather to decreased Ptn expression. Taken together, these data demonstrate that PTN is necessary for glioma invasion toward the SVZ NPC niche in vitro and in vivo. Pleiotrophin has several known receptors, and the one that has been implicated in glioma migration is protein tyrosine phosphatase receptor type ζ (PTPRZ; Lu et al. (2005) J. Biol. Chem. 280, 26953-26964; Müller et al. (2003) Oncogene 22, 6661-6668; Ulbricht et al., supra). DIPG primary tumor and cell culture samples exhibit expression of the protein tyrosine phosphatase receptor type ζ gene PTPRZ1 (Grasso et al. (2015) Nat. Med. 21, 555-559; Nagaraja et al. (2017) Cancer Cell 31, 635-652.e6; FIG. 12C). Robust shRNA-mediated knockdown of PTPRZ1 expression in DIPG cells (FIG. 12D) substantially decreases baseline invasion (FIG. 12E) and also mildly decreases cell viability (FIG. 12F). Normalizing for these effects, we find that PTPRZ1 knockdown in DIPG cells confers a partial abrogation of invasion toward SVZ hNPC CM or the PTN complex in vitro (FIG. 12G). This suggests that while PTPRZ is necessary for the full effect of the PTN complex, other receptors may also be involved. To further test the hypothesis that PTPRZ is a relevant PTN receptor to SVZ invasion, PTPRZ1 knockdown or scrambled control DIPG cells were xenografted to the pons. We found a dramatic effect on engraftment, with PTPRZ1 knockdown resulting in 10-fold lower bioluminescent signal on initial IVIS imaging (FIG. 12H). From these different initial tumor sizes, the rate of growth was similar in mice xenografted with PTPRZ1 knockdown or control cells (FIG. 12I). At 8 weeks, significantly fewer cells expressing PTPRZ1 shRNA reached the SVZ (FIG. 12J), but interpretation of these results is complicated by the substantial effect of PTPRZ1 knockdown on DIPG xenograft engraftment.

HSP90 Inhibition as a Potential Therapeutic Strategy

Figure 13A:
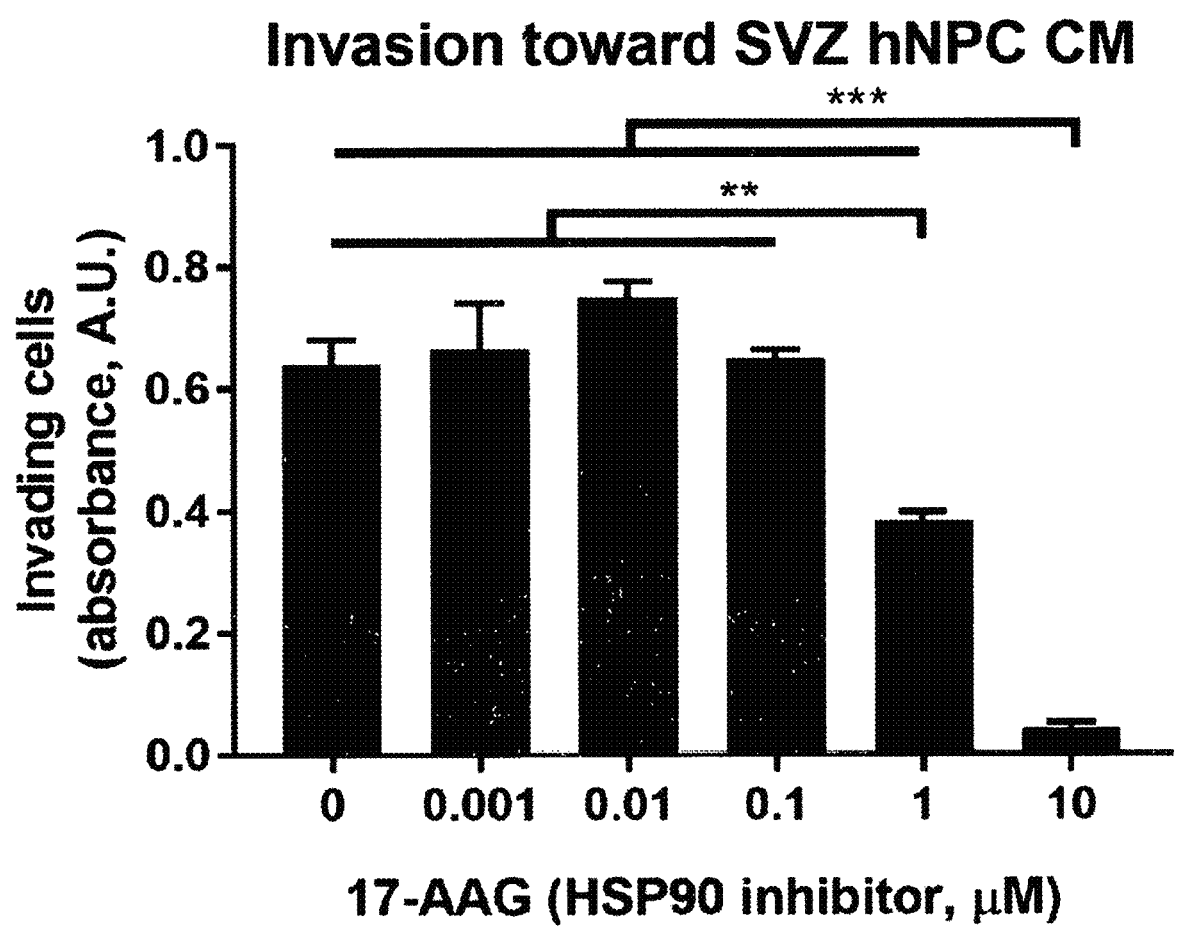
FIGS. 13A-13F show inhibition of HSP90 by drug and shRNA lentivirus (related to FIG. 6).
Figure 13B:
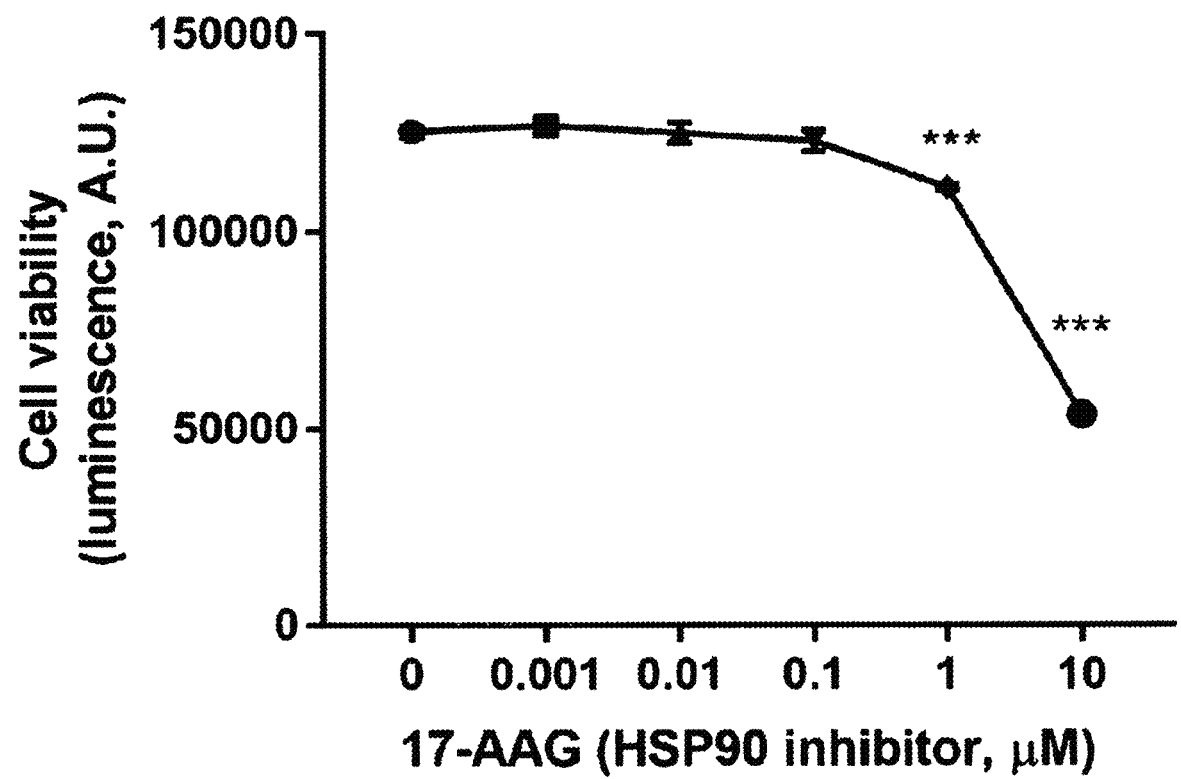
Figure 13C:
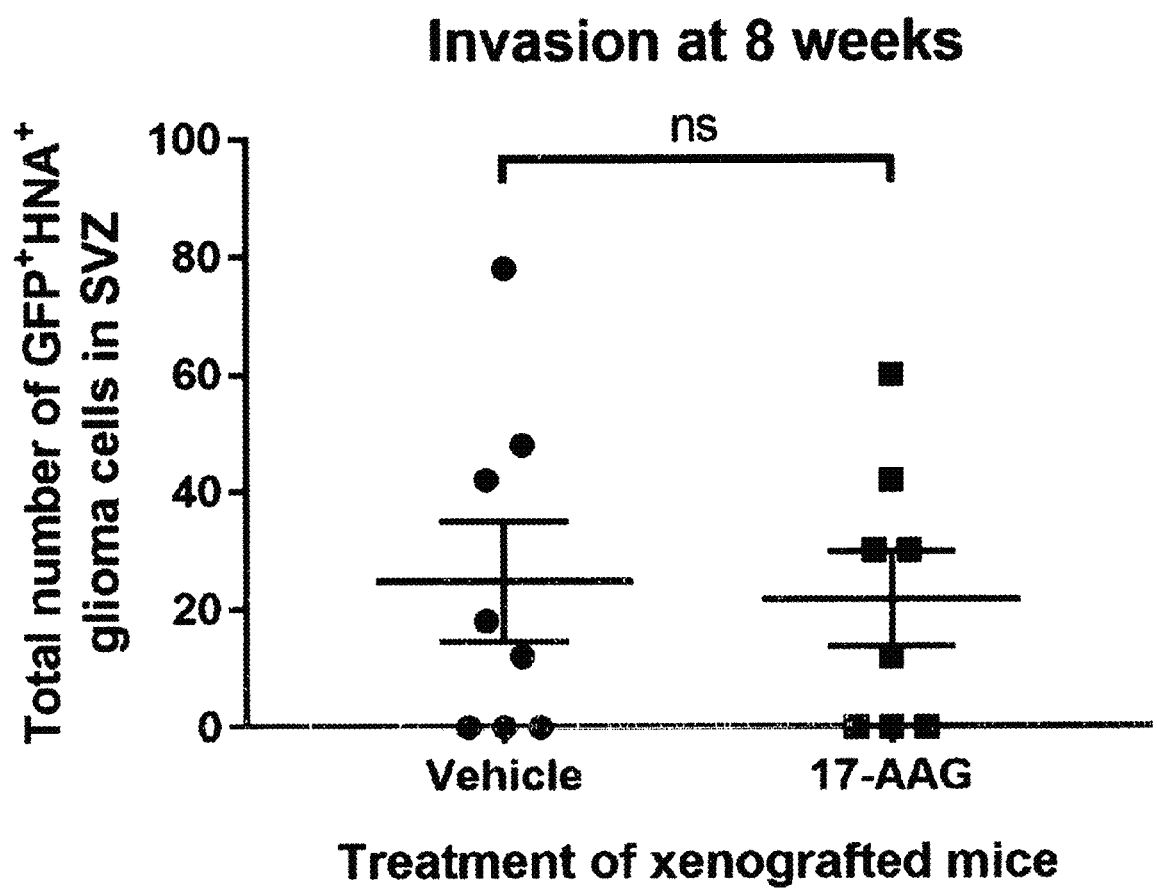
Figure 13D:
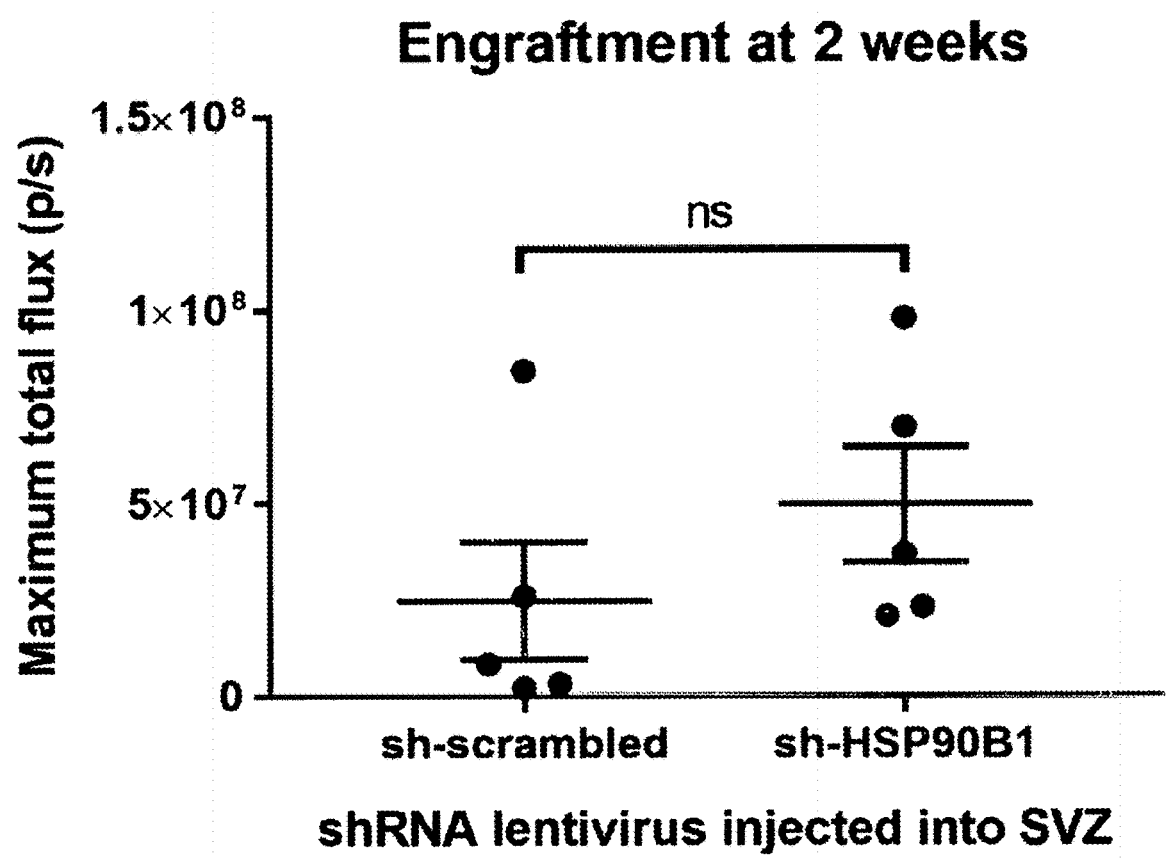
Figure 13E:
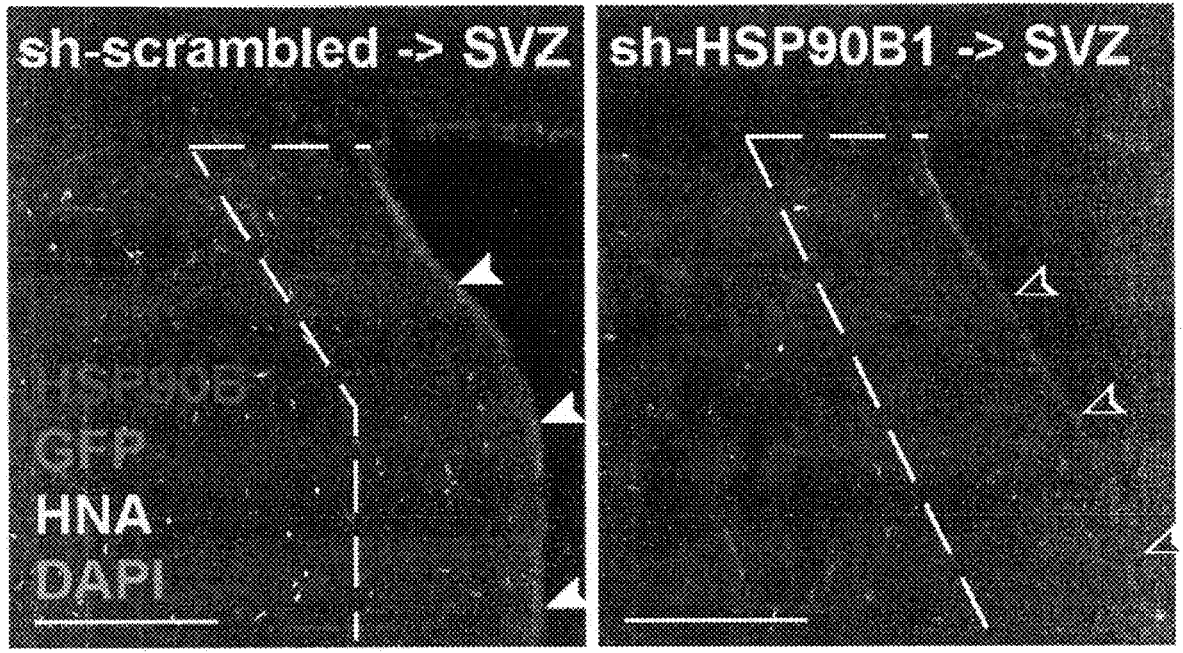
Figure 13F:
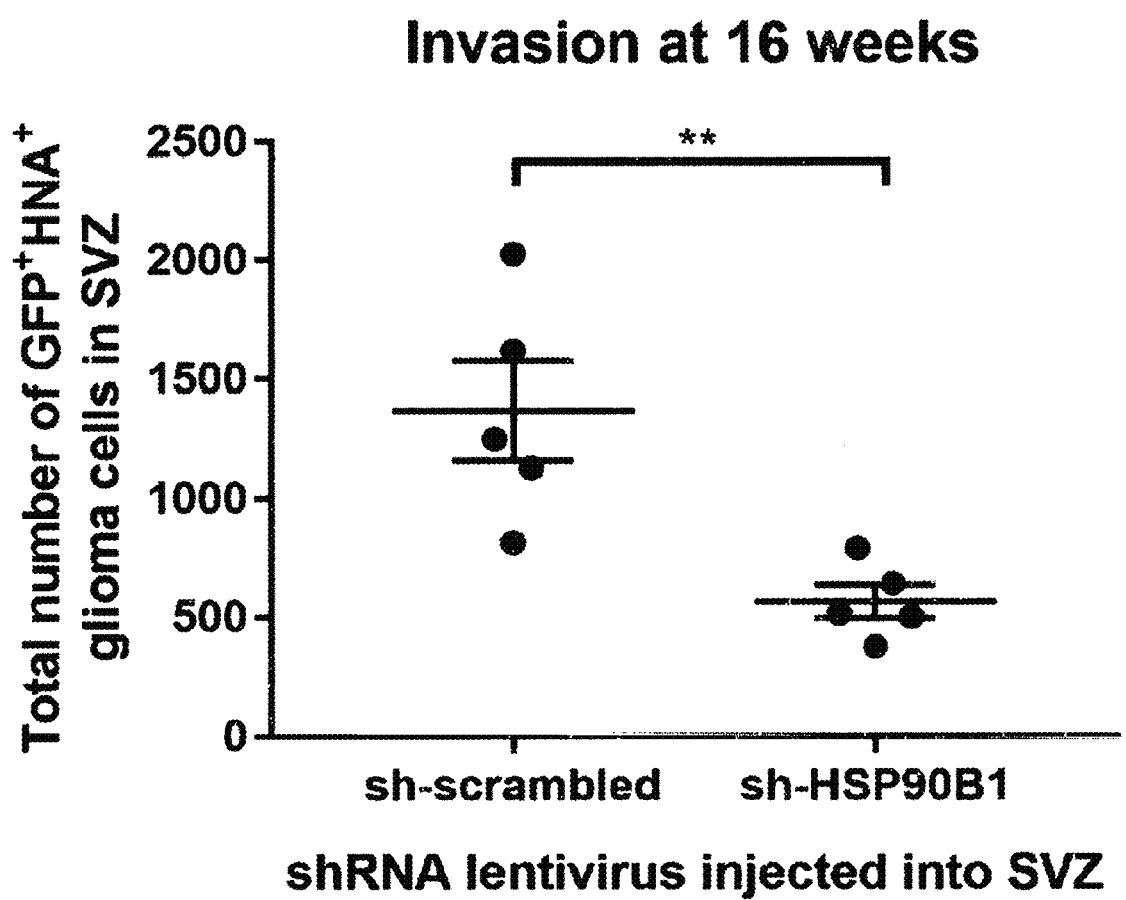

Because HSP90 is a necessary component of the PTN complex, and HSP90 inhibitors have been developed for clinical use, we tested the possibility that HSP90 inhibition could be used as a strategy to reduce SVZ invasion. Evaluating an HSP90 inhibitor (tanespimycin, 17-AAG) that has been in advanced clinical trials, we found that 17-AAG decreases invasion toward SVZ hNPC CM in vitro, but only at concentrations above 1 µM (FIGS. 13A-13B). At high concentrations, 17-AAG also decreased DIPG cell viability, as has been reported for other HSP90 inhibitors (Grasso et al, supra). Brain penetration of 17-AAG has been measured at less than 1 µM in rodent models (Egorin et al. (2001) Pharmacol. 47, 291-302), so we did not expect to find a therapeutic effect in vivo. Accordingly, we did not find a difference in SVZ invasion between mice that received 17-AAG following pontine xenograft compared to those receiving vehicle control (FIG. 13C). Because HSP90 targeting with a more potent or brain penetrant antagonist may be a useful strategy, we sought proof of principle demonstration that HSP90 inhibition could decrease SVZ invasion. Stereotactic injection of shRNA-expressing lentivirus targeting the HSP90B1 gene into the mouse SVZ resulted in fewer DIPG cells invading the SVZ at 16 weeks following pontine xenograft, with no effect on initial tumor engraftment (FIGS. 13D-13F). These results support the concept that HSP90B is necessary for DIPG invasion of the SVZ and that effective HSP90 inhibition could prove a useful strategy.

NPC-Secreted Factors Activate the Rho/ROCK Pathway

Figure 7A:
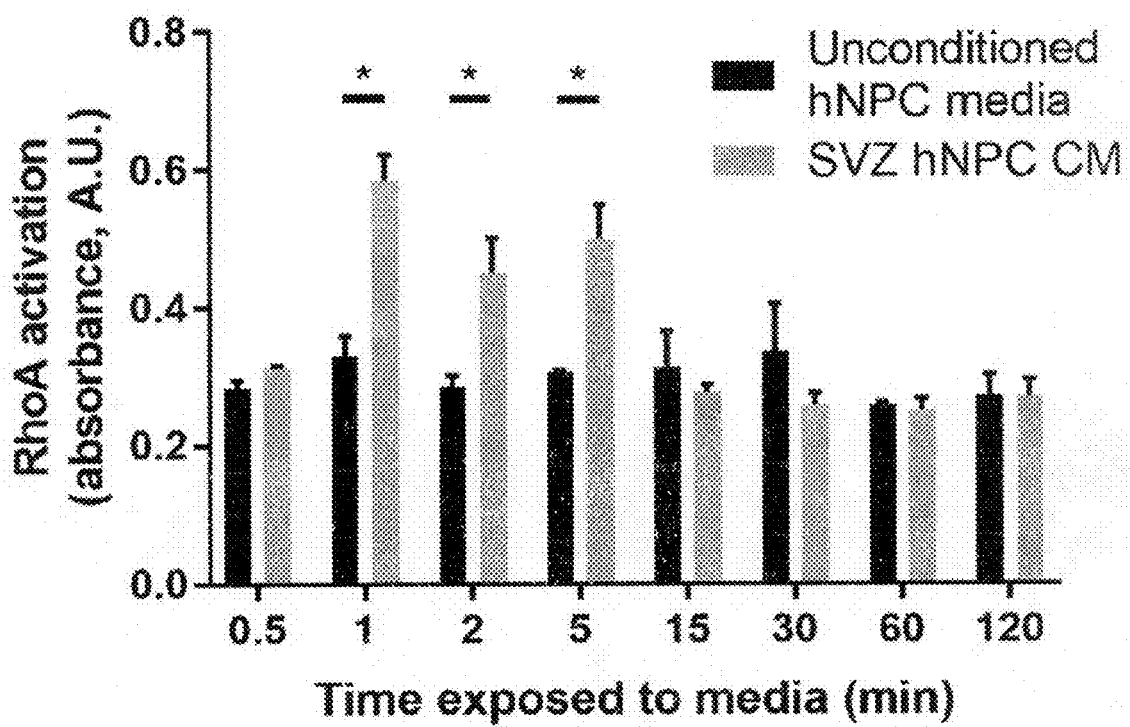
FIGS. 7A-7H show that NPC-secreted factors activate the Rho/ROCK pathway.

The Rho/Rho kinase (ROCK) pathway is linked to PTN-PTPRZ signaling (Fujikawa et al. (2011) J. Biol. Chem. 286, 37137-37146; Kuboyama et al. (2012) PLoS One 7, e48797; Niisato et al. (2005) J. Neurosci. 25, 1081-1088; Tamura et al. (2006) Neurosci. Lett. 399, 33-38) and to tumor invasion in general (for review, see Parri and Chiarugi (2010) Cell Commun Signal 8, 23). To test the involvement of this pathway in DIPG invasion of the SVZ, we exposed DIPG cells to unconditioned hNPC media or SVZ hNPC CM for a range of time points between 0.5-120 minutes, and subsequently measured RhoA and ROCK activation of the DIPG cells. Exposure to SVZ hNPC CM for 1-5 minutes resulted in an increase in RhoA activation compared to exposure to unconditioned hNPC media (FIG. 7A).

Figure 7B:
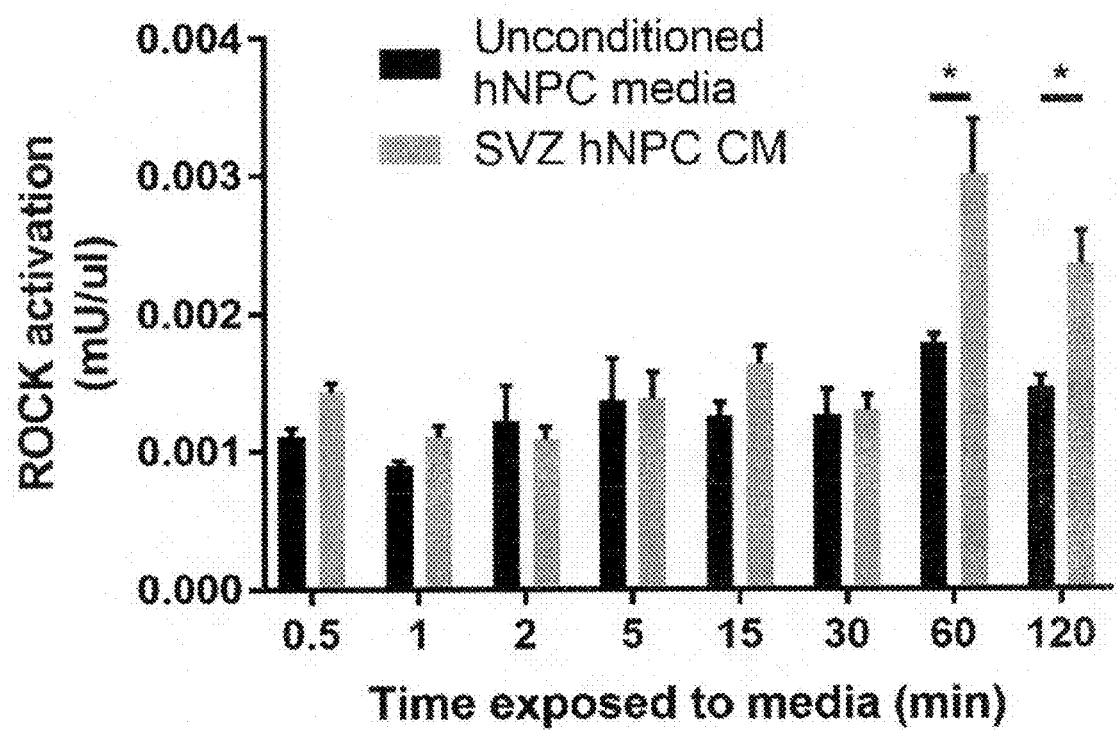
Figure 7C:
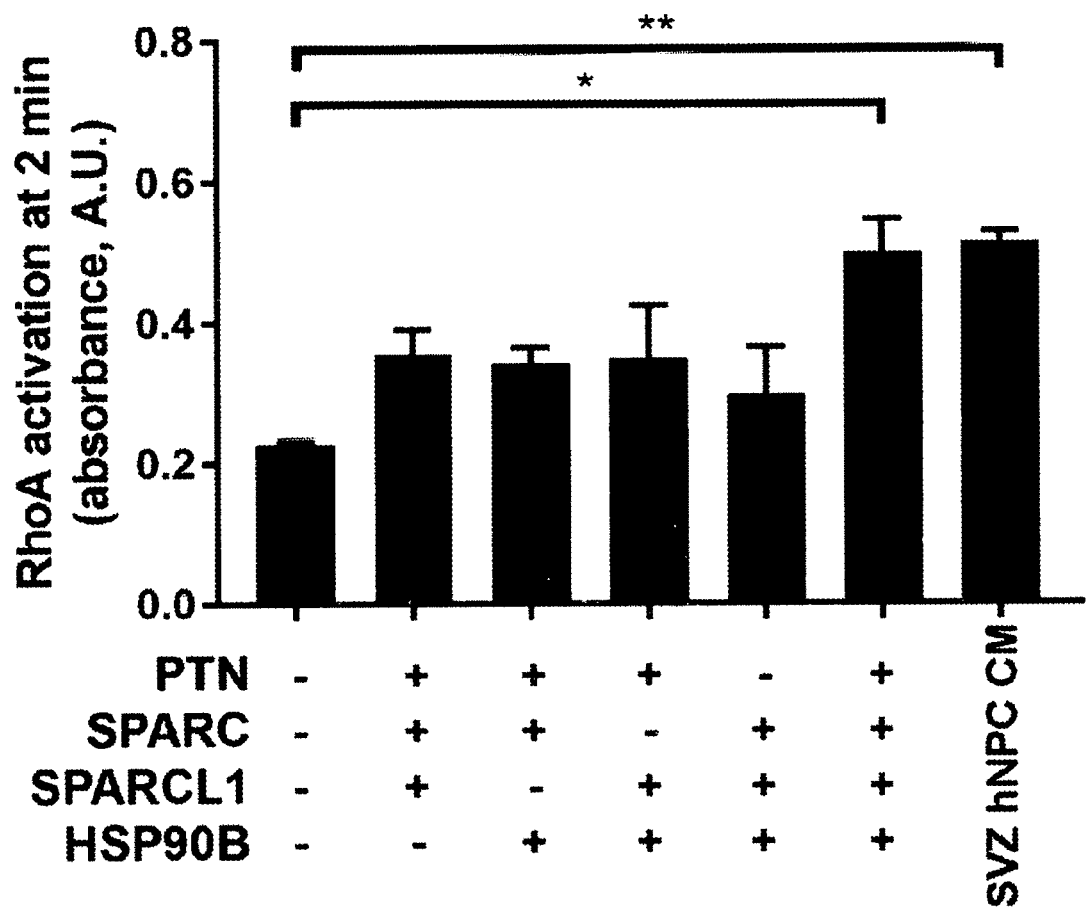
Figure 7D:
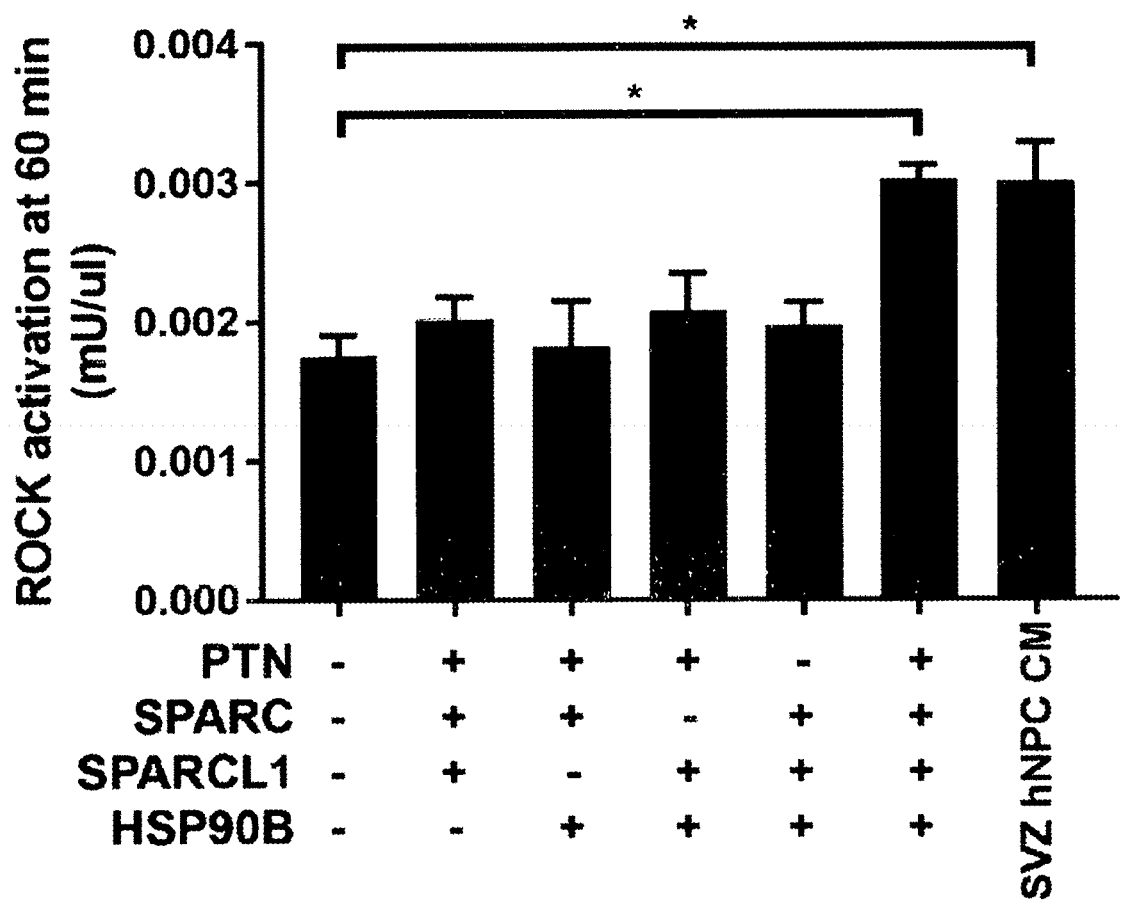
Figure 7E:
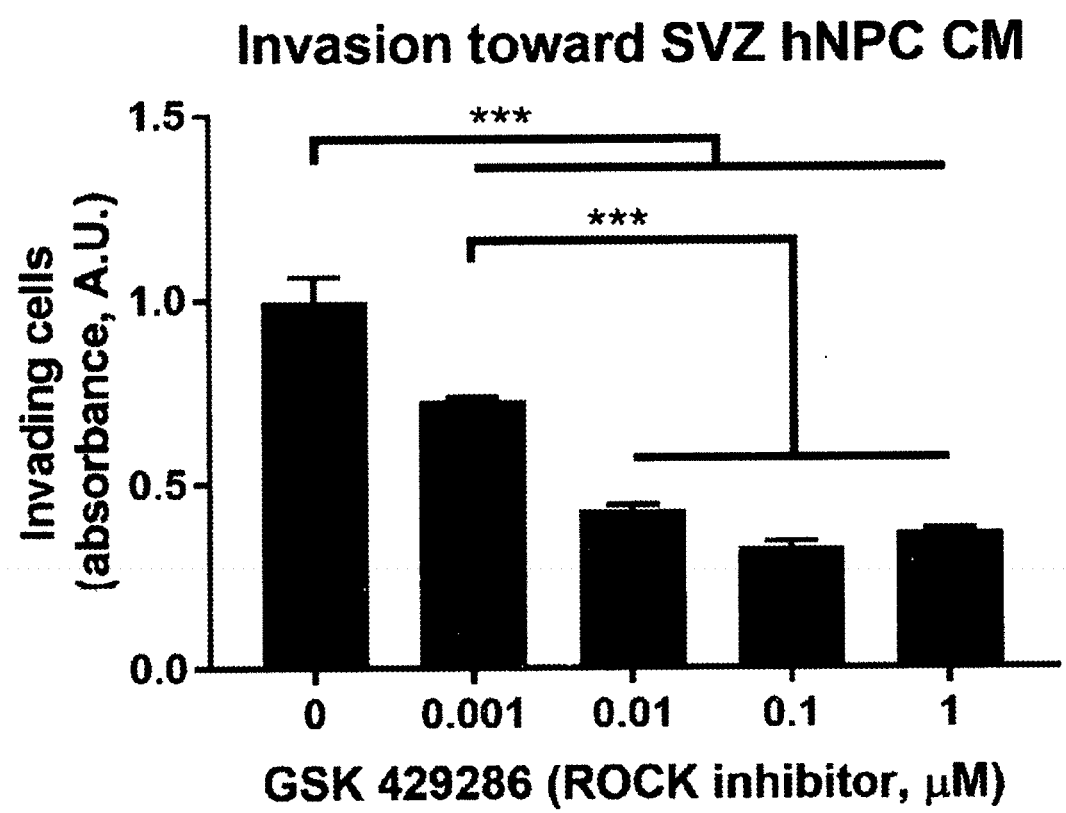
Figure 7F:
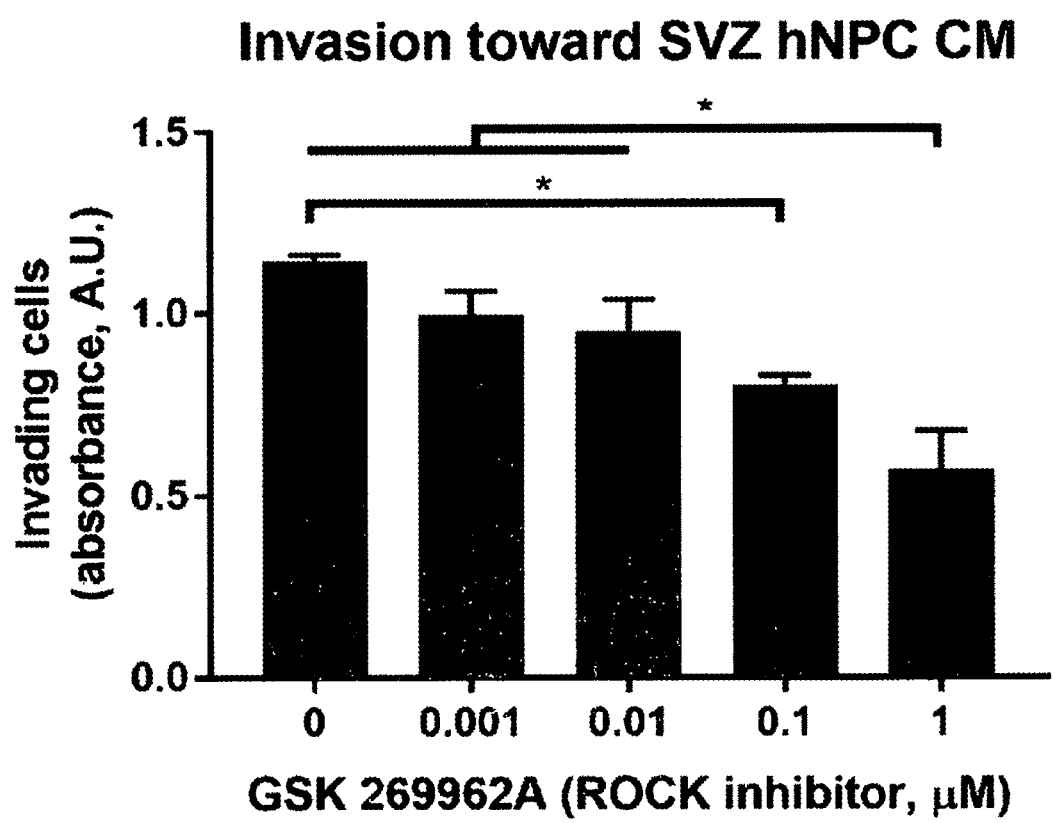
Figure 7G:
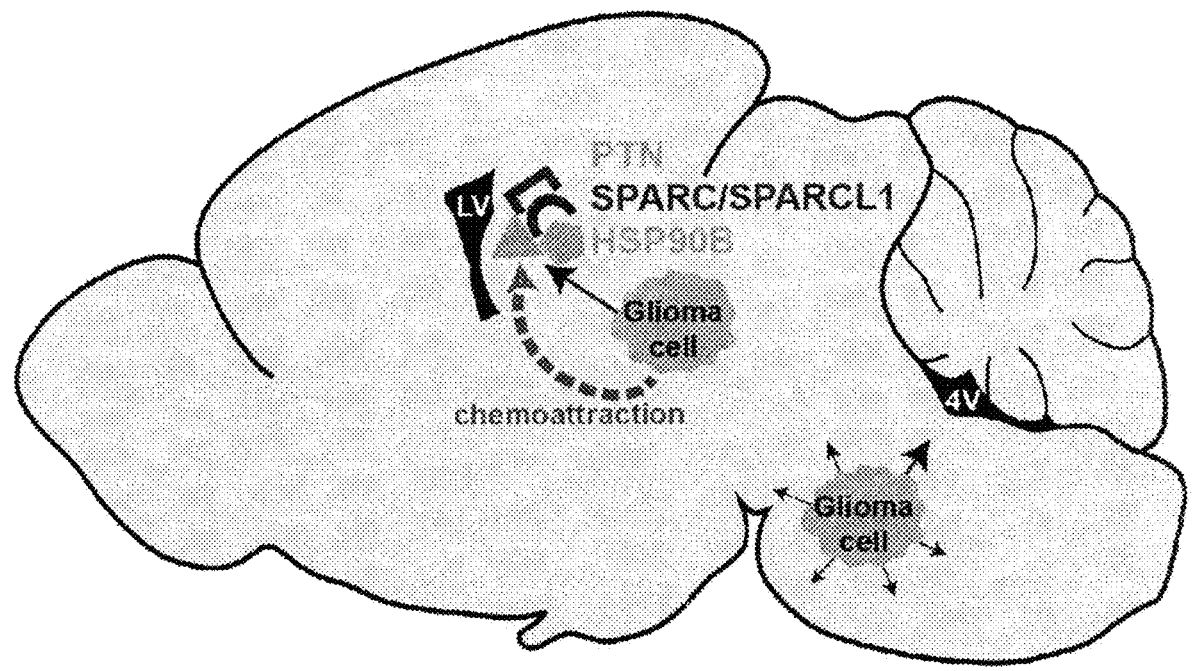
Figure 7H:
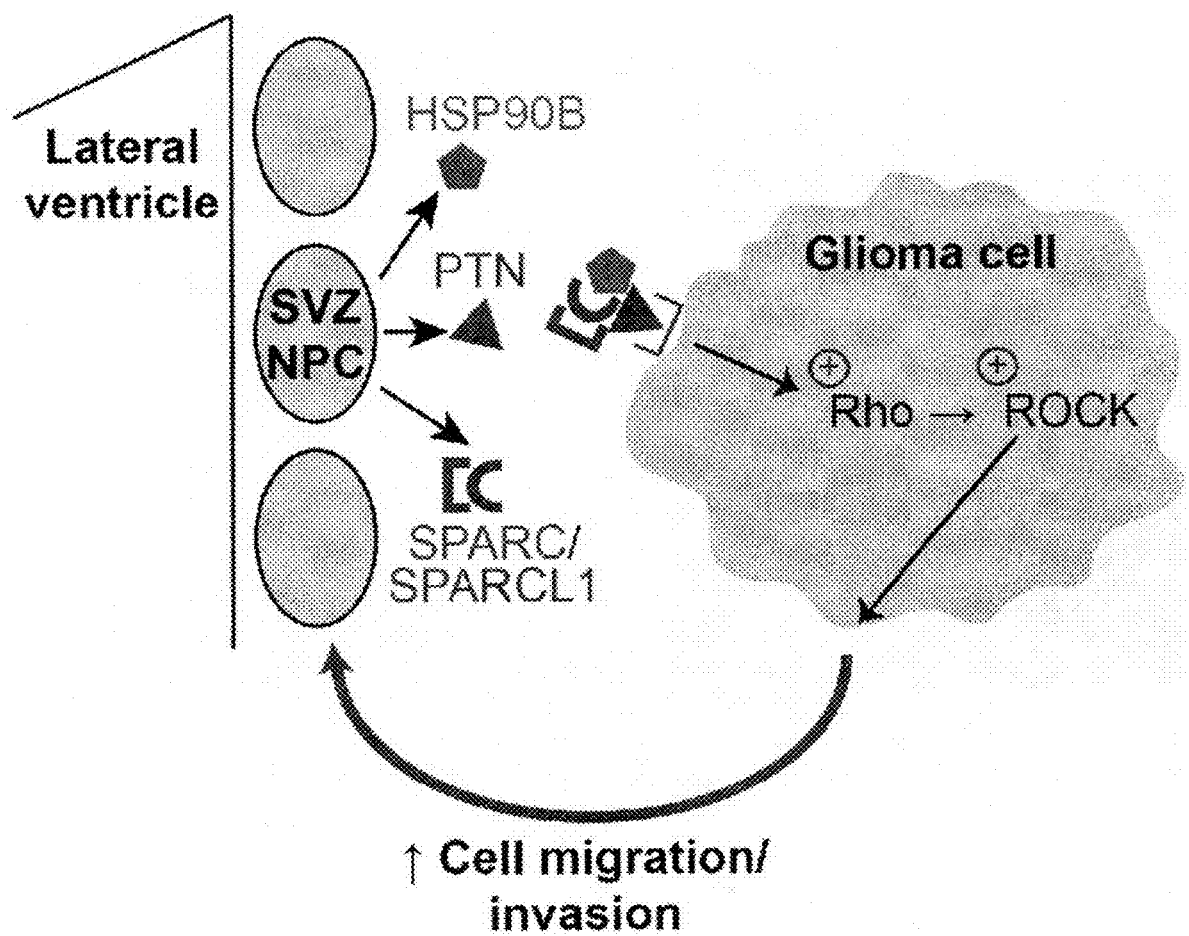
Figure 14A:
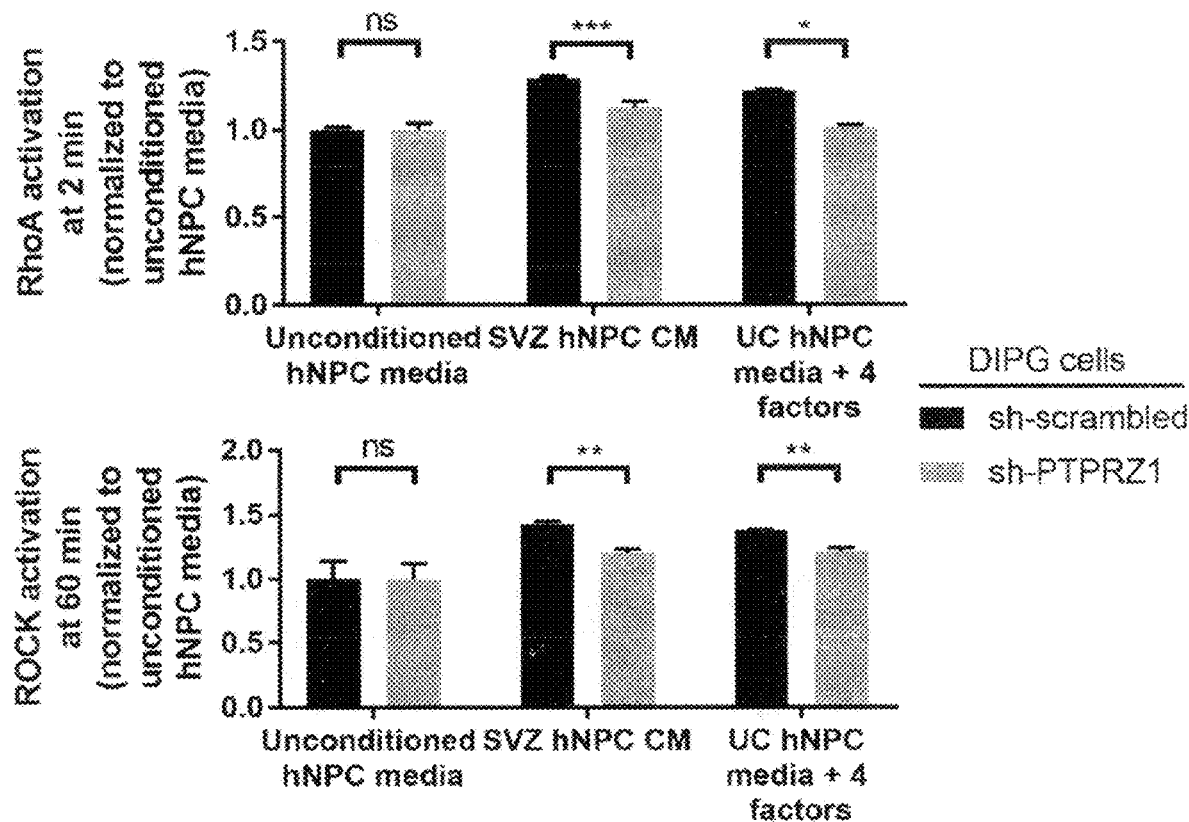
FIGS. 14A-14C show Rho/ROCK activation and ROCK inhibition in DIPG cells (related to FIG. 7).
Figure 14B:
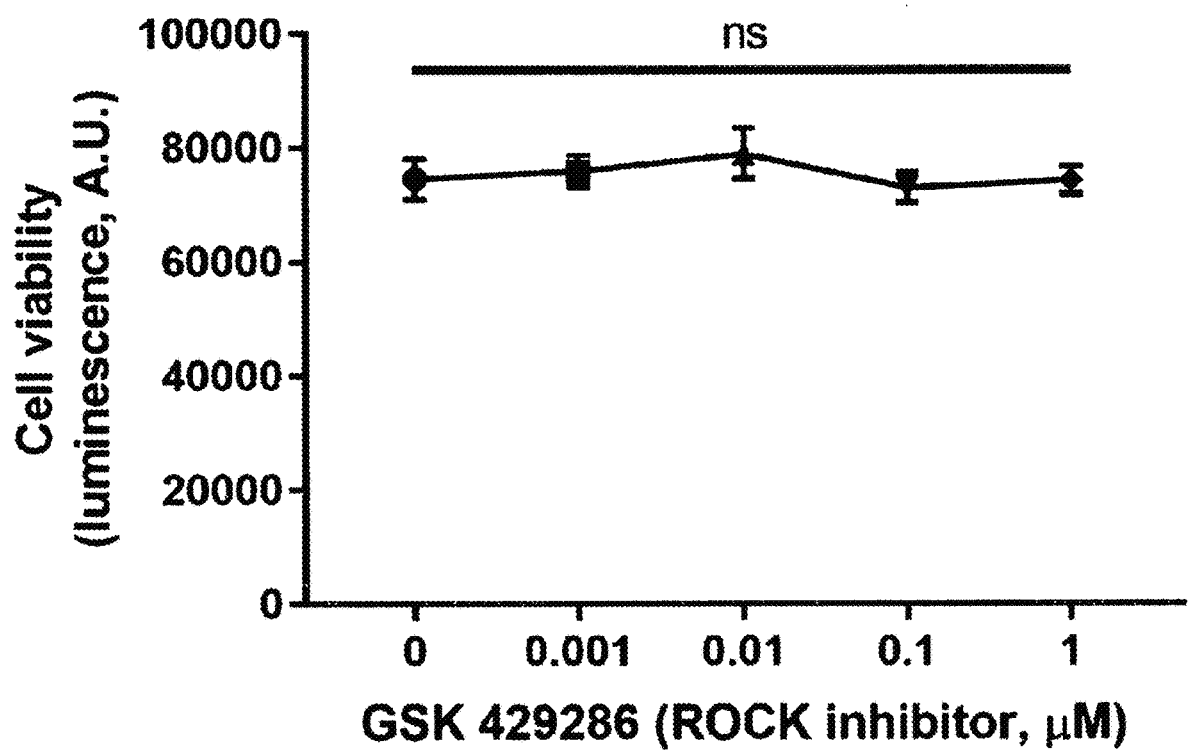
Figure 14C:
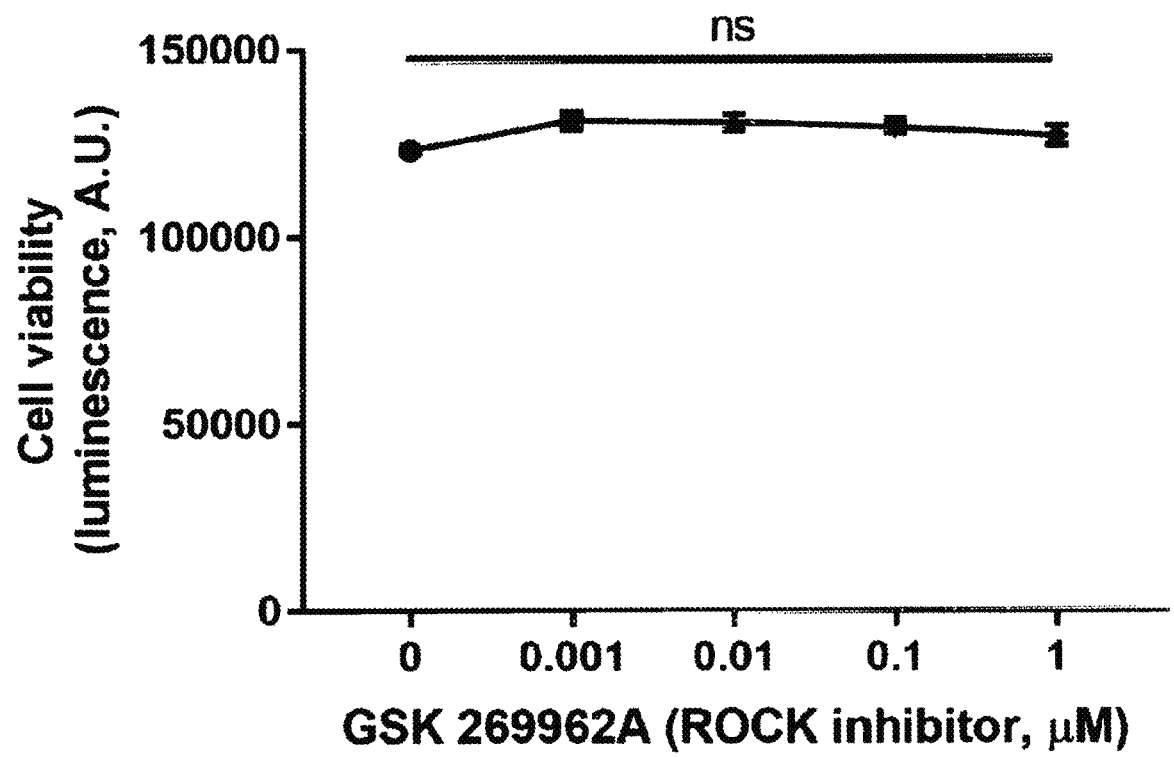

ROCK activation occurs at a later time point, after exposure to SVZ hNPC CM for 60-120 minutes (FIG. 7B). Exposure to the PTN complex activated RhoA and ROCK at levels similar to exposure to SVZ hNPC CM (FIGS. 7C, 7D). DIPG cells with shRNA-mediated knockdown of PTPRZ1 exhibited abrogation of RhoA and ROCK activation when exposed to SVZ hNPC CM or the PTN complex, compared to scrambled control DIPG cells (FIG. 14A), further supporting that PTN-PTPRZ signaling results in activation of the Rho/ROCK pathway. Exposure of DIPG cells to two different ROCK inhibitors decreased DIPG invasion toward SVZ hNPC CM (FIGS. 7E, 7F), without affecting cell viability (FIGS. 13B, 13C). These results implicate the involvement of the Rho/ROCK pathway in promoting DIPG invasion in response to the SVZ NPC-secreted PTN complex. Thus, DIPG cells originating in the pons invade widely throughout the brain, and when in proximity to SVZ NPCs, are drawn in to the SVZ by PTN and its three required binding partners (FIG. 7G). NPC-secreted PTN and binding partners activate the Rho/ROCK pathway in DIPG cells, which promotes glioma cell migration and invasion (FIG. 7H).

Discussion

The present study demonstrates a pathogenic role for NPC:glioma interactions and defines glioma chemoattractants secreted by SVZ NPCs. While NPCs are known to migrate toward and track glioma cells (Aboody et al. (2000) Proc. Natl. Acad. Sci. 97, 12846-12851; Li et al. (2007) Cancer Lett. 251, 220-227; Reitz et al. (2012) Stem Cells Transl. Med. 1, 866-873) in response to glioma-secreted cytokines (Ehtesham et al. (2004) Neoplasia 6(3), 287-293; Imitola et al. (2004) Proc. Natl. Acad. Sci. U.S.A. 101, 18117-18122; Magge et al. (2009) J. Neurosci. Res. 87, 1547-1555) and additional signals (An et al. (2009) J. Proteome Res. 8, 2873-2881; Staflin et al. (2009) BMC Cancer 9, 206), glioma migration/invasion towards NPC populations has been underrecognized. Pleiotrophin, along with three required binding partners, mediates chemoattraction toward the SVZ. Pleiotrophin, specifically enriched in the SVZ after early postnatal neurodevelopment and secreted by SVZ NPCs, interacts with three additional proteins secreted by NPCs that together are sufficient for invasion of a range of molecularly and clinically distinct glioma types, and activates the Rho/ROCK pathway in glioma cells. Pleiotrophin knockdown in NPCs abrogates glioma invasion toward the SVZ in the murine brain. Taken together, these findings identify pleiotrophin and its binding partners as key chemoattractant proteins secreted by SVZ NPCs that are necessary and sufficient for glioma invasion of the SVZ niche.

Implications for Glioma

The SVZ is a site of frequent spread in HGG, and glioma spread to the SVZ is associated with decreased survival rates (Chaichana et al. (2008) J. Neurooncol. 89, 219-224; Jafri et al. (2013) Neuro. Oncol. 15, 500 91-96; Mistry et al. (2017) J. Neurooncol. 131, 125-133; Mistry et al. (2017) J. Neurooncol. 132(2):341-349) and increased tumor recurrence (Adeberg et al. (2014) Int. J. Radiat. Oncol. Biol. Phys. 90, 886-893; Chen et al. (2015) Radiother. Oncol. 116, 294-300). Notably, decreased survival and increased early recurrence in adult GBM are associated specifically with glioma contact of the SVZ (Mistry et al. (2017) J. Neurooncol. 132(2):341-349), for reasons that have yet to be fully elucidated. Clinical studies have sought to improve outcomes by increasing the radiation dose to the SVZ in GBM patients, which in some cases has increased progression-free survival (Chen et al. (2013) Int. J. Radiat. Oncol. 86, 616-622; Evers et al. (2010) BMC Cancer 10, 384; Lee et al. (2013) Int. J. Radiat. Oncol. 86, 609-615). Mortality typically results from brainstem disease in DIPG. The spread of DIPG to the SVZ can result in increased morbidity and mortality. As more effective disease control is achieved in the pons for children with DIPG, regions of distant spread such as the SVZ may emerge as a larger clinical problem.

Understanding DIPG invasion of the SVZ informs not only the pathobiology of this important pediatric cancer, but also provides clarity to mechanisms of SVZ involvement that are conserved across HGG types. DIPG travels some distance between its origins in the pons and the lateral ventricle SVZ. The pattern of DIPG spread found at the time of autopsy is widespread and multidirectional, extending posteriorly to the cerebellum, inferiorly to the medulla, as well as superiorly to the forebrain (Caretti et al. (2014) Acta Neuropathol. 128, 605-607). These neuropathological observations are consistent with an intrinsic invasiveness of DIPG cells (Nagaraja et al. (2017) Cancer Cell 31, 635-652.e6) and the finding presented here that fourth ventricular zone NPCs, located in close anatomical proximity to the pontine tumor, have a minor role in promoting general DIPG cell invasiveness. When DIPG cells invade the forebrain, the demonstrated chemoattractant effect of SVZ NPCs may then act at short to medium range to draw invading cells to the SVZ niche. Additional growth-promoting factors present in the SVZ stem cell niche may function to encourage blooming of substantial masses when glioma cells arrive there.

Pleiotrophin has Pleiotrophic Roles in Development and Cancer

Pleiotrophin (PTN), also known as heparin-binding growth-associated molecule, is a developmentally regulated, secreted growth factor with numerous and diverse roles in brain development, homeostasis, and regeneration. Pleiotrophin has several possible receptors, including protein tyrosine phosphatase receptor type ζ (PTPRZ), anaplastic lymphoma kinase (ALK), N-syndecan, neuroglycan, integrin αvβ3, and lipoprotein receptor-related protein (LRP) (Gonzalez-Castillo et al. (2015) Front. Cell. Neurosci. 8, 443), and as such, the functional effects of pleiotrophin binding are cell context-specific. Pleiotrophin was originally recognized to promote neurite outgrowth (Kinnunen et al. (1999) Eur. J. Neurosci. 11, 491-502; Li et al. (1990) Science 250, 1690-1694; Rauvala and Pihlaskari (1987) J. Biol. Chem. 262, 16625-16635) and subsequently found to promote haptotactic neuroblast migration along radial glial processes from the subventricular germinal zone to the developing cortical plate during corticogenesis (Maeda and Noda (1998) J. Cell Biol. 142(1), 203-216). Additional functions of pleiotrophin range from supporting dendrite and axonal regeneration (Blondet et al. (2005) J. Histochem. Cytochem. 53, 971-977; Mi et al. (2007) Proc. Natl. Acad. Sci. 104, 4664-4669) to modulation of synaptic plasticity (Lauri et al. (1998) Eur. J. Neurosci. 10, 188-194; Pavlov et al. (2002) Mol. Cell. Neurosci. 20, 330-342). Pleiotrophin and PTPRZ are both highly expressed in human white matter oligodendroglial precursor cells (OPCs), and PTN-PTPRZ signaling promotes adult OPC differentiation during developmental myelination and remyelination after injury (Harroch et al. (2002) Nat. Genet. 32, 411-414; Sim et al. (2006) Ann. Neurol. 59, 763-779). In prenatal human OPCs, PTN-PTPRZ signaling promotes proliferation, population expansion, and self-renewal through downstream regulation of the Wnt pathway (McClain et al. (2012) J. Neurosci. 32, 15066-15075). Underscoring the broad roles for pleiotrophin in neurodevelopment, pleiotrophin knockout mice exhibit aberrant cognitive behavior as well as anomalies in corticogenesis (Hienola et al. (2004) Mol. Cell. Neurosci. 26, 75-88; Krellman et al. (2014) PLoS One 9, e100597).

Here we show that after development, pleiotrophin expression is highly enriched in the murine and human SVZ. The identification of pleiotrophin as a protein secreted by murine and human SVZ NPCs is consistent with reports identifying PTN in the secretomes of various neural stem cell populations (Furuta et al. (2004) PLoS One 9, e100597; Lee et al. (2012) PLoS One 7, e50501). While this suggests a role for pleiotrophin in the postnatal SVZ niche, the in vivo function of pleiotrophin and the reasons for its elevated expression in the SVZ compared to other neural stem cell niches remain to be fully elucidated.

In addition to its roles in normal neurodevelopment, plasticity, and regeneration, pleiotrophin also has many roles in cancer, including involvement in tumor growth (Tsirmoula et al. (2012) Cancer Sci. 103, 1826-1832; Wellstein et al. (1992) J. Biol. Chem. 267, 2582-2587) and invasion and metastasis (Czubayko et al. (1996) Proc. Natl. Acad. Sci. U.S.A. 93, 14753-14758; Wu et al. (2005) J. Cutan. Pathol. 32, 125-130). Pleiotrophin is expressed by HGG cells, and expression levels are inversely correlated with overall patient survival (Zhang et al. (2015) Sci. Signal. 8, ra125-ra125). Autocrine/paracrine secretion of pleiotrophin promotes adult GBM migration via PTN-PTPRZ signaling (Lu et al. (2005) J. Biol. Chem. 280, 26953-26964; Ulbricht et al. (2003) J. Neuropathol. Exp. Neurol. 62, 1265-1275). Like neuroblasts during corticogenesis (Maeda and Noda (1998) J. Cell Biol. 142(1), 203-216), GBM cells exhibit robust haptotactic migration toward immobilized pleiotrophin, but only show weak chemotactic migration toward free soluble pleiotrophin (Lu et al., supra; Ulbricht et al., supra). The finding here that NPC-secreted pleiotrophin requires three binding partners may reflect a similar requirement for immobilization to encourage haptotactic migration into the SVZ.

The Rho/ROCK Pathway in Glioma Migration and Invasion

Rho/Rho kinase (ROCK) signaling is a well-established pathway in cell migration. It is a complex pathway, and its role in glioma migration and invasion may be context-specific. In normal cell migration, active ROCK promotes the LIM kinase/cofilin pathway, thereby promoting stabilization of actin filaments (Maekawa et al. (1999) Science 285, 895-898; Sumi et al. (2001) J. Biol. Chem. 276, 23092-23096). In a parallel pathway, active ROCK inhibits myosin light chain phosphatase, thus promoting actin and myosin crosslinking. This leads to contraction of the trailing edge and forward motion of the cell, and thereby increases cell migration (Mitchison and Cramer (1996) Cell 84, 371-379). Consistent with the potential pro-motility effects of modulating Rho/ROCK pathway activity in either direction, the role of Rho/ROCK in glioma migration and invasion is complex and seemingly contradictory. Some studies found that inhibition of ROCK decreased glioma migration (Lin et al. (2009) Oncol. Rep. 22, 1033-1037; Oellers et al. (2009) Glia 57, 499-509), while another study found that inhibition of ROCK increased glioma migration and invasion (Salhia et al. (2005) Cancer Res. 65, 8792-8800). Here, we find that pleiotrophin and its binding partners activate the Rho/ROCK pathway in glioma cells, and treatment with ROCK inhibitors decreases their invasion toward factors secreted by SVZ NPCs, thus implicating this prominent migration pathway in glioma invasion of the SVZ.

Neurite Outgrowth/Axon Guidance Molecules in Glioma Invasion

An emerging theme in glioma pathobiology is malignant hijacking of neurodevelopmental mechanisms (for review, see Baker, Ellison, and Gutmann (2016) Glia 64(6):879-

895), including the re-purposing of traditional neurite outgrowth and axon guidance molecules to regulate glioma invasion. One major family of axon guidance molecules, the ephrins and Eph receptors, promote migration and invasion in adult GBM (Nakada et al. (2010) Int. J. Cancer 126, 1155-1165; Sikkema et al. (2012) Neuro. Oncol. 14, 1125-1135) and in DIPG (Nagaraja et al. (2017) Cancer Cell 31, 635-652.e6). Netrins are another class of chemoattractant cues for pathfinding axons that promote GBM invasion (Shimizu et al. (2013) J. Biol. Chem. 288, 2210-2222). On the other hand, signals that are chemorepulsive to the axonal growth cone prove inhibitory to glioma invasion. SLIT/ROBO signaling, canonically involved in axon pathfinding as a chemorepulsive ligand-receptor system (Brose et al. (1999) Cell 96, 795-806; Kidd et al. (1999) Cell 96, 785-794), functions similarly as a chemorepellant in glioma (Mertsch et al. (2008) J. Neurooncol. 87, 1-7). Semaphorins function chiefly as short-range inhibitory signals for developing axons, and HGGs express both semaphorins and the receptors plexins and neuropilins (Rieger et al. (2003) Glia 42, 379-389); semaphorin signaling has been found to limit glioma motility (Li and Lee (2010) J. Biol. Chem. 285, 32436-32445; Zhou et al. (2012) Oncol. Rep. 28, 269-275).

As a molecule that promotes neurite outgrowth and neuroblast migration, pleiotrophin appears to similarly promote glioma tropism toward a preferred niche. Identification of pleiotrophin and its binding partners as chemoattractant factors secreted by NPCs begins to explain how and why glioma cells preferentially invade the SVZ. Targeting the pleiotrophin complex, including HSP90 inhibition, and downstream Rho/ROCK signaling emerge as therapeutic strategies to limit or prevent tumor invasion of the SVZ in high-grade gliomas.

STAR Methods
Experimental Model and Subject Details
Mice and Housing Conditions

All animal procedures were approved by the Stanford University Administrative Panel on Laboratory Animal Care and performed in accordance with institutional and National Institutes of Health guidelines. All experiments were performed on NOD-SCID-IL2R gamma chain-deficient (NSG) mice, with male and female animals used equally. Animals were housed according to standard guidelines with free access to food and water in a 12-hour light/dark cycle.

Patient-Derived Glioma Cell Culture

All human tissue studies were performed with informed consent and in accordance with Institutional Review Board (IRB)-approved protocols. Authenticity of all cultures was routinely monitored and validated using short tandem repeat (STR) DNA fingerprinting.

DIPG cell cultures were generated as tumor neurospheres from early post-mortem tissue as previously described (Caretti et al. (2014) Acta Neuropathol. 128, 605-607; Lin and Monje (2017) J. Vis. Exp. e55360-e55360; Monje et al. (2011) Proc. Natl. Acad. Sci. U.S.A. 108, 4453-4458; Venkatesh et al. (2015) Cell 161, 803-816). Briefly, tumor tissue was collected under sterile conditions, and transported in Hibernate-A (Thermo Scientific, Waltham, Mass.) on ice to the laboratory. The tissue was mechanically dissociated, followed by gentle rotation in enzymatic dissociation buffer (HEPE-HBSS with DNase I and liberase) at 37° C. Cells were then passed through a 100 μm cell strainer, and processed through a sucrose gradient to remove myelin. The resulting dissociated cells were treated with ACK lysis buffer (Thermo Scientific, Waltham, Mass.) to remove red blood cells, and plated in a serum-free medium designated "Tumor Stem Media (TSM)," consisting of: Neurobasal (-A) (Invitrogen, Carlsbad, Calif.), B27 (-A) (Invitrogen, Carlsbad, Calif.), heparin (2 μg/mL; Stem Cell Technologies, Vancouver, BC, Canada), human-EGF (20 ng/mL; Shenandoah Biotech, Warwick, Pa.), human-bFGF (20 ng/mL; Shenandoah Biotech, Warwick, Pa.), PDGF-AA (10 ng/mL; Shenandoah Biotech, Warwick, Pa.), and PDGF-BB (10 ng/mL; Shenandoah Biotech, Warwick, Pa.).

The pediatric and adult high-grade gliomas used were obtained at the time of biopsy and cultured and validated in the same way as for DIPG tissue described above.

The oligodendroglioma cultures were obtained at the time of biopsy, and generated similarly to as described above and as previously described (Venkatesh et al., 2015). Briefly, the tissue was chopped finely, followed by gentle rotation in liberase at 37° C. Cells were triturated 8 times through a 10 mL serological pipette, followed by 8 times through a 1 mL pipette tip. The cells were then passed through a 100 μm cell strainer, a sucrose gradient, and treated with ACK lysis buffer as described above. Cells were cultured in flasks coated with Matrigel (BD Biosciences, San Jose, Calif.).

All glioma cells described above were cultured in "Tumor Stem Media (TSM)," a defined, serum-free medium described above. Characteristics of the high-grade glioma cell cultures and fingerprinting analyses are described in Table 1 and Table 2, respectively.

TABLE 1

Characteristics of patient-derived high-grade glioma cell cultures.

| Culture ID | Tumor type, location and grade | Age at diagnosis (years) | Sex | Histone-3 mutational status | Other genomic characteristics | Timepoint tissue obtained | Prior therapy | Survival (months) |
|---|---|---|---|---|---|---|---|---|
| SU-DIPG-IV | DIPG; pons; WHO grade III | 2 | F | H3.1K27M | P53 WT; MDM4 amplified; ACVR1 G328V | Early postmortem autopsy | XRT; cetuximab; irinotecan | 8 |
| SU-DIPG-VI | DIPG; pons; WHO grade III | 7 | F | H3.3K27M | P53 mutated | Early postmortem autopsy | XRT; vorinostat | 6 |
| SU-DIPG-XIII | DIPG; pons; WHO grade IV | 6 | F | H3.3K27M | N/A | Early postmortem autopsy | XRT | 4 |
| SU-DIPG-XVII | DIPG; pons; WHO grade IV | 8 | M | H3.3K27M | N/A | Early postmortem autopsy | XRT + avastin; panobinostat; everolimus | 13 |
| SU-DIPG-XIX | DIPG; pons; WHO grade IV | 2 | M | H3.3K27M | N/A | Early postmortem autopsy | XRT; cabazataxal | 18 |

TABLE 1-continued

Characteristics of patient-derived high-grade glioma cell cultures.

| Culture ID | Tumor type, location and grade | Age at diagnosis (years) | Sex | Histone-3 mutational status | Other genomic characteristics | Timepoint tissue obtained | Prior therapy | Survival (months) |
|---|---|---|---|---|---|---|---|---|
| SU-DIPG-XXI | DIPG; pons; WHO grade IV | 7 | M | H3.1K27M | N/A | Early postmortem autopsy | XRT + MK1775 | 18 |
| SU-DIPG-XXIV | DIPG; pons; WHO grade IV | 6 | F | H3.3K27M | N/A | Early postmortem autopsy | XRT; avastin | 8 |
| SU-DIPG-XXV | DIPG; pons; WHO grade IV | 4 | F | H3.3K27M | N/A | Early postmortem autopsy | XRT | 11 |
| SU-DIPG-XXVII | DIPG; pons; WHO grade IV | 5 | M | H3.3K27M | N/A | Early postmortem autopsy | XRT; ABT888 | 6 |
| SU-DIPG-XXIX | DIPG; pons; WHO grade IV | 6 | F | H3.3K27M | N/A | Early postmortem autopsy | XRT; panobinostat; avastin; THC oil | 12 |
| SU-pSCG-1 | Pediatric spinal cord glioma; spinal cord; WHO grade IV | 12 | M | H3K27M | N/A | Early postmortem autopsy | XRT; thioguanine; procarbazine; CCNU; IV vincristine | 11 |
| SU-pGBM3 | Disseminated glioblastoma; left frontal lobe; WHO grade IV | 20 | M | N/A | IDH-1 WT; P53 mutated | Early postmortem autopsy | XRT; temozolomide; avastin | 9 |
| SU-pcGBM2 | Pediatric cortical glioblastoma; frontal lobe; WHO grade IV | 15 | M | WT | P53 mutated; EGFR amplified; PTEN WT | Biopsy at Diagnosis PTEN | none | N/A |
| SU-GBM034 | Glioblastoma; temporal lobe; WHO grade IV | 70 | M | N/A | IDH-1 WT; PTEN mutated | Biopsy at diagnosis | none | N/A |
| SU-GBM035 | Glioblastoma; temporal lobe; WHO grade IV | 61 | M | N/A | IDH-1 WT | Biopsy at recurrence | XRT; TMZ | N/A |
| SU-GBM047 | Epithelioid glioblastoma; temporal lobe; WHO grade IV | 26 | M | N/A | $BRAF^{V600E}$; P53 WT; EGFR WT; PTEN WT | Second resection | Prior resection, no other therapy | <2 |
| SU-GBM081 | Glioblastoma; temporal lobe; WHO grade IV | 72 | M | N/A | IDH-1 WT; P53 mutated | Biopsy at diagnosis | none | N/A |
| SU-O1 | Oligodendroglioma; WHO grade II | 19 | M | N/A | 1p/19q deletion | Biopsy at diagnosis | none | N/A |
| SU-AO2 | Anaplastic oligodendroglioma; frontal lobe; WHO grade III | 36 (44 at recurrence) | M | N/A | 1p/19q deletion; IDH-1 mutated | Biopsy at time of recurrence | TMZ | N/A |

WHO = World Health Organization;
DIPG = diffuse intrinsic pontine glioma;
XRT = radiotherapy;
TMZ = temozolomide;
STR = short tandem repeat.

TABLE 2

Short tandem repeat DNA fingerprinting of HGG cell cultures.

| STR Fingerprint | AMEL | CSF1P01 | D13S317 | D16S539 | D21S11 | D5S818 | D7S820 | TH01 | TPOX | vWA |
|---|---|---|---|---|---|---|---|---|---|---|
| SU-DIPG-IV | X/X | 9/10 | 7/12 | 9/12 | 29/31 | 12/13 | 10/11 | 6/9.3 | 8/ | 15/19 |
| SU-DIPG-VI | X/X | 9/10 | 11/11 | 8/13 | 29/31 | 10/12 | 8/9 | 7/8 | 8/11 | 17/18 |
| SU-DIPG-XIII | X/X | 9/10 | 11/12 | 11/12 | 30/OL | 12/12 | 9/9 | 6/7 | OL/8 | 13/18 |
| SU-DIPG-XVII | X/Y | 13/13 | 9/9 | 9/12 | 28/29 | 11/11 | 8/9 | 7/7 | 8/11 | 18/19 |
| SU-DIPG-XIX | X/Y | 10/11 | 13/14 | 9/13 | 30/30 | 11/12 | 10/10 | 9.3/9.3 | 8/11 | 17/18 |
| SU-DIPG-XXI | X/Y | 11/12 | 8/13 | 10/10 | 30/32 | 10/11 | 8/9 | 6/6 | 8/12 | 16/19 |
| SU-DIPG-XXIV | X/X | 10/12 | 11/11 | 11/13 | 30/31 | 11/11 | 8/10 | 6/9.3 | 8/11 | 17/19 |
| SU-DIPG-XXV | X/X | 12/12 | 8/11 | 12/13 | 30/35 | 11/13 | 10/12 | 9/9 | 7/8 | 14/18 |
| SU-DIPG-XXVII | X/Y | 11/12 | 9/12 | 10/12 | 30/33.2 | 11/11 | 9/12 | 6/6 | 8/11 | 16/17 |
| SU-DIPG-XXIX | X/X | 10/11 | 11/12 | 11/11 | 28/32.2 | 12/14 | 8/11 | 6/9.3 | 8/11 | 15/19 |

TABLE 2-continued

Short tandem repeat DNA fingerprinting of HGG cell cultures.

| STR Fingerprint | AMEL | CSF1PO1 | D13S317 | D16S539 | D21S11 | D5S818 | D7S820 | TH01 | TPOX | vWA |
|---|---|---|---|---|---|---|---|---|---|---|
| SU-pSCG-1 | X/Y | 10/12 | 12/ | 11/12 | 28/29 | 11/12 | 10/ | 9.3/ | 8/11 | 16/18 |
| SU-pGBM3 | X/Y | 12/12 | 8/15,16 | 9/14 | 30/31 | 9/11 | 8/10 | 9/9.3 | 8/9 | 14/17 |
| SU-pcGBM2 | X/Y | 10/11 | 11/ | 9/11 | 28/30.2 | 11/ | 11/12 | 9.3/ | 8/12 | 17/18 |
| SU-GBM034 | X/Y | 10/12 | 8/8 | 10/12 | 29/30 | 11/13 | 8/1 | 7/7 | 8/11 | 18/18 |
| SU-GBM035 | X/Y | 10/11 | 12/ | 12/13 | 30/ | 11/13 | 10/ | 7/9.3 | 9/12 | 18/20 |
| SU-GBM047 | X/Y | 12/12 | 8/8 | 11/12 | 29/31 | 12/12 | 9/11 | 6/9.3 | 8/11 | 19/19 |
| SU-GBM081 | X/Y | 10/11 | 11/11 | 9/9 | 28/31.2 | 9/12 | 8/13 | 9/9.3 | 8/8 | 16/17 |
| SU-O1 | X/Y | 10/12 | 11/11 | 12/13 | 30/30 | 12/13 | 8/11 | 8/9.3 | 8/11 | 14/14 |
| SU-AO2 | X/Y | 11/13 | 8/12 | 8/11 | 30/33.2 | 11/12 | 8/10 | 9/9 | 8/11 | 16/18 |

Neural Precursor Cell Culture and Generation of Conditioned Media

Human subventricular zone neural precursor cells were a generous gift from Siddhartha Mitra and Samuel Cheshier. The cells were cultured from the subventricular zone of the lateral ventricles (SVZ) from a 19-week fetus. Cells were cultured as a monolayer in human neural precursor cell media (hNPC media), consisting of: Neurobasal (−A) (Invitrogen, Carlsbad, Calif.), B27 (−A) (Invitrogen, Carlsbad, Calif.), heparin (2 µg/mL; Stem Cell Technologies, Vancouver, BC, Canada), human-EGF (20 ng/mL; Shenandoah Biotech, Warwick, Pa.), human-bFGF (20 ng/mL; Shenandoah Biotech, Warwick, Pa.), and human-LIF (20 ng/mL; Millipore, Bedford, Mass.).

Mouse neural precursor cells were cultured from WT BL6/CD1 mice at P14 as described by Walker and Kempermann (J. Vis. Exp. (2014) 640 e51225-e51225). The subventricular zone of the lateral ventricles, third ventricular zone, and fourth ventricular zone were microdissected. The tissue was minced and gently dissociated, passed through a 40 µm filter, and plated. Cells were cultured as a monolayer in mouse neural precursor cell media (mNPC media), consisting of: Neurobasal (−A) (Invitrogen, Carlsbad, Calif.), B27 (−A) (Invitrogen, Carlsbad, Calif.), heparin (2 µg/mL; Stem Cell Technologies, Vancouver, BC, Canada), mouse-EGF (20 ng/mL; Peprotech, Rocky Hill, N.J.), and mouse-FGF-2 (20 ng/mL; Peprotech, Rocky Hill, N.J.).

Conditioned media was collected from mouse and human neural precursor cells at passage 5-10. After passaging, cells were plated in fresh NPC media, and allowed to grow for 7 days, with addition of fresh media on day 3-4. On day 7, cells were spun down, and the conditioned media was collected and passed through a 0.22 µm filter. Conditioned media was either used immediately or frozen at −80° C. for future experiments.

Neuron Culture and Generation of Conditioned Media

Mouse hippocampal neurons were cultured from WT BL6/CD1 mice at P0 as described by Beaudoin et al., 2012. The hippocampus was microdissected, minced, and gently dissociated. Cells were cultured in flasks coated with poly-L-lysine. Cells were plated initially in serum neuronal media, consisting of: Minimal Essential Medium with Earle's salts (Invitrogen, Carlsbad, Calif.), glucose, and fetal bovine serum. All serum neuronal media was removed after the first 4 hours, and cells were subsequently cultured in serum-free neurobasal media, consisting of: Neurobasal (Invitrogen, Carlsbad, Calif.), B27 (Invitrogen, Carlsbad, Calif.), and Glutamax (Invitrogen, Carlsbad, Calif.). Serum-free neurobasal media was refreshed every 3-4 days.

Conditioned media was collected from mouse hippocampal neurons at 3 weeks after plating. At 2 weeks after plating, all media was replaced with fresh serum-free neurobasal media. Fresh media was added after 3-4 days, and on day 7, the conditioned media was collected and passed through a 0.22 µm filter. Conditioned media was either used immediately or frozen at −80° C. for future experiments.

Culture of CHL-1 Melanoma Cells

CHL-1 melanoma cells (ATCC, Manassas, Va.) were cultured in "Tumor Stem Media (TSM)," a defined, serum-free medium described above.

Orthotopic Xenografting and Lentiviral Injections

NSG mice at age P34-36 were orthotopically xenografted with SU-DIPG-XIII frontal lobe CMV-GFP-luciferase cells, in a similar procedure to as previously described (Grasso et al., supra; Venkatesh et al. (2015) Cell 161, 803-816). Briefly, a single-cell suspension of SU-DIPG-XIII frontal lobe CMV-GFP-luciferase cells at passage 16-19 was prepared in sterile HBSS immediately before beginning the xenograft procedure. 600,000 cells in 3 µL were stereotactically injected into the pons of the left hemisphere of NSG mice, through a 31-gauge burr hole. Stereotactic coordinates used were: 1 mm lateral to midline, 0.8 mm posterior to lambda suture, and 5 mm deep. Cells were injected at a rate of 0.4 µL/min using a digital pump and a 31-gauge Hamilton syringe. After infusion of cells, the syringe needle was kept in place for 2 minutes, and then withdrawn manually at a rate of 0.875 mm/min to minimize the backflow of cells.

Mice used for shRNA lentivirus studies received shRNA-expressing lentivirus in the SVZ at P27-29 and DIPG cells in the left pons at P34-36. For lentiviral injections, 2 µL of shRNA-expressing lentivirus were stereotactically injected into the SVZ. Stereotactic coordinates used were: 1.3 mm lateral to midline, 0.1 mm posterior to bregma suture, and 2 mm deep. Virus was injected and the needle was withdrawn according to the same procedure as described above.

Human SVZ Samples

All human tissue studies were performed with informed consent and in accordance with Institutional Review Board (IRB)-approved protocols. Human SVZ samples were obtained at autopsy from an 8-year-old female and a 68-year-old male.

Method Details

Bioluminescent IVIS Imaging

Mice were imaged using an IVIS Spectrum to ensure tumor engraftment and monitor tumor size. Mice were anesthetized under 1% isoflurane, intraperitoneally injected with luciferin (15 mg/kg), and imaged for bioluminescence every minute until the peak total flux was reached.

Drug Treatment of Mice

Orthotopically xenografted mice that were treated with 17-AAG or a vehicle control received treatment from 1 week after xenograft until sacrifice. 17-AAG was freshly formulated immediately before injections at 10 mg/mL in 5% DMSO/95% corn oil. Mice received 50 mg/kg 17-AAG 5 days per week (5 days on, 2 days off). Vehicle-treated control mice received 5 µL/g 5% DMSO/95% corn oil on the same dosing schedule. Mice were perfused 8 weeks after xenograft.

Perfusion and Immunohistochemistry

Mice were intraperitoneally injected with Avertin (tribromoethanol) for anesthesia, and then transcardially perfused with 20 mL of ice-cold PBS. Brains were dissected out and fixed in 4% paraformaldehyde in PBS overnight at 4° C., and were then transferred to 30% sucrose in PBS for cryoprotection. Brains were embedded in Tissue-Tek O.C.T. (Sakura, Torrance, Calif.). Brains from mice older than P10 were sliced into 40 µm coronal or sagittal sections using a sliding microtome (Microm HM450; Thermo Scientific, Waltham, Mass.). Brains from mice age P0 to P10 were sliced into 25 µm coronal sections using a cryostat (Leica Biosystems CM3050 S; 1058 Wetzlar, Germany). For immunohistochemistry, a 1 in 6 series of 25 µm or 40 µm sections was incubated in blocking solution (3% normal donkey serum, 0.3% Triton X-100 in TBS) at room temperature for 1 hour. Sections were incubated in primary antibodies diluted in 1% blocking solution (1% normal donkey serum, 0.3% Triton X-100 in TBS) overnight at 4° C., rinsed in TBS the following day, and then incubated in secondary antibodies diluted in 1% blocking solution overnight at 4° C. The following day, sections were rinsed and mounted using ProLong Gold 1064 mounting medium with DAPI (Life Technologies, Carlsbad, Calif.).

Primary antibodies used were: mouse anti-human nuclei clone 235-1 (1:100; Millipore, Bedford, Mass.), goat anti-pleiotrophin (1:500; Santa Cruz Biotechnology, Santa Cruz, Calif.), goat anti-Sox2 (1:50; R&D Systems, Minneapolis, Minn.), rabbit glial fibrillary acidic protein (1:200; Stem Cell Technologies, Vancouver, Canada), and rat myelin basic protein (1:200; Abcam, Cambridge, Mass.).

Secondary antibodies used were: Alexa 594 donkey anti-goat IgG (1:500; Jackson ImmunoResearch, West Grove, Pa.), Alexa 405 donkey anti-mouse IgG (1:500; Jackson ImmunoResearch, West Grove, Pa.), Alexa 647 donkey-anti-rabbit IgG (1:500; Jackson ImmunoResearch, West Grove, Pa.), Alexa 647 donkey anti-mouse IgG (1:500; Life Technologies, Carlsbad, Calif.), and Alexa 647 donkey anti-rat IgG (1:500; Jackson ImmunoResearch, West Grove, Pa.).

Analysis of Tumor Spread Over Time

For analysis of DIPG spread in the mouse brain over time, 25 mice were orthotopically xenografted as described above. 8 mice were sacrificed at 4 weeks post-xenograft, 8 mice were sacrificed at 8 weeks post-xenograft, and 9 mice were sacrificed at 16 weeks post-xenograft. A 1:6 series of sagittal slices was stained and imaged, and the anatomical locations of GFP$^+$ HNA$^+$ cells throughout each mouse were noted and compared with the Allen Brain Atlas.

Matrigel Invasion Assay

To test for chemoattraction and invasion toward neural precursor cell conditioned media or another candidate chemoattractant, a single-cell suspension of 100,000 DIPG cells in Tumor Stem Media (TSM) base (with B27 (−A) and heparin, without growth factors) was seeded in the top inserts of BioCoat growth factor reduced Matrigel invasion chambers (Corning, Bedford, Mass.), after rehydration of the inserts. Chemoattractant media was added to the bottom of the chamber. All conditions were plated in triplicate. After 72 hours, media was aspirated, and the non-invading cells on top of the layer of Matrigel were scrubbed off. The invading cells were fixed in 4% paraformaldehyde and then stained with 0.1% crystal violet in 10% methanol in distilled water. The number of invading cells was quantified by the intensity of the crystal violet dye on the invading side of the Matrigel. The dye was collected in 10% acetic acid, and absorbance was measured at 595 nm.

To test for phenotypic change induced by direct exposure to neural precursor cell conditioned media, 100,000 DIPG cells were seeded in the top inserts of the Matrigel invasion assay in conditioned media, and TSM base (with B27 (−A) and heparin) was plated in the bottom chambers. The rest of the procedure was performed as described above.

To test the ROCK or HSP90 inhibitors in the Matrigel invasion assay, the inhibitors were added to the suspension of glioma cells in TSM base (with B27 (−A) and heparin) seeded in the top inserts at the appropriate concentrations, and neural precursor cell conditioned media was plated in the bottom chambers. The rest of the procedure was performed as described above.

Biochemical Assays

For protein denaturation, media samples were boiled for 7 minutes at 100° C. For RNA and DNA degradation, media samples were treated with RNase and/or DNase at 2 µg/mL for one hour. For size fractionation, media samples were spun in 30 kDa Amicon ultracentrifugal filters (Millipore, Bedford, Mass.), and volumes were normalized by addition of fresh unconditioned NPC media. All experiments were performed in triplicate.

Two-Dimensional Gel Electrophoresis

Two-dimensional gel electrophoresis (2-D DIGE) and the subsequent protein identification processes were performed by Applied Biomics, Inc (Hayward, Calif.), as previously described (Venkatesh et al., supra). The procedure is summarized in brief below.

Sample Preparation and CyDye Labeling

Protein sample buffer was exchanged into 2-D cell lysis buffer (30 nM Tris-HCl, pH 8.8, containing 7 M urea, 2 M thiourea, and 4% CHAPS), and protein concentration was measured by the Bio-Rad protein assay method (Hercules, Calif.). Proteins were labeled with CyDye, and the labeled samples were mixed together. The 2×2-D sample buffer (8 M urea, 4% CHAPS, 20 mg/mL DTT, 2% pharmalytes, and trace amount of bromophenol blue), 100 µL destreak solution and rehydration buffer (7 M urea, 2 M thiourea, 4% CHAPS, 20 mg/mL DTT, 1% pharmalytes, and trace amount of bromophenol blue) were added to the labeling mix.

IEF and SDS-PAGE

After loading the labeled samples, IEF (pH 3-10) was run according to the GE Healthcare protocol. The IPG strips were incubated in fresh equilibration buffer-1 (50 mM Tris-HCl, pH 8.8, containing 6 M urea, 30% glycerol, 2% SDS, trace amount of bromophenol blue and 10 mg/mL DTT), and subsequently rinsed in fresh equilibration buffer-2 (50 mM Tris-HCl, pH 8.8, containing 6 M urea, 30% glycerol, 2% SDS, trace amount of bromophenol blue, and 45 mg/mL Iodoacetamide) and SDS-gel running buffer. The strips were transferred into 12% SDS-gels, which were run at 15° C. until the dye front ran out of the gels.

Image Scan and Analysis

Immediately after SDS-PAGE, gel images were scanned using Typhoon TRIO (GE Healthcare, Waukesha, Wis.). The images were analyzed by Image Quant software (version 6.0, GE Healthcare, Waukesha, Wis.), and quantitation analysis was done with DeCyder software (version 6.5, GE Healthcare, Waukesha, Wis.). In-gel DeCyder analysis was used to obtain the fold change of protein expression levels.

Protein Identification by Mass Spectrometry

Spot Picking and Trypsin Digestion

Based on the in-gel analysis and spot picking design by DeCyder software, spots of interest were picked up by Ettan Spot Picker (Amersham BioSciences, Piscataway, N.J.). The gel spots were washed and digested with modified porcine trypsin protease (Trypsin Gold, Promega, Madison, Wis.). The digested tryptic peptides were desalted using Zip-tip C18 (Millipore, Bedford, Mass.), and the peptides were eluted using matrix solution (α-cyano-4-hydroxycinnamic acid 5 mg/mL in 50% acetonitrile, 0.1% trifluoroacetic acid, 25 mM ammonium bicarbonate) and spotted on the AB SCIEX MALDI plate (Opti-TOF 384 Well Insert, AB SCIEX, Framingham, Mass.).

Mass Spectrometry

MALDI-TOF MS and TOF/TOF tandem MS/MS were performed using an AB SCIEX TOF/TOF 5800 System (AB SCIEX, Framingham, Mass.). In reflectron positive ion mode, MALDI-TOF mass spectra were acquired, with an average of 4000 laser shots per spectrum. For each sample, TOF/TOF tandem MS fragmentation spectra were acquired, with an average of 4000 laser shots per fragmentation spectrum on each of the 10 most abundant ions in each sample (excluding known background ions such as trypsin autolytic peptides).

Database Search

The resulting peptide mass and associated fragmentation spectra were submitted to search the Swiss-Prot database via a GPS Explorer workstation equipped with MASCOT search engine (Matrix Science, Boston, Mass.). Searches were performed with no constraining protein molecular weight or isoelectric point, with variable oxidation of methionine and carbamidomethylation of cysteine residues, and with one missed cleavage allowed. Candidates with either ion C.I. % or protein score C.I. % greater than 95 were considered significant.

Recombinant Proteins Used

BCAN, PTN, SPARC, SPARCL1 (R&D Systems, Minneapolis, Minn.), GRP78 (Abcam, Cambridge, Mass.), HSP90B (Sigma-Aldrich, St. Louis, Mo.), IGFBP2, and IGFBP4 (PeproTech, Rocky Hill, N.J.).

Size Exclusion Chromatography

Human SVZ neural precursor cell conditioned media was concentrated to 5 mg/mL using 15 kDa Amicon ultracentrifugal filters (Millipore, Bedford, Mass.), and subsequently centrifuged at 21,000 1175×g for 10 minutes. 500 µL of conditioned media was fractionated on a Superose 6 10/300 GL column (GE Healthcare, Waukesha, Wis.) via elution with 1.5 column volumes of gel filtration buffer (25 mM HEPES [pH 7.5], 150 mM NaCl, 1 mM DTT) at a flow rate of 0.25 mL/minute and collecting 250 µL fractions. Each fraction was then analyzed by immunoblotting. The approximate molecular weights of the eluted proteins were determined by comparing with proteins of known molecular weight (Gel Filtration Calibration Kit; GE Healthcare, Waukesha, Wis.).

Immunoprecipitation

Immunoprecipitation reactions were conducted using the Pierce Crosslink Magnetic IP/Co-IP Kit (Thermo Scientific, Waltham, Mass.). 25 µL of Pierce Protein A/G Magnetic Beads per reaction were rinsed and incubated with 5 µg of antibody on a rotating platform for 15 minutes at room temperature. Antibodies used were: mouse anti-pleiotrophin (Santa Cruz Biotechnology, Santa Cruz, Calif.), rabbit anti-SPARC (Santa Cruz Biotechnology, Santa Cruz, Calif.), mouse anti-SPARCL1 (Santa Cruz Biotechnology, Santa Cruz, Calif.), rabbit anti-HSP90B (GeneTex, Irvine, Calif.), rabbit normal IgG (Santa Cruz Biotechnology, Santa Cruz, Calif.), and mouse normal IgG (Santa Cruz Biotechnology, Santa Cruz, Calif.). Beads were rinsed, and subsequently crosslinked to the antibodies using 0.02 mM DSS for 30 minutes at room temperature. Beads were washed and then incubated with a mixed combination of 250 µL neural precursor cell conditioned media and 250 µL IP lysis/wash buffer overnight at 4° C. The following morning, beads were washed, resuspended in Laemmli loading buffer, and boiled at 100° C. for 5 minutes to release the bound antigens from the beads. Samples were loaded immediately onto Western blots for analysis of the bound antigens, or stored at −20° C. for future analysis. For Western blot analysis, 2% of the input conditioned media was loaded, and 5% of the IP bound antigen samples were loaded.

For immunodepletion reactions, 100 µL of beads and 20 µg of antibody were used per reaction. Beads were incubated overnight with pure conditioned media, and subsequently, the beads as well as the unbound sample (the depleted conditioned media) were collected. The depleted conditioned media was used immediately in the Matrigel invasion assay, with an aliquot set aside for confirmation of depletion by Western blot. The rest of the procedure was performed as described above.

Western Blot Analysis

Conditioned media samples were mixed with Laemmli loading buffer (1:4) and boiled for 5 minutes at 100° C. Cells or tissue samples were lysed in RIPA buffer and protease inhibitors, incubated on ice for 30 minutes, and centrifuged for 15 minutes at 15,000 rpm at 4° C. Protein concentration in the lysates was determined using the BCA protein assay (Thermo Scientific, Waltham, Mass.). The protein concentration of the samples was normalized, and samples were mixed with Laemmli loading buffer (1:4) and boiled for 5 minutes at 100° C.

Samples were run on Bio-Rad Mini-Protean TGX precast gels (Bio-Rad, Hercules, Calif.), and the protein was transferred onto polyvinylidene fluoride (PVDF) membranes. Membranes were blocked with 5% bovine serum albumin (BSA) in TBST for 1 hour, and incubated in primary antibodies diluted in 1% BSA/TBST overnight at 4° C. Primary antibodies used were: mouse anti-pleiotrophin (1:100; Santa Cruz Biotechnology, Santa Cruz, Calif.), goat anti-SPARC (1:100; R&D Systems, Minneapolis, Minn.), goat anti-SPARCL1 (1:000; R&D Systems, Minneapolis, Minn.), rabbit anti-HSP90B (GeneTex, Irvine, Calif.), rabbit anti-GRP78 (1:500, Abcam, Cambridge, Mass.), rabbit anti-PTPRZ (Thermo Fisher, Waltham, Mass.), and rabbit beta-actin (1:2000; Cell Signaling, Danvers, Mass.). Secondary antibodies conjugated to horseradish peroxidase (HRP) were added for 1 hour at room temperature. Secondary antibodies used were: goat anti-rabbit IgG-HRP (Cell Signaling, Danvers, Mass.), horse anti-mouse IgG-HRP (Cell Signaling, Danvers, Mass.), and donkey anti-goat IgG-HRP (Santa Cruz Biotechnology, Santa Cruz, Calif.). Proteins were visualized using Clarity Western ECL Substrate (Bio-Rad, Hercules, Calif.).

Dissection of Mouse SVZ and Cortex

The SVZ and cortex were microdissected from P42 WT B16/CD1 mice. The SVZ was microdissected as described in Walker and Kempermann, 2014, and a piece of lateral cortex was taken far from the SVZ. Tissue samples were immediately homogenized in TRIzol Reagent for RNA extraction or in RIPA buffer for protein extraction.

qPCR

Cells or tissue were lysed and homogenized in TRIzol Reagent (Life Technologies, Carlsbad, Calif.) and RNA was extracted according to reagent protocol. RNA was treated with dsDNase, and cDNA was synthesized using Thermo Scientific Maxima First Strand cDNA Synthesis Kit for RT-qPCR with dsDNase (Thermo Fisher Scientific K1671).

RT-PCR was performed on Eppendorf Mastercycler Realplex2 using Universal SYBR Green Supermix (BioRad, Hercules, Calif.). Differential expression was determined using the deltaCt method. Primers used were as follows:

```
mouse Ptn forward:
                                  (SEQ ID NO: 1)
5' CTCTGCACAATGCTGACTGTC 3';

mouse Ptn reverse:
                                  (SEQ ID NO: 2)
5' CTTTGACTCCGCTTGAGGCTT 3';

mouse Actb forward:
                                  (SEQ ID NO: 3)
5' GGCTGTATTCCCCTCCATCG 3';

mouse Actb reverse:
                                  (SEQ ID NO: 4)
5' CCAGTTGGTAACAATGCCATGT 3';

human PTPRZ1 forward:
                                  (SEQ ID NO: 5)
5' GCTTTGATGCGGACCGATTTT 3';

human PTPRZ1 reverse:
                                  (SEQ ID NO: 6)
5' ACGACTAACACTTTCGACTCCA 3'.
``` shRNA-Expressing Lentivirus Preparation and Infection

The shRNA constructs against human and mouse PTN, human SPARC, human SPARCL1, human and mouse HSP90B1, and human PTPRZ1 from the RNAi consortium human collection were purchased from Sigma (St. Louis, Mo.). 293T cells were co-transfected with the shRNA constructs and packaging plasmids (pDelta 8.92+VSV-G) to generate lentiviral particles. Lentiviral particles were concentrated using the polyethylene glycol (PEG) precipitation method, resuspended in PBS, and stored at −80° C.

For lentiviral infection, DIPG cells or neural precursor cells were exposed to shRNA-expressing lentivirus for 16 hours. Puromycin was added 48 hours after infection to select for virally infected cells. After removal of puromycin, shRNA-treated neural precursor cells were grown for 7 days (with addition of media on day 3-4) for generation of conditioned media. After removal of puromycin, shRNA-treated DIPG cells were grown for at least one passage before experimental use.

TABLE 3

Sequences of shRNAs

| Target | Product Number | Sequence |
| --- | --- | --- |
| hPTN | Sigma TRCN0000002774 | CCGGAGGCAAGAAACAGG AGAAGATCTCGAGATCTT CTCCTGTTTCTTGCCTTT TTT (SEQ ID NO: 7) |
| mPTN | Sigma TRCN0000071676 | CCGGGCACAATGCTGACT GTCAGAACTCGAGTTCTG ACAGTCAGCATTGTGCTT TTTG (SEQ ID NO: 8) |
| hSPARC | Sigma TRCN0000008711 | CCGGCCAGGTGGAAGTAG GAGAATTCTCGAGAATTC TCCTACTTCCACCTGGTT TTT (SEQ ID NO: 9) |
| hSPARCL1 | Sigma TRCN0000373631 | CCGGATACCCAATCTGAT GATATTTCTCGAGAAATA TCATCAGATTGGGTATTT TTTG (SEQ ID NO: 10) |
| hHSP90B1 | Sigma TRCN0000029425 | CCGGCCTGTGGATGAATA CTGTATTCTCGAGAATAC AGTATTCATCCACAGGTT TTT (SEQ ID NO: 11) |
| mHSP90B1 | Sigma TRCN0000071925 | CCGGGCTATTCAGTTGGA TGGGTTACTCGAGTAACC CATCCAACTGAATAGCTT TTTG (SEQ ID NO: 12) |
| hPTPRZ1 | Sigma TRCN0000356374 | CCGGATACCTAAGTCTTC GTTAATACTCGAGTATTA ACGAAGACTTAGGTATTT TTTG (SEQ ID NO: 13) |
| scrambled | Addgene 1864 | CCTAAGGTTAAGTCGCCC TCGCTCGAGCGAGGGCGA CTTAACCTTAGG (SEQ ID NO: 14) |

RhoA and ROCK Activation Assays

SU-DIPG-XIII frontal lobe cells were starved in TSM base (without B27 (−A) supplement, heparin, or growth factors) for 48 hours prior to treatment. After treatment, cells were lysed in the RhoA activation assay kit cell lysis buffer (Cytoskeleton, Denver, Colo.). Lysates were incubated on ice for 1 minute, clarified by centrifugation at 10,000×g, 4° C. for 1 minute, and the supernatants were snap-frozen and stored immediately at −80° C. Protein concentrations were measured by the BCA protein assay (Thermo Scientific, Waltham, Mass.), and samples were diluted to 0.5 mg/mL by the addition of cell lysis buffer.

RhoA activation assays were performed using the G-LISA RhoA absorbance-based activation assay (Cytoskeleton, Denver, Colo.). Lysate samples were incubated in a 96-well plate with pre-linked Rho GTP-binding protein for 30 minutes at 4° C. shaking at 400 rpm. Wells were incubated in anti-RhoA primary antibody (1:250) at room temperature for 45 minutes shaking at 400 rpm. Secondary HRP-labeled antibody (1:62.5) was added at room temperature for 45 minutes shaking at 400 rpm. Results were visualized by addition of HRP detection reagents for 12 minutes at 37° C., and the absorbance was read at 490 nm. All assays were performed in triplicate.

ROCK activation assays were performed using the Rho-associated kinase (ROCK) activity assay (Millipore, Bedford, Mass.). Cell lysates were incubated in wells of a myosin phosphatase target subunit 1 (MYPT1) pre-coated 96-well plate, for 30 minutes at 30° C. with moderate shaking. Wells were incubated in anti-phospho-MYPT1 (Thr696) primary antibody (1:1000) for 1 hour with moderate shaking. Goat anti-rabbit IgG HRP secondary antibody (1:2000) was added for 1 hour with moderate shaking. Results were visualized with TMB/E substrate, incubating in the dark for 10 minutes, and absorbance was read at 450 nm. All assays were performed in triplicate.

Pharmacologic Inhibition

DIPG cells were treated with a dose curve of GSK 429286 (Tocris, Bristol, United Kingdom), GSK 269962A (a kind gift from Craig Thomas, National Center for Advancing Translational Sciences), or 17-AAG (SelleckChem, Houston, Tex.). All experiments using pharmacologic inhibitors used vehicle DMSO as a control.

Whole Exome Sequencing

Samples underwent sequencing on an Illumina HiSeq 2500 using Agilent's v6 SureSelect whole exome capture set. Short read sequences from whole exome or whole genome sequencing were aligned to the hg19 assembly of the human genome using bwa. Following duplicate removal with Picard tools variants were called using the Genome Analysis toolkit according to standard Best Practices (Broad) including local re-alignment around Indels, down sampling and variant calling with the Unified Genotyper. Variants were annotated with the variant Effect predictor v74 from Ensembl tools and ANNOVAR to include annotations for variant allele frequency in 1000 genomes dbSNP v 132 and the ExAc database as well as functional annotation tools SIFT 1307 and Polyphen.

Coverage of aligned reads was binned into known exons with BEDTools and log 2 ratios of median coverage in tumor and normal sequences were processed with in-house scripts. CBS binary segmentation was applied to each dataset to provide smoothed log 2 ratios. Genes within common CNVs in normal individuals were excluded from further analysis with reference to the CNV map of the human genome. Exon-level median log ratios and smoothed values were thresholded to call gains and losses above and below log 2 ratios of ±0.3 with a contig of ~1 MB and amplifications and deletions above and below a threshold of ±1.5 with a minimum of 3 contiguous exons.

The accession number for whole exome sequencing data deposited in The European Genome-phenome Archive (EGA) database is EGAS00001002326.

RNA Sequencing

RNA sequencing was performed as previously described (Nagaraja et al. (2017) Cancer Cell 31, 635-652.e6). Cells were lysed in TRIzol Reagent (Life Technologies, Carlsbad, Calif.) and RNA was extracted according to reagent protocol. 2 µg of total RNA was used for poly(A)+ purification using Dynabeads mRNA Purification Kit (Thermo Fisher Scientific 61006). mRNA was fragmented using RNA Fragmentation Reagent (Ambion AM8740) and purified using ethanol precipitation. First strand synthesis was performed with SuperScript II (Invitrogen 18064-014) followed by second strand synthesis using DNA Polymerase I (Invitrogen 18010-025) and RNaseH (Invitrogen 18021-014). The cDNA was purified using MinElute PCR Purification Kit (Qiagen 28606).

Purified cDNA was end-repaired using T4 polymerase, Klenow fragment, and T4 PNK and then A-tailed using (exo-) Klenow. NEBNext Multiplex Oligo adaptors (New England BioLabs, E7335S) were ligated using Quick Ligation Kit (New England Biolabs, M2200L) overnight at RT. Adaptors were cut using USER Enzyme and adaptor-ligated libraries were purified by agarose gel electrophoresis. Libraries were amplified using NEBNext Multiplex Oligo primers and final libraries were purified using Ampure XP beads. Sequencing was performed on an Illumina NextSeq by Stanford Functional Genomics Facility.

Reads were aligned to the hg19 genome using tophat2 (Kim et al. (2013) Genome Biol. 14, R36). Transcript abundance was calculated using featureCounts against a RefSeq gene annotation (Liao et al. (2014) Bioinformatics 30(7), 923-30). Differential testing was done using DESeq2 with default median normalization (Love et al. (2014) Genome Biol. 15, 550). Gene Ontology on upregulated genes was performed using Gene Ontology Consortium (Ashburner et al. (2000) Nat. Genet. 25, 25-29). Volcano plot was made in R.

RNA sequencing data were deposited in the GEO database: accession number GSE99812.

CellTiter-Glo Assay

To assess cell viability, 5,000 DIPG cells per well were seeded in base media or full growth media in a 96-well plate. Inhibitors were added at the appropriate concentrations. After 72 hours, CellTiter-Glo reagent 2.0 was added at a 1:1 ratio, and cells were lysed. Luminescence was measured after stabilization of signal for 10 minutes at room temperature.

Quantification and Statistical Analysis

Stereological Cell Counting

For quantification of DIPG invasion of the SVZ after knock down of targets in the SVZ, 5 NSG mice per group were injected with shRNA-expressing lentivirus in bilateral SVZs and orthotopically xenografted with SU-DIPG-XIII FL in the left pons. Mice were perfused for analysis 16 weeks after xenograft. A 1:6 series of coronal slices from each mouse brain was immunostained and imaged, and the number of $GFP^+$ $HNA^+$ glioma cells within 200 µm of the lateral ventricles in all slices containing lateral ventricles was manually counted.

For quantification of neural stem/precursor cells in the SVZ after knock down of PTN in the SVZ, a 1:6 series of coronal slices from each mouse was immunostained and imaged, and the number of $Sox2^+$ neural stem/precursor cells in a 20×Z-stack was manually counted. The density of $Sox2^+$ cells was calculated as cells/mm$^3$.

Statistical Analyses

All statistical analyses were performed using GraphPad Prism. The Shapiro-Wilk normality test was used to confirm Gaussian distribution for parametric analyses. For parametric datasets, unpaired two-tailed Student's t-tests were used for comparisons between two samples, and group mean differences between more than two samples were assessed using one-way analysis of variance (one-way ANOVA) with Tukey or Dunnett post hoc tests to adjust for multiple comparisons. For nonparametric datasets, unpaired two-tailed Mann-Whitney tests were used for comparison between two samples. A level of p<0.05 was used to determine significant differences.

While the preferred embodiments of the invention have been illustrated and described, it will be appreciated that various changes can be made therein without departing from the spirit and scope of the invention.

What is claimed is:

1. A method of treating glioma comprising administering to a subject in need thereof a therapeutically effective amount of at least one inhibitory nucleic acid that inhibits expression of one or more genes selected from the group consisting of PTN, HSP90B, SPARC, SPARCL1, and PTPRZ, wherein said at least one inhibitory nucleic acid is administered locally into the subventricular zone (SVZ) of the brain of the subject.

2. The method of claim 1, wherein said at least one inhibitory nucleic is selected from the group consisting of a short hairpin RNA (shRNA), a small interfering RNA (siRNA), a microRNA (miRNA), and an antisense oligonucleotide.

3. The method of claim 1, wherein the shRNA is selected from the group consisting of:
   a) an shRNA comprising a nucleotide sequence selected from the group consisting of SEQ ID NOS:7-13; and
   b) an shRNA comprising a nucleotide sequence having at least 95% identity to a sequence selected from the group consisting of SEQ ID NOS:7-13.

4. The method of claim 1, wherein the inhibitory nucleic is administered stereotactically into the SVZ of the brain of the subject.

5. The method of claim 1, wherein the glioma is a high-grade glioma.

6. The method of claim 1, wherein the glioma is selected from the group consisting of diffuse midline glioma, H3K27M mutant, adult glioblastoma, adult anaplastic oligodendroglioma, and pediatric spinal cord high-grade glioma.

7. A method of treating diffuse midline glioma, H3K27M mutant comprising administering to a subject in need thereof a therapeutically effective amount of at least one inhibitory nucleic acid that inhibits expression of one or more genes selected from the group consisting of PTN, HSP90B, SPARC, SPARCL1, and PTPRZ, wherein the diffuse midline glioma is an H3.3K27M mutant or an H3.1 K27M mutant subtype.

8. The method of claim 1, wherein treatment reduces glioma invasion toward a brain subventricular zone.

9. The method of claim 8, wherein knockdown of at least one gene selected from the group consisting of PTN, HSP90B, SPARC, and SPARCL1 inhibits assembly of a chemoattractant complex in the brain subventricular zone.

10. The method of claim 1, wherein knockdown of PTN or PTPRZ inhibits pleiotrophin signaling through protein tyrosine phosphatase receptor type ζ.

11. The method of claim 1, wherein knockdown of PTN or PTPRZ reduces activation of RhoA and Rho kinase (ROCK).

12. The method of claim 1, wherein the subject is a human being.

13. The method of claim 1, wherein the inhibitory nucleic acid is provided by a vector.

14. The method of claim 13, wherein the vector is a non-viral or viral vector.

15. The method of claim 1, wherein multiple cycles of treatment are administered to the subject for a time period sufficient to effect at least a partial tumor response.

16. The method of claim 15, wherein multiple cycles of treatment are administered to the subject for a time period sufficient to effect a complete tumor response.

17. The method of claim 1, further comprising administering a Rho kinase (ROCK) inhibitor.

18. The method of claim 17, wherein the ROCK inhibitor is GSK 429286 or GSK 269962A.

19. The method of claim 1, further comprising performing surgery, radiation therapy, chemotherapy, or anti-angiogenic therapy.

20. A method of inhibiting glioma tropism towards a brain subventricular zone in response to a chemoattractant complex, the method comprising administering to a subject in need thereof at least one inhibitory nucleic acid that inhibits expression of one or more genes selected from the group consisting of PTN, HSP90B, SPARC, and SPARCL1, wherein said at least one inhibitory nucleic acid is administered in an amount sufficient to interfere with assembly of the chemoattractant complex in the brain subventricular zone.

21. The method of claim 20, wherein said at least one inhibitory nucleic is selected from the group consisting of a short hairpin RNA (shRNA), a small interfering RNA (siRNA), a microRNA (miRNA), and an antisense oligonucleotide.

22. The method of claim 21, wherein the shRNA is selected from the group consisting of:

a) an shRNA comprising a nucleotide sequence selected from the group consisting of SEQ ID NOS:7-13; and b) an shRNA comprising a nucleotide sequence having at least 95% identity to a sequence selected from the group consisting of SEQ ID NOS:7-13.

23. The method of claim 20, wherein the inhibitory nucleic is administered stereotactically into the brain of the subject.

24. The method of claim 20, wherein the glioma is a high-grade glioma.

25. The method of claim 20, wherein the glioma is selected from the group consisting of diffuse midline glioma, H3K27M mutant, adult glioblastoma, adult anaplastic oligodendroglioma, and pediatric spinal cord high-grade glioma.

26. A method of inhibiting diffuse midline glioma, H3K27M mutant tropism towards a brain subventricular zone in response to a chemoattractant complex, the method comprising administering to a subject in need thereof at least one inhibitory nucleic acid that inhibits expression of one or more genes selected from the group consisting of PTN, HSP90B, SPARC, and SPARCL1, wherein said at least one inhibitory nucleic acid is administered in an amount sufficient to interfere with assembly of the chemoattractant complex in the brain subventricular zone, wherein the diffuse midline glioma is an H3.3K27M mutant or an H3.1 K27M mutant subtype.

* * * * *

SEQUENCE LISTING

<160> NUMBER OF SEQ ID NOS: 14

<210> SEQ ID NO 1
<211> LENGTH: 21
<212> TYPE: DNA

```
<213> ORGANISM: Artificial Sequence
<220> FEATURE:
<223> OTHER INFORMATION: mouse Ptn forward primer
<220> FEATURE:
<221> NAME/KEY: source
<222> LOCATION: (1)..(21)
<223> OTHER INFORMATION: sequence is synthesized

<400> SEQUENCE: 1
ctctgcacaa tgctgactgt c                                              21

<210> SEQ ID NO 2
<211> LENGTH: 21
<212> TYPE: DNA
<213> ORGANISM: Artificial Sequence
<220> FEATURE:
<223> OTHER INFORMATION: mouse Ptn reverse primer
<220> FEATURE:
<221> NAME/KEY: source
<222> LOCATION: (1)..(21)
<223> OTHER INFORMATION: sequence is synthesized

<400> SEQUENCE: 2
ctttgactcc gcttgaggct t                                              21

<210> SEQ ID NO 3
<211> LENGTH: 20
<212> TYPE: DNA
<213> ORGANISM: Artificial Sequence
<220> FEATURE:
<223> OTHER INFORMATION: mouse Actb forward primer
<220> FEATURE:
<221> NAME/KEY: source
<222> LOCATION: (1)..(20)
<223> OTHER INFORMATION: sequence is synthesized

<400> SEQUENCE: 3
ggctgtattc ccctccatcg                                                20

<210> SEQ ID NO 4
<211> LENGTH: 22
<212> TYPE: DNA
<213> ORGANISM: Artificial Sequence
<220> FEATURE:
<223> OTHER INFORMATION: mouse Actb reverse primer
<220> FEATURE:
<221> NAME/KEY: source
<222> LOCATION: (1)..(22)
<223> OTHER INFORMATION: sequence is synthesized

<400> SEQUENCE: 4
ccagttggta acaatgccat gt                                             22

<210> SEQ ID NO 5
<211> LENGTH: 21
<212> TYPE: DNA
<213> ORGANISM: Artificial Sequence
<220> FEATURE:
<223> OTHER INFORMATION: human PTPRZ1 forward primer
<220> FEATURE:
<221> NAME/KEY: source
<222> LOCATION: (1)..(21)
<223> OTHER INFORMATION: sequence is synthesized

<400> SEQUENCE: 5
gctttgatgc ggaccgattt t                                              21

<210> SEQ ID NO 6
<211> LENGTH: 22
```

```
<212> TYPE: DNA
<213> ORGANISM: Artificial Sequence
<220> FEATURE:
<223> OTHER INFORMATION: human PTPRZ1 reverse primer
<220> FEATURE:
<221> NAME/KEY: source
<222> LOCATION: (1)..(22)
<223> OTHER INFORMATION: sequence is synthesized

<400> SEQUENCE: 6
acgactaaca ctttcgactc ca                                              22

<210> SEQ ID NO 7
<211> LENGTH: 57
<212> TYPE: DNA
<213> ORGANISM: Artificial Sequence
<220> FEATURE:
<223> OTHER INFORMATION: hPTN shRNA
<220> FEATURE:
<221> NAME/KEY: source
<222> LOCATION: (1)..(57)
<223> OTHER INFORMATION: sequence is synthesized

<400> SEQUENCE: 7
ccggaggcaa gaaacaggag aagatctcga gatcttctcc tgtttcttgc ctttttt       57

<210> SEQ ID NO 8
<211> LENGTH: 58
<212> TYPE: DNA
<213> ORGANISM: Artificial Sequence
<220> FEATURE:
<223> OTHER INFORMATION: mPTN shRNA
<220> FEATURE:
<221> NAME/KEY: source
<222> LOCATION: (1)..(58)
<223> OTHER INFORMATION: sequence is synthesized

<400> SEQUENCE: 8
ccgggcacaa tgctgactgt cagaactcga gttctgacag tcagcattgt gcttttg       58

<210> SEQ ID NO 9
<211> LENGTH: 57
<212> TYPE: DNA
<213> ORGANISM: Artificial Sequence
<220> FEATURE:
<223> OTHER INFORMATION: hSPARC shRNA
<220> FEATURE:
<221> NAME/KEY: source
<222> LOCATION: (1)..(57)
<223> OTHER INFORMATION: sequence is synthesized

<400> SEQUENCE: 9
ccggccaggt ggaagtagga gaattctcga gaattctcct acttccacct ggtttt        57

<210> SEQ ID NO 10
<211> LENGTH: 58
<212> TYPE: DNA
<213> ORGANISM: Artificial Sequence
<220> FEATURE:
<223> OTHER INFORMATION: hSPARCL1 shRNA
<220> FEATURE:
<221> NAME/KEY: source
<222> LOCATION: (1)..(58)
<223> OTHER INFORMATION: sequence is synthesized

<400> SEQUENCE: 10
ccggataccc aatctgatga tatttctcga gaaatatcat cagattgggt atttttg       58

<210> SEQ ID NO 11
```

```
<211> LENGTH: 57
<212> TYPE: DNA
<213> ORGANISM: Artificial Sequence
<220> FEATURE:
<223> OTHER INFORMATION: hHSP90B1 shRNA
<220> FEATURE:
<221> NAME/KEY: source
<222> LOCATION: (1)..(57)
<223> OTHER INFORMATION: sequence is synthesized

<400> SEQUENCE: 11
ccggcctgtg gatgaatact gtattctcga gaatacagta ttcatccaca ggttttt          57

<210> SEQ ID NO 12
<211> LENGTH: 58
<212> TYPE: DNA
<213> ORGANISM: Artificial Sequence
<220> FEATURE:
<223> OTHER INFORMATION: mHSP90B1 shRNA
<220> FEATURE:
<221> NAME/KEY: source
<222> LOCATION: (1)..(58)
<223> OTHER INFORMATION: sequence is synthesized

<400> SEQUENCE: 12
ccgggctatt cagttggatg ggttactcga gtaacccatc caactgaata gcttttttg        58

<210> SEQ ID NO 13
<211> LENGTH: 58
<212> TYPE: DNA
<213> ORGANISM: Artificial Sequence
<220> FEATURE:
<223> OTHER INFORMATION: hPTPRZ1 shRNA
<220> FEATURE:
<221> NAME/KEY: source
<222> LOCATION: (1)..(58)
<223> OTHER INFORMATION: sequence is synthesized

<400> SEQUENCE: 13
ccggatacct aagtcttcgt taatactcga gtattaacga agacttaggt attttttg         58

<210> SEQ ID NO 14
<211> LENGTH: 48
<212> TYPE: DNA
<213> ORGANISM: Artificial Sequence
<220> FEATURE:
<223> OTHER INFORMATION: scrambled shRNA
<220> FEATURE:
<221> NAME/KEY: source
<222> LOCATION: (1)..(48)
<223> OTHER INFORMATION: sequence is synthesized

<400> SEQUENCE: 14
cctaaggtta agtcgccctc gctcgagcga gggcgactta accttagg                    48
```